(12) United States Patent
Glatt et al.

(10) Patent No.: US 11,492,396 B2
(45) Date of Patent: Nov. 8, 2022

(54) METHODS OF TREATMENT USING ANTI-IL-17A/F ANTIBODIES

(71) Applicant: UCB BIOPHARMA SPRL, Brussels (BE)

(72) Inventors: Sophie Glatt, Slough (GB); Lucian Ionescu, Brussels (BE); Margaret Jones, Slough (GB); Ruth Oliver, Slough (GB); Stevan Graham Shaw, Slough (GB); Foteini Strimenopoulou, Slough (GB); Venkata Pavan Kumar Vajjah, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 217 days.

(21) Appl. No.: 15/771,310

(22) PCT Filed: Oct. 26, 2016

(86) PCT No.: PCT/EP2016/075821
§ 371 (c)(1),
(2) Date: Nov. 16, 2018

(87) PCT Pub. No.: WO2017/072183
PCT Pub. Date: May 4, 2017

(65) Prior Publication Data
US 2019/0292255 A1 Sep. 26, 2019

Related U.S. Application Data

(60) Provisional application No. 62/405,546, filed on Oct. 7, 2016, provisional application No. 62/346,826, filed on Jun. 7, 2016, provisional application No. 62/303,230, filed on Mar. 3, 2016, provisional application No. 62/246,989, filed on Oct. 27, 2015.

(51) Int. Cl.
| | |
|---|---|
| *A61K 39/395* | (2006.01) |
| *C07K 16/24* | (2006.01) |
| *A61P 17/06* | (2006.01) |
| *A61P 19/02* | (2006.01) |
| *A61K 39/00* | (2006.01) |

(52) U.S. Cl.
CPC ............ *C07K 16/244* (2013.01); *A61P 17/06* (2018.01); *A61P 19/02* (2018.01); *A61K 2039/505* (2013.01); *A61K 2039/54* (2013.01); *A61K 2039/545* (2013.01); *A61K 2039/55* (2013.01); *C07K 2317/24* (2013.01); *C07K 2317/33* (2013.01); *C07K 2317/34* (2013.01); *C07K 2317/56* (2013.01); *C07K 2317/76* (2013.01)

(58) Field of Classification Search
CPC .............. A61P 17/06; A61K 2039/505; A61K 2039/545; C07K 2317/56
See application file for complete search history.

(56) References Cited

U.S. PATENT DOCUMENTS

| | | | |
|---|---|---|---|
| 4,741,900 | A | 5/1988 | Alvarez et al. |
| 4,946,778 | A | 8/1990 | Ladner et al. |
| 5,219,996 | A | 6/1993 | Bodmer et al. |
| 5,223,409 | A | 6/1993 | Ladner et al. |
| 5,403,484 | A | 4/1995 | Ladner et al. |
| 5,427,908 | A | 6/1995 | Dower et al. |
| 5,516,637 | A | 5/1996 | Huang et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,658,727 | A | 8/1997 | Barbas et al. |
| 5,661,016 | A | 8/1997 | Lonberg et al. |
| 5,667,425 | A | 9/1997 | Pineau et al. |
| 5,698,426 | A | 12/1997 | Huse |
| 5,733,743 | A | 3/1998 | Johnson et al. |
| 5,750,753 | A | 5/1998 | Kimae et al. |
| 5,770,429 | A | 6/1998 | Lonberg et al. |
| 5,780,225 | A | 7/1998 | Wigler et al. |
| 5,821,047 | A | 10/1998 | Garrard et al. |
| 5,969,108 | A | 10/1999 | McCafferty et al. |
| 8,303,953 | B2 | 11/2012 | Adams et al. |
| 8,580,265 | B2 | 11/2013 | Adams et al. |
| 8,679,494 | B2 | 3/2014 | Ceska et al. |
| 2007/0196371 | A1 | 8/2007 | Kuestner et al. |

(Continued)

FOREIGN PATENT DOCUMENTS

| | | |
|---|---|---|
| EP | 0392745 A3 | 3/1991 |
| EP | 0463151 A1 | 1/1992 |

(Continued)

OTHER PUBLICATIONS

Ackermann et al., Economic burden of psoriatic arthritis, *Pharmacoeconomics*. 26:121-9 (2008).
Adair et al., Therapeutic antibodies. D*rug Design Reviews—Online*. 2:209-217 (2005).
Ames et al., Conversion of murine Fabs isolated from a combinatorial phage display library to full length immunoglobulins, *J. Immunol. Methods*. 184:177-86 (1995).
Angal et al., A single amino acid substitution abolishes the heterogeneity of chimeric mouse/human (IgG4) antibody, *Mol. Immunology*. 30:105-8 (1993).
Babcook et al., A novel strategy for generating monoclonal antibodies from single, isolated lymphocytes producing antibodies of defined specificities, *Proc. Natl. Acad. Sci. USA*. 93:7843-78481 (1996).
Baeten et al., Secukinumab, an lnterleukin-17A Inhibitor, in Ankylosing Spondylitis, *New Engl. J. Med*. 373:2534-2548 (2015).

(Continued)

*Primary Examiner* — Dong Jiang
(74) *Attorney, Agent, or Firm* — Marshall, Gerstein & Borun LLP

(57) ABSTRACT

The invention relates to therapeutic uses of antibody molecules having specificity for antigenic determinants of both IL-17A and IL-17F in the treatment of dermatological and rheumatological diseases, such as psoriasis, psoriatic arthritis and axial spondyloarthritis.

12 Claims, 29 Drawing Sheets

Specification includes a Sequence Listing.

(56) References Cited

U.S. PATENT DOCUMENTS

| | | | |
|---|---|---|---|
| 2007/0218065 A1* | 9/2007 | Jaspers | C07K 16/244 424/145.1 |
| 2012/0183558 A1* | 7/2012 | Adams | A61P 17/06 424/158.1 |
| 2013/0202610 A1 | 8/2013 | Guettner et al. | |

FOREIGN PATENT DOCUMENTS

| | | |
|---|---|---|
| EP | 0546073 A1 | 6/1993 |
| EP | 0438474 B1 | 5/1996 |
| EP | 0948544 B1 | 5/2003 |
| WO | WO-1986/01533 A1 | 3/1986 |
| WO | WO-1989/00195 A1 | 1/1989 |
| WO | WO-1989/01476 A1 | 2/1989 |
| WO | WO-1990/02809 A1 | 3/1990 |
| WO | WO-1991/09967 A1 | 7/1991 |
| WO | WO-1991/10737 A1 | 7/1991 |
| WO | WO-1992/01047 A1 | 1/1992 |
| WO | WO-1992/02551 A1 | 2/1992 |
| WO | WO-1992/18619 A1 | 10/1992 |
| WO | WO-1992/22583 A2 | 12/1992 |
| WO | WO-1992/22853 A1 | 12/1992 |
| WO | WO-1993/06231 A1 | 4/1993 |
| WO | WO-1993/08829 A1 | 5/1993 |
| WO | WO-1993/11236 A1 | 6/1993 |
| WO | WO-1995/15982 A2 | 6/1995 |
| WO | WO-1995/20401 A1 | 8/1995 |
| WO | WO-1998/20734 A1 | 5/1998 |
| WO | WO-1998/25971 A1 | 6/1998 |
| WO | WO-2003/031581 A2 | 4/2003 |
| WO | WO-2004/051268 A1 | 6/2004 |
| WO | WO-2004/072116 A2 | 8/2004 |
| WO | WO-2004/106377 A1 | 12/2004 |
| WO | WO-2005/003169 A2 | 1/2005 |
| WO | WO-2005/003170 A2 | 1/2005 |
| WO | WO-2005/003171 A2 | 1/2005 |
| WO | WO-2005/113605 A1 | 12/2005 |
| WO | WO-2005/117984 A2 | 12/2005 |
| WO | WO-2007/106769 A2 | 9/2007 |
| WO | WO-2007/149032 | 12/2007 |
| WO | WO-2008/047134 | 4/2008 |
| WO | WO-2008/067223 A2 | 6/2008 |
| WO | WO-2008/121865 | 10/2008 |
| WO | WO-2009/040562 | 4/2009 |
| WO | WO-2009/130459 | 10/2009 |
| WO | WO-2009/136286 A2 | 11/2009 |
| WO | WO-2010/025400 A2 | 3/2010 |
| WO | WO-2010/035012 A1 | 4/2010 |
| WO | WO-2010/128407 A2 | 11/2010 |
| WO | WO-2011/030107 A1 | 3/2011 |
| WO | WO-2011/061492 A2 | 5/2011 |
| WO | WO-2011/086091 A1 | 7/2011 |
| WO | WO-2012/045848 A1 | 4/2012 |
| WO | WO-2012/095662 A1 | 7/2012 |
| WO | WO-2012/156219 A1 | 11/2012 |
| WO | WO-2013/077907 A1 | 5/2013 |
| WO | WO-2013/158821 A2 | 10/2013 |
| WO | WO-2013/189975 A1 | 12/2013 |
| WO | WO-2014/122613 A1 | 8/2014 |
| WO | WO-2014/155278 A2 | 10/2014 |
| WO | WO-2016/038538 A1 | 3/2016 |
| WO | WO-2017/068472 A1 | 4/2017 |
| WO | WO-2017/102830 A1 | 6/2017 |
| WO | WO-2017/188850 A1 | 11/2017 |

OTHER PUBLICATIONS

Blair et al., Secukinumab: A Review in Ankylosing Spondylitis, *Drugs* 76:1023-30 (2016).
Brinkmann et al., Phage display of disulfide-stabilized Fv fragments, *J. Immunol. Methods* 182:41-50 (1995).
Burns et al., Characterisation of IL-17A, IL-17F and IL-17E expression in human health and inflammatory disease, European Congress of Immunology (2015).
Burton et al., Human antibodies from combinatorial libraries, *Adv. Immunol.* 57:191-280 (1994).
Chai et al., Probing the osteoinductive effect of calcium phosphate by using an in vitro biomimetic model, *Tissue Eng. Part A.* 17:1083-97 (2011).
Chang et al., NF-kB inhibits osteogenic differentiation of mesenchymal stem cells by promoting ?-catenin degradation, *Proc. Natl. Acad. Sci. U.S.A.* 110:9469-9474 (2013).
Chapman, PEGylated antibodies and antibody fragments for improved therapy: a review, *Advanced Drug Delivery Reviews.* 54:531-45 (2002).
Chothia and Lesk, Canonical Structures for the Hypervariable Regions of Immunoglobulins, *J. Mol. Biol.* 196:901-917 (1987).
Clinical Trial No. NCT02141763, Multiple Dose Study of UCB4940 in Subjects with Psoriatic Arthritis, ClinicalTrials.gov, May 19, 2014.
Clinical Trial No. NCT02430909, Multiple Dose Study of UCB4940 as add-on to Certolizumab Pegol in Subjects with Rheumatoid Arthritis, ClinicalTrials.gov, Aug. 30, 2015.
Clinical Trial No. NCT02529965, A Study to Assess the Safety, Pharmacokinetics and Pharmacodynamics of UCB4940 in Patients with Psoriasis, clinicaltrials.gov, Aug. 20, 2015.
Conaghan et al., Improving recognition of psoriatic arthritis, *Practitioner.* 253:15-8 (2009).
Crameri et al., DNA shuffling of a family of genes from diverse species accelerates directed evolution, *Nature.* 391:288-91 (1998).
Croes et al., Proinflammatory T cells and IL-17 stimulate osteoblast differentiation, *Bone.* 84: 262-270 (2016).
Dubowchik et al., Receptor-mediated and enzyme-dependent targeting of cytotoxic anticancer drugs, *Pharmacol. Ther.* 83:67-123 (1999).
Dumont, IL-17 cytokine/receptor families: emerging targets for the modulation of inflammatory responses, *Expert Opin. Ther. Patents.* 13:287-303 (2003).
Eyckmans et al., Mapping calcium phosphate activated gene networks as a strategy for targeted osteoinduction of human progenitors, *Biomaterials.* 34:4612-4621 (2013).
"FDA approves new psoriasis drug Cosentyx", FDA News Release, Jan. 21, 2015. pp. 1-3.
Fossiez et al., "Interleukin-17", *Int. Rev. Immunol.* 16:541-551 (1998).
Gaffen, An Overview of IL-17 Function and Signaling, *Cytokine.* 43: 402-407 (2008).
Genbank Accession No. Q16552, Interleukin-17A (precursor), Feb. 13, 2019.
Genbank Accession No. Q96PD4, Interleukin-17F (precursor), Feb. 13, 2019.
Gladman et al., Clinical, radiological, and functional assessment in psoriatic arthritis: is it different from other inflammatory joint diseases, *Annuals of the Rheumatic Diseases.* 65 (Suppl. III): iii22-iii24 (2006).
Gladman et al., Psoriatic arthritis: epidemiology, clinical features, course, and outcome, *Annuals of the Rheumatic Diseases.* 64(Suppl II): ii14-ii17 (2005).
Glatt et al., Bimekizumab, a monoclonal antibody that inhibits both IL-17A and IL-17F, produces a profound response in both skin and joints: results of an early-phase, proof-of-concept study in psoriatic arthritis, *Annals of the Rheumatic Disease,* 75:95-96 (Abstract) (2016).
Glatt et al., [OP0108] Bimekizumab, a monoclonal antibody that inhibits both IL-17A and IL-17F, produces a profound response in both skin and joints: results of an early-phase, proof-of-concept study in psoriatic arthritis, Annual European Congress of Rheumatology London, United Kingdom, Jun. 8-11, 2016, pp. 1-2.
Glatt et al., Bimekizumab, a monoclonal antibody that inhibits both IL-17A and IL-17F, produces a profound response in both skin and joints: results of an early-phase, proof-of-concept study in psoriatic arthritis, EULAR, London, UK (2016).
Glatt et al., Dual IL-17A and IL-17F neutralisation by bimekizumab in psoriatic arthritis: evidence from preclinical experiments and a

(56) References Cited

OTHER PUBLICATIONS randomised placebo-controlled clinical trial that IL-17F contributes to human chronic tissue inflammation, *Ann. Rheum. Dis.* 77:523-32 (2018).
Glatt et al., First-in-human IL-17A and IL-17F blockade with bimekizumab in patients with mild-to-moderate psoriasis: results of a randomized, placebo-controlled, single-dose-escalating study, AAD, Washington, D.C., USA, (Abstract) (2016).
Glatt et al., First-in-human IL-17A and IL-17F blockade with bimekizumab in subjects with mild-to-moderate psoriasis: results of a randomized, placebo-controlled, single-dose-escalating study, AAD, Washington, USA, (2016).
Glatt et al., First-in-human randomized study of bimekizumab, a humanized monoclonal antibody and selective dual inhibitor of IL-17A and IL-17F, in mild psoriasis, *Br. J. Clin. Pharmacol.* 83:991-1001 (2017).
Glottieb et al. Secukinumab, A Human Anti-Interleukin-17A Monoclonal Antibody, Significantly Reduces Psoriasis Burden in Patients with Psoriatic Arthritis: Results from a Phase 3 Randomized Controlled Trial, *Arthritis Rheum.* 66(Suppl 11):S233 (2014).
Haddad et al., Minimal Disease Activity and Anti-Tumor Necrosis Factor Therapy in Psoriatic Arthritis, *Arthritis Care Res.* 67:842-847 (2015).
Harris, Processing of C-terminal lysine and arginine residues of proteins isolated from mammalian cell culture, *J. Chromatogr. A.* 705:129-34 (1995).
Hellstrom et al., Controlled Drug Delivery, pp. 623-653 (2nd ed. 1987).
Hieter et al., Evolution of Human Immunoglobulin k J Region Genes, *J. Biol. Chem.* 257:1516-1522 (1982).
Holliger et al., Engineered antibody fragments and the rise of single domains, *Nat. Biotechnol.* 23:1126-36 (2005).
Hot et al., IL-17A- versus IL-17F-induced intracellular signal transduction pathways and modulation by IL-17RA and IL-17RC RNA interference in rheumatoid synoviocytes, *Ann. Rheum. Dis.* 70:341-8 (2011).
Huang et al., IL-17 stimulates the proliferation and differentiation of human mesenchymal stem cells: implications for bone remodeling, *Cell Death Differ.* 16:1332-1343 (2009).
Hueber et al., Effects of AIN457, a fully human antibody to interleukin-17A, on psoriasis, rheumatoid arthritis, and uveitis, *Sci. Transl. Med.* 2:52ra72 (2010).
Husted et al., Health-Related Quality of Life of Patients With Psoriatic Arthritis: A Comparison With Patients With Rheumatoid Arthritis, *Arthritis Care and Research.* 45:151-158 (2001).
Hymowitz, et al., IL-17s adopt a cysteine knot fold: structure and activity of a novel cytokine, IL-17F, and implications for receptor binding, *EMBO J.* 20:5332-5341 (2001).
International Preliminary Reporton Patentability, PCT/EP2016/075821 (dated May 1, 2018).
International Search Report and Written Opinion, PCT/EP2016/075821 (dated Mar. 31, 2017).
Iwakura et al., The IL-23/IL-17 axis in inflammation, *J. Clin. Invest.* 16:1218-1222 (2006).
Johansen et al., Characterization of the interleukin-17 isoforms and receptors in lesional psoriatic skin, *Br. J. Dermatol.* 160:319-24 (2009).
Kashmiri et al., SDR grafting—a new approach to antibody humanization, *Methods.* 36:25-34 (2005).
Kavanaugh et al., Golimumab, a New Human Tumor Necrosis Factor ? Antibody, Administered Every Four Weeks as a Subcutaneous Injection in Psoriatic Arthritis, *Arthritis and Rheumatism.* 60:976-986 (2009).
Kettleborough et al., Isolation of tumor cell-specific single-chain Fv from immunized mice using phage-antibody libraries and the reconstruction of whole antibodies from these antibody fragments, *Eur. J. Immunol.* 24:952-8 (1994).
Kirkham et al., Interleukin-17A: a unique pathway in immune-mediated diseases: psoriasis, psoriatic arthritis and rheumatoid arthritis, *Immunology.* 141:133-42 (2014).
Kohler et al., Continuous cultures of fused cells secreting antibody of predefined specificity, *Nature.* 256:495-7 (1975).
Kolls et al., Interleukin-17 Family Members and Inflammation, *Immunity.* 21:467-476 (2004).
Kozbor et al., The production of monoclonal antibodies from human lymphocytes, *Immunol. Today.* 4:72-9 (1983).
Kuestner et al., Identification of the IL-17 Receptor Related Molecule IL-17RC as the Receptor for IL-17F, *Journal of Immunology.* 179:5462-5473 (2007).
Langley et al., Evaluating psoriasis with Psoriasis Area and Severity Index, Psoriasis Global Assessment, and Lattice System Physician's Global Assessment, *J. Am. Acad. Dermatol.* 51:563-9 (2004).
Langowski et al., IL-23 promotes tumour incidence and growth, *Nature.* 442:461-465 (2006).
Lebwohl et al., Phase 3 Studies Comparing Brodalumab with Ustekinumab in Psoriasis, *N. Engl. J. Med.* 373:1318-28 (2015).
Low et al., Mimicking somatic hypermutation: affinity maturation of antibodies displayed on bacteriophage using a bacterial mutator strain. *J. Mol. Biol.* 260:359-68 (1996).
Marks et al., By-passing immunization: building high affinity human antibodies by chain shuffling, *Biotechnology (NY).* 10:779-83 (1992).
McInnes et al., Secukinumab, a human anti-interleukin-17A monoclonal antibody, in patients with psoriatic arthritis (FUTURE 2): a randomized, double-bind, placebo-controlled, phase 3 trial, *Lancet.* 386:1137-1146 (2015).
McInnes et al., Efficacy and safety of ustekinumab in patients with active psoriatic arthritis: 1 year results of the phase 3, multicentre, double-blind, placebo-controlled PSUMMIT 1 trial, *Lancet.* 382:780-9 (2013).
Mease et al., Adalimumab for the Treatment of Patients with Moderately to Severely Active Psoriatic Arthritis, *Arthritis and Rheumatism.* 52:3279-89 (2005).
Mease et al., Brodalumab, an Anti-IL17RA Monoclonal Antibody, in Psoriatic Arthritis, *New Engl J Med.* 370:2295-2306 (2014).
Mease et al., Effect of certolizumab pegol on signs and symptoms in patients with psoriatic arthritis: 24-week results of a Phase 3 double-blind randomised placebo-controlled study (RAPID-PsA), *Ann Rheum Dis.* 73:48-55 (2014).
Mease, Inhibition of interleukin-17, interleukin-23 and the TH17 cell pathway in the treatment of psoriatic arthritis and psoriasis, *Curr. Opin. Rheumatol.* 27:127-33 (2015).
Mease, Psoriatic arthritis: update on pathophysiology, assessment and management, *Ann. Rheum. Dis.* 70(Suppl 1):i77-84 (2011).
Mease et al., Secukinumab, a Human Anti-Interleukin-17A Monoclonal Antibody, Improves Active Psoriatic Arthritis and Inhibits Radiographic Progression: Efficacy and Safety Data from a Phase 3 Randomized, Multicenter, Double-Blind, Placebo-Controlled Study, *Arthritis Rheum.* 66(Suppl 11):S423-S424 (2014).
Mease et al., Secukinumab Inhibition of Interleukin-17A in Patients with Psoriatic Arthritis, *New Engl J Med.* 373:1329-1339 (2015).
Milstein et al., Hybrid hybridomas and their use in immunohistochemistry, *Nature.* 305:537-539 (1983).
Miossec et al., Targeting IL-17 and TH17 cells in chronic inflammation, *Nat. Rev. Drug Discov.* 11:763-76 (2012).
Nam et al., T-Lymphocytes Enable Osteoblast Maturation via IL-17F during the Early Phase of Fracture Repair, *PLoS One.* 7:e40044 (2012).
Ogdie et al., Identification of Risk Factors for Psoriatic Arthritis: Scientific Opportunity Meets Clinical Need, *Arch. Dermatol.* 146:785-788 (2010).
Osta et al., Classical and paradoxical effects of TNF-α on bone homeostasis, *Frontiers in Immunology.* 5:1-9 (2014).
Patten et al., Applications of DNA shuffling to pharmaceuticals and vaccines, *urr. Opin. Biotechnol.* 8:724-33 (1997).
Pattison et al., Environmental risk factors for the development of psoriatic arthritis: results from a case-control study, *Ann. Rheum. Dis.* 67:672-6 (2008).
Persic et al., An integrated vector system for the eukaryotic expression of antibodies or their fragments after selection from phage display libraries, *Gene.* 187:9-18 (1997).
Picchianti-Diamani et al., Health-related quality of life and disability in patients with rheumatoid, early rheumatoid and early psoriatic arthritis treated with etanercept, *Qual. Life Res.* 19:821-826 (2010).

(56) References Cited

OTHER PUBLICATIONS

Ravetch et al., Structure of the human immunoglobulin mu locus: characterization of embryonic and rearranged J and D genes, *Cell.* 27:583-91 (1981).
Riechmann et al., Reshaping human antibodies for therapy, *Nature* 332:323-7 (1988).
Roberts et al., Enhancement of osteogenic gene expression for the differentiation of human periosteal derived cells, *Stem Cell Res.* 7:137-144 (2011).
Roberts et al., The combined bone forming capacity of human periosteal derived cells and calcium phosphates, *Biomaterials.* 32:4393-4405 (2011).
Russolillo et al., Obesity and psoriatic arthritis: from pathogenesis to clinical outcome and management, *J. Rheumatol.* 52:62-67 (2013).
Salvarani et al., Clinical features and epidemiology of spondyloarthritides associated with inflammatory bowel disease, *World J. Gastroenterol.* 15:2449-2455 (2009).
Schett et al., Structural damage in rheumatoid arthritis, psoriatic arthritis, and ankylosing spondylitis: traditional views, novel insights gained from TNF blockade, and concepts for the future, *Arthritis Research and Therapy.* 13 Suppl. 1: S4 (2011).
Schoonjans et al., A new model for intermediate molecular weight recombinant bispecific and trispecific antibodies by efficient heterodimerization of single chain variable domains through fusion to a Fab-chain, *Biomolecular Engineering.* 17:193-202 (2001).
Shbeeb et al., The epidemiology of psoriatic arthritis in Olmsted County, Minnesota, USA, 1982-1991, *J. Rheumatol.* 27:1247-50 (2000).
Sritheran et al., Making the next steps in psoriatic arthritis management: current status and future directions, *Ther. Adv. Musculoskel. Dis.* 7:173-186 (2015).
Thompson et al., Affinity Maturation of a High-affinity Human Monoclonal Antibody Against the Third Hypervariable Loop of Human Immunodeficiency Virus: Use of Phage Display to Improve Affinity and Broaden Strain Reactivity, *J. Mol. Biol.* 256:77-88 (1996).
Thorpe et al., The preparation and cytotoxic properties of antibody-toxin conjugates, *Immunol. Rev.* 62:119-58 (1982).
Toy et al., Cutting Edge: Interleukin 17 Signals through a Heteromeric Receptor Complex, *J. Immunol.* 177:36-39 (2006).
Traunecker et al., Bispecific single chain molecules (Janusins) target cytotoxic lymphocytes on HIV infected cells, *EMBO J.* 10:3655-3659 (1991).
"UCB's bimekizumb demonstrates positive results in early development in patients with psoriatic arthritis," EULAR, Jun. 10, 2016.
Van Baarsen et al., Heterogeneous expression pattern of interleukin 17A (IL-17A), IL-17F and their receptors in synovium of rheumatoid arthritis, psoriatic arthritis and osteoarthritis: possible explanation for nonresponse to anti-IL-17 therapy, *Arthritis Res. Ther.* 16:426 (2014).
Vaughan et al., Human antibodies by design, *Nat. Biotechnol.* 16:535-9 (1998).
Verma et al., Antibody engineering: comparison of bacterial, yeast, insect and mammalian expression systems, *Journal of Immunological Methods.* 216:165-181 (1998).
Von Heinje, Sequence Analysis in Molecular Biology, Academic Press (1987).
Watanabe et al., Functional characterization of IL-17F as a selective neutrophil attractant in psoriasis, *J. Invest. Dermatol.* 129:650-6 (2009).
Weaver et al., Th17: An Effector CD4 T Cell Lineage with Regulatory T Cell Ties, *Immunity.* 24:677-688 (2006).
Weger, Current status and new developments in the treatment of psoriasis and psoriatic arthritis with biological agents, *Br. J. Pharmacol.* 160:810-20 (2010).
Wolff et al., Monoclonal Antibody Homodimers: Enhanced Antitumor Activity in Nude Mice, *Cancer Res.* 53:2560-2565 (1993).
Wright et al., The Human IL-17/IL-17A Heterodimeric Cytokine Signals through the IL-17RA/IL-17RC Receptor Complex, *J. Immunol.* 181:2799-2805 (2008).
Yang et al., CDR walking mutagenesis for the affinity maturation of a potent human anti-HIV-1 antibody into the picomolar range, *J. Mol. Biol.* 254:392-403 (1995).
Yao et al., Molecular characterization of the human interleukin (I L)-17 receptor, *Cytokine.* 9:794-800(1997).
Carlin et al., A 50% reduction in the Psoriasis Area and Severity Index (PASI 50)is a clinically significant endpoint in the assessment of psoriasis. *J. Amer. Acad. Dermatol.*, 50(6):859-66 (Jun. 2004).
Mease et al., Managing Patients with Psoriatic Disease: The Diagnosis and Pharmacologic Treatment of Psoriatic Arthritis in Patients with Psoriasis. *Drugs*, 74(4):423-41 (Feb. 2014).
Mease et al., Measures of psoriatic arthritis: Tender and Swollen Joint Assessment, Psoriasis Area and Severity Index (PASI), Nail Psoriasis Severity, *Arth. Care & Res.*, 63(11):S64-85 (Nov. 2011).
Strober et al., "Secukinumab improves patient-reported psoriasis symptoms of itching, pain, and scaling: results of two phase 3, randomized, placebo-controlled clinical trials", International Journal of Dermatology, 55(4): 401-407, Feb. 11, 2016.
Armstrong et al., "Assessing the overall benefit of a medication: cumulative benefit of secukinumab over time in patients with moderate-to-severe plaque psoriasis", Journal of Dermatological Treatment, 28(3): 200-205, Aug. 19, 2016.
Van de Kerkhof et al., Secukinumab long-term safety experience: A pooled analysis of 10 phase II and III clinical studies in patients with moderate to serve plaque psoris, J Am Acad Dermatol, 75(1) 83-98, May 12, 2016.

\* cited by examiner

Figure 1: Nucleotide and Amino Acid Sequences

CDRH1: GFTFSDYNMA (SEQ ID NO:1)
CDRH2: TITYEGRNTYYRDSVKG (SEQ ID NO:2)
CDRH3: PPQYYEGSIYRLWFAH (SEQ ID NO:3)
CDRL1: RADESVTTLMH (SEQ ID NO:4)
CDRL2: LVSNRES (SEQ ID NO:5)
CDRL3: QQTWSDPWT (SEQ ID NO:6)

CDRL1 for CA028 496.g3: RADESVRTLHM (SEQ ID NO:7)
CDRL2 for CA028 496.g3: LVSNSEI (SEQ ID NO:8)

Light Chain variable region of antibody CA028 496 (gL7) (SEQ ID NO:9)
AIQLTQSPSSLSASVGDRVTITCRADESVTTLMHWYQQKPGKAPKLLIYLVSNRESGVPSRFSGSGSGTDFTLTISSLQPEDFATYYCQQTWSDPWTFGQ
GTKVEIKR Light Chain variable region of antibody CA028 496.g3 (gL57) (SEQ ID NO:10)
AIQLTQSPSSLSASVGDRVTITCRADESVRTLMHWYQQKPGKAPKLLIYLVSNSEIGVPDRFSGSGSGTDFRLTISSLQPEDFATYYCQQTWSDPWTFGQ
GTKVEIK Heavy Chain variable region of antibody CA028 496 and CA028 496.g3 (gH9) (SEQ ID NO:11)
EVQLVESGGGLVQPGGSLRLSCAASGFTFSDYNMAWVRQAPGKGLEWVATITYEGRNTYYRDSVKGRFTISRDNAKNSLYLQMNSLRAEDTAVYYCASPP
QYYEGSIYRLWFAHWGQGTLVTVSS Light chain of antibody CA028 496 (without signal) (SEQ ID NO:12)
AIQLTQSPSSLSASVGDRVTITCRADESVTTLMHWYQQKPGKAPKLLIYLVSNRESGVPSRFSGSGSGTDFTLTISSLQPEDFATYYCQQTWSDPWTFGQ
GTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQG
LSSPVTKSFNRGEC Light chain of antibody CA028_496.g3 (without signal) (SEQ ID NO:13)
AIQLTQSPSSLSASVGDRVTITCRADESVRTLMHWYQQKPGKAPKLLIYLVSNSEIGVPDRFSGSGSGTDFRLTISSLQPEDFATYYCQQTWSDPWTFGQ
GTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQG
LSSPVTKSFNRGEC Light chain of antibody CA028_496.g3 including signal (SEQ ID NO:14)
MSVPTQVLGLLLLWLMLTDARCAIQLTQSPSSLSASVGDRVTITCRADESVRTLMHWYQQKPGKAPKLLIYLVSNSEIGVPDRFSGSGSGTDFRLTISSLQP
EDFATYYCQQTWSDPWTFGQGTKVEIKRTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC Heavy chain of antibody CA028_496 SEQ ID NO:15
EVQLVESGGGLVQPGGSLRLSCAASGFTFSDYNMAWVRQAPGKGLEWVATITYEGRNTYYRDSVKGRFTISRDNAKNSLYLQMNSLRAEDTAVYYCASPP
QYYEGSIYRLMFAHWGQGTLVTVSSASTKGPSVFPLAPCSRSTSESTAALGCLVKDYFPEPVTVSWNSGALTSGVHTFPAVLQSSGLYSLSSVVTVPSSS
LGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLGK Heavy chain of antibody CA028_496.g3 (without signal) (SEQ ID NO:16)
EVQLVESGGGLVQPGGSLRLSCAASGFTFSDYNMAWVRQAPGKGLEWVATITYEGRNTYYRDSVKGRFTISRDNAKNSLYLQMNSLRAEDTAVYYCASPP
QYYEGSIYRLMFAHWGQGTLVTVSSASTKGPSVFPLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK Heavy chain of antibody CA028_496.g3 including signal (SEQ ID NO:17)
MEWSWVFLFFLSVTTGVHSEVQLVESGGGLVQPGGSLRLSCAASGFTFSDYNMAWVRQAPGKGLEWVATITYEGRNTYYRDSVKGRFTISRDNAKNSLYL
QMNSLRAEDTAVYYCASPPQYYEGSIYRLMFAHWGQGTLVTVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFY
PSDIAVEWESNGQPENNYKTTPPVLDSDGSFFLYSKLTVDKSRWQQGNVFSCSVMHEALHNHYTQKSLSLSPGK

Figure 1 (Continued)

DNA encoding Light Chain variable region of antibody CA028_496.g3 (SEQ ID NO:18)
gccatccagttgacccagagcccctctctcagcgcagtcgagacagagtgactattacctgcaggctgacgaaagcgtgagaacattgatgc
actggtaccaacagaagcctggcaaagcccccaagctcctgatctatctgtttccaattcggagattggagtcccgacagttggagtcagtggctc
tggaactgacttgcctgacaatctcctcactcagcccgaagatttgccacctactattgccgcagactgacgacccttggagacagcacttgtgacag
ggcacaaaagtggagatcaag DNA encoding Heavy Chain variable region of antibody CA028_496 and CA028_496.g3 (SEQ ID NO:19)
gaggttcagctcgttgaatccggaggcgtcgtgcagcctgggcctccttgcggctgacctgagctgcgtccagtggcttcacttttcagcgattacaata
tggcctgggtgcgccaggccccagggcaaggtctggagtgggtggccacaattacctatgagggcagaacacttattaccggattcagtgaaagggcg
attaccatcagcagggataatgcaaagaacagtctgtacctgcagatgaactctctgagagctgaggactgtattgtgtcaagccccaccc
cagtactatatgaggctcaatctacagattgtgtttgcccattgggccagggaacactgtgaccgtctcgagc DNA encoding light chain of antibody CA028_496 including signal sequence (SEQ ID NO:20)
Atgtcagttcccacacagtgctggctgcttctgttgtgctcaccgatgctagtgtgccatccagtcgacccagagcccttctctcagcgcca
gtgtcggagacagagtgactattacctgcaggctgacgaaagcgtgagaacattgatgactggtaccacagaagcctgcaaagccccagcctcct
gatctatctgtttccaatcggagtcccgacagttcagcggcagtggtctggaactgatcctgcgaactctgcgcatcagctcctcactccagccc
gaagatttgccacctactattgccgcagactgacgatcaagcgtagatcaagcgtacggtagcggcccat
ctgtctcatctttcgcatctgatgagcagttgaatctggaactgtcctcgttgttgtgcctgctgcttgataacttcatcccagaggcaagaccgtaca
gtggaaggtgataacgccctcaatgctacggcctgcgaagtctacgacctgcagcagcacgacggccctgacg
ctgagcaagcagactacgagaaaacacaaagtctacgcctgcgaagtctaacagaagagcttcaacagggagagt
gttag DNA encoding light chain of antibody CA028_496.g3 (no signal sequence) (SEQ ID NO:21)
gccatccagtcgacccagagcccttctctcagcgcagtcgagacagagtgactattacctgcaggctgacgaaagcgtgagaacattgatgc
actggtaccaacagaagcctggcaaagcccccaagctcctgatctatctgtttccaattcggagattggagtcccgacagttcagcggcagtggtc
tggaactgacttgcctgacaatctcctcactcagcccgaagatttgccacctactattgccgcagactgacgatcaagcagttgaactcctgttgtgt
ggcacaaaagtggagatcaagcgtacggcggccaaagtacagttgggaactgccctccaatcgtgatgagcagttgaagctcgtcagagagcagga
gcctgctgaataacttctctatcccagagaggactgcagcacctgccagcacgaccctgacgctgagcaaagcagactacgagaaacacaaagtctacgcc
tgcgaagtctcacaaagagcttcaacagggagagtgttag

Figure 1 (Continued)

DNA encoding light chain of antibody CA028_496.g3 including signal sequence (SEQ ID NO:22)
atgtcagttcccacacagtgctgggcctgctgcttctgtttgtgctcaccgatgctaggtgtgccatccagctgacccagagcccttcctcttctcagcgcca
gtgtcggagacagagtcactattacctgcagggctgacgaaagcgtgagaacattgatgcactgtaccaacaagaagcctgcgacaatctcctcactccagccc
gatctatctggtttccaattcggagattgcgagagcagagactgcgagcgacagacccctggaggctgcagtggtctgaactgacttttcgcctgacaatcagccc
gaagatttcgccacctactattgcccatcttccccgcatctgatgagcagtttgaactctgaaatctgaactgcctctgttgtgcctgctgaataacttctatcccagaggccaaagtaca
ctgtcttcatcttccccgcatctgatgagcagtttgaactctgaaatctgaactgcctctgttgtgcctgctgaataacttctatcccagaggccaaagtaca
gtggaaggtggataaccccctcaatgggtaactcggagagagtgtcacagagcagcaaggacagcagcacctacagcctcagcagcaccctgacg
ctgagcaaagcagactacgagaaacacaaagtctacgcctgcgaagtcacccatcaggctgagctgcccgtcacaaagagcttcaacaggggagagt
gttag DNA encoding heavy chain of antibody CA028_496 (including signal sequence) (SEQ ID NO:23)
atggaatggtcctggtctcttttccttctgtttttcctttctgtcacaaccggggtgcacagcgaggttcagctcgttgaatccgagcgagcgactcgtcagcctg
gggctccttgcggctcagctgcgctgccagtgcttcactttcagcgatacaatatgccgtggtgcgcaggccacagccaaggttctggagtgggt
ggccacaattacctatcgaggcagaacacttattaccgggattcagtgcaagcccaccagtactatgagggtcaatctacagattgtgttgccatt
cagtgaactctctgacagctgagactgcgtgactgcaaggctctcgagcgtctcgagcgttctacaagggccatccgtcttccccggcgccctgctccaggagcgcccctgacagcagcacagcagc
gcccaggagaacactgtgctgctgcaaggactactccctcagcagtcctctccccgacagcgtgtcgtcagcaggctggcacgacagcctacacctgcaacgtagatcacaagccca
ctacagtcctcaggactctcagcagcttcccgcagcggtgtgtccctcagcagcgtgtgctgcacgacagccagcgtctcagcttcctgcctgaagatcacaagccca
gcaacaccaaggtgacaagagtgttgtgagaggccagcacagaggagggtgtctgctggaaagcaggcagcctcagcccctcctgcctgaggagagggcttctg
gctgtgcagcccaggcagcgctctccggaccatgccgatgcctctctcaccggaggcctctgacaccaggcagtgtgcgctcagactcgcctgccaagagcca
gattttccaccaggctccgggcagcagccggtggcgtgtgcgaggcgccagaatgtgcccgcaggagtctcactctccactctcccccagtctgctcctgccaagatctgagtaact
tatccggagagcccctcagtccctgacctaagcaaacaaaactctccactccagctcagacaaccaggcctgcagacacctctgcctcagcaacagcaggtctgaactccagatctgagtaact
cccaatcttctctgcagagtccaaatatggtccccaggcccaggcctgctgacgtccctgaagcaaccaggcctgtgctgctcctcagcagcctgagttctgggggacatcag
gcctagtagcctgcattcccccaaaaccaaggacactctcatgatctccgagaccaagacaaagcgcggagagagcagttcaacagcacgtacgtggtgtgtcagcgtcctc
tcttcctgtccccccaaaaccaaggacactctcatgatctccgagaccaagacaaagcgcggagagagcagttcaacagcacgtacgtggtgtcagcgtcctc
ccagttcaactggtaccgtggagtgcgtgaaggtgcataatgccaaggagtacaagtgcaaggtctccaacaaagcctccgtcctccatcgagaaaaccatctccaaagcca
accgtcctgcaccaggactggctgaacggcagggagcctgccacccgggtactacaccctccccatccgggaggtgtgcctgacctgcctggtcaaaggcttctaccccagcgacatcgccg
aagtgggaccccacgggtgcgaggccaacatgaccaaaacccacgggtctgttctctgcgcctgcggactgcgacagagtgcacctgagaacaactaccagaaagaccagctcacccgtgctggactccgacggctccttcttcctctactac
gcagccccgagaacaactacaagaccacacctcccgtgctggactccgacggctccttcttcctctac
cagcagcatcgcctgtgcagtggacaaagagcaggtggcaggaggggaatgtcttctcatgctccgtgatgcatgaggctctgcacaaccactacacagaagagcc
tctccctgtctctgggtaaa

Figure 1 (Continued)

DNA encoding heavy chain of antibody CA028_496.g3 (including exons but without signal sequence) (SEQ ID NO:24)

gaggttcagctcgttgaatccgagcggactcgtgcagcctggggggctccttgcgctgagctgcctgccagtggcttcactttcagcgattacaata
tggcctgggtgcgccaggcccaaggtctggagtgggtggccacaattacctattgagggcagaaacacttattaccggattcagtgaaagggcg
attaccatcagcaggatataatctcaagaacagtctgtatttgcaaatgaactctctgagagctgaggacactgtgtactattgtgcaagccaccc
cagtactactagggctcaatctacagattgtgtttgcccattggggccaagggacactctggtcaccgtctcctcagcctccaccaagggccccatcggtct
tccccctggcacccctcctccaagagcacctctgggggcacagcggccctgggctgcctggtcaaggactacttccccgaaccggtgacggtgtcgtggaa
ctcaggcgccctgaccagcggcgtgcacaccttcccggctgtcctacagtcctcaggactctactcccttcagcagcgtggtgaccgtgccctccagcagc
ttgggcacccagacctacatctgcaacgtgaatcacaagcccagcaacaccaaggtggacaagaaagttgagcccaaatcttgtgacaaaactcacacat
gcccaccgtgcccagcacctgaactcctggggggaccgtcagtcttcctcttccccccaaaacccaaggacaccctcatgatctcccggacccctgaggt
cacatgcgtggtggtggacgtgagccacgaagaccctgaggtcaagttcaactggtacgtggacggcgtggaggtgcataatgccaagacaaagccgcgg
gaggagcagtacaacagcacgtaccgtgtggtcagcgtcctcaccgtcctgcaccaggactggctgaatggcaaggagtacaagtgcaaggtctccaaca
aagccctcccagcccccatcgagaaaaccatctccaaagccaaagggcagccccgagaaccacaggtgtacaccctgcccccatcccgggatgagctgac
caagaaccaggtcagcctgacctgcctggtcaaaggcttctatcccagcgacatcgccgtggagtgggagagcaatgggcagccggagaacaactacaag
accacgcctcccgtgctggactccgacggctccttcttcctctacagcaagctcaccgtggacaagagcaggtggcagcaggggaacgtcttctcatgct
ccgtgatgcatgaggctctgcacaaccactacacgcagaagagcctctccctgtctccgggtaaa DNA encoding heavy chain of antibody CA028_496.g3 (including signal sequence and exons) (SEQ ID NO:25)

atggaatggtcctgggtctttctgtttttccttttgtcacaaccggggtgcacagcgaggttcagctcgttgaatccgaggcggactcgtgcagcctg
gggggctccttgcgctgagctgcctgccagtggcttcactttcagcgattacaatatggcctgggtgcgccaggcccaaggtctggagtgggtggt
ggccacaattacctattgagggcagaaacacttattaccggattcagtgaaagggcgattaccatcagcaggatataatctcaagaacagtctgtacctg
cagtgaactctctgagagctgaggacactgtgtactattgtgcaagccaccccagtactactagggctcaatctacagattgtgtttgcccatt
ggggccaagggacactctggtcaccgtctcctcagcctccaccaagggcccatcggtcttccccctggcaccctcctccaagagcacctctgggggcacagc
ggccctgggctgcctggtcaaggactacttccccgaaccggtgacggtgtcgtggaactcaggcgccctgaccagcggcgtgcacaccttcccggctgtc
ctacagtcctcaggactctactccctcagcagcgtggtgaccgtgccctccagcagcttgggcacccagacctacatctgcaacgtgaatcacaagccca
gcaacaccaaggtggacaagaaagttgagcccaaatcttgtgacaaaactcacacatgcccaccgtgcccagcacctgaactcctggggggaccgtcagt
cttcctcttccccccaaaacccaaggacaccctcatgatctcccggacccctgaggtcacatgcgtggtggtggacgtgagccacgaagaccctgaggtc
aagttcaactggtacgtggacggcgtggaggtgcataatgccaagacaaagccgcgggaggagcagtacaacagcacgtaccgtgtggtcagcgtcctca
ccgtcctgcaccaggactggctgaatggcaaggagtacaagtgcaaggtctccaacaaagccctcccagcccccatcgagaaaaccatctccaaagccaa
agggcagccccgagaaccacaggtgtacaccctgcccccatcccgggatgagctgaccaagaaccaggtcagcctgacctgcctggtcaaaggcttctat
cccagcgacatcgccgtggagtgggagagcaatgggcagccggagaacaactacaagaccacgcctcccgtgctggactccgacggctccttcttcctct
acagcaagctcaccgtggacaagagcaggtggcagcaggggaacgtcttctcatgctccgtgatgcatgaggctctgcacaaccactacacgcagaagag
cctctccctgtctccgggtaaa

Figure 1 (Continued)

cDNA encoding heavy chain of antibody CA028_496.g3 (including signal sequence) (SEQ ID NO:26)
atggaatggtcctggtcttcctgttttcctttctgtcacaaccggggtgcacagcgaggttcagctcgttgaatccgaggcgactcgtgcagcctg
ggggctccttgcggctgcgctgagctgcgctgccagtggcttcacttcagcgattcagtcagatgcctggttgcgccaggcaaggtctggagtgggt
ggccacaattacctatgagggcagaaacactattaccggattcagtgaagggcgattaccatcagcaggatcaatctacagattgtggtttgcccatt
cagatgaactctctgagagctgaggacactgtgtattactgtgcaagggcccatcggtcttccccctgaccgtactactagagacacctctgggccacagc
ggggccaggaacactggtgaccgtctcaaggactacttcccgaacagcagggcggtgtcgtgcctccagcagcttggcaccaccgtgaatcacaagccca
ggcctgggctgcctcaggactctactcctcagcagcggtgtgaccgtgcctccagcagcttggcaccaccgtgaatcacaagccca
ctacagtcctcaggactctactcctcagcagcggtgtgaccgtgcctccagcagcttggcaccatctgaactcctggggggaccgtcagt
gcaacaccaagtcgacaagaaagttgagccacacacccaaatctttgtgacaaactcacacacacacacacacacacacctgaactcctggggggaccgtcagt
cttcctcttcccccaaaaacccaaggacacccctcatgatctcccgacacacaagccgcggagagcagtgcaacagcacgtaccgtgtgtcagcgtcctca
aagttcaactgtacgtggacggcgtggaagtgcataatgcaagacacagcccccgggagagcagtgcaacagcacgtaccgtgtgtcagcgtcctca
ccgtcctgcaccaggactgcgtgaatgcaagtacacaccctgccccatcgagaaaaccatctcaaagccaa
agcgcagccagcacagttgtacacccctgcccccatcgagaagtgcaagtacacaccctgccccatcgagaaaaccatctcaaagccaa
cccagccgcaaatcgccgtggagtggagagcaatggcagcgagagagcagtggcagcaggggaacgtcttctcagtcgtgatgcatgaggctctgcacaaccactacacgcagaagag
acagcaagtcaccgtggacaagagcaggtggcagcaggggaacgtcttctcagtcgtgatgcatgaggctctgcacaaccactacacgcagaagag
cctctccctgtctccgggtaaa Human IL-17A (SEQ ID NO:27)
GITIPRNPGCPNSEDKNFPRTVMVNLNIHNRNTNTNPKRSSDYYNRSTSPWNLHRNEDPERYPSVIWEAKCRHLGCINADGNVDYHMNSVPIQQEILVLR
REPPHCPNSFRLEKILVSVGCTCVTPIVHHVA Human IL-17F (SEQ ID NO:28)
RKIPKVGHTFFQKPESCPPVPGGSMKLDIGIINENQRVSMSRNIESRSTSPWNYTVTWDPNRYPSEVVQAQCRNLGCINAQGKEDISMNSVPIQQETLVV
RRKHQGCSVSFQLEKVLVTVGCTCVTPVIHHVQ

Figure 1 (Continued)

Figure 2: CASPAR criteria

Inflammatory articular disease (joint, spine, or entheseal) AND at least 3 points of the following 5 categories:

| Category | Definition | Points |
|---|---|---|
| 1) Evidence of psoriasis: (Score for 1 of the following<sup>a</sup>) | | |
| Current psoriasis | Psoriatic skin or scalp disease present today as judged by a dermatologist or rheumatologist | 2 points |
| Personal history of psoriasis | A history of psoriasis that may be obtained from the subject, family physician, dermatologist, rheumatologist, or other qualified health care provider | 1 point |
| Family history of psoriasis | A history of psoriasis in a first- or second-degree relative according to subject report | 1 point |
| 2) Psoriatic nail dystrophy | Typical psoriatic nail dystrophy, including onycholysis, pitting, and hyperkeratosis, observed on current physical examination | 1 point |
| 3) A negative test for rheumatoid factor | By any method except latex, but preferably by enzyme-linked immunosorbent assay (ELISA) or nephelometry, according to the local laboratory reference range | 1 point |
| 4) Dactylitis: (Score for 1 of the following) | | |
| Current dactylitis | Swelling of an entire digit | 1 point |
| History of dactylitis | A history of dactylitis recorded by a rheumatologist | 1 point |
| 5) Radiologic evidence of juxta-articular new bone formation | Ill-defined ossification near joint margins (but excluding osteophyte formation) on plain radiographs of the hand or foot | 1 point |

CASPAR=Classification Criteria for Psoriatic Arthritis
<sup>a</sup> "Score for 1 of the following" means that only 1 of the 3 criteria is applicable (either current psoriasis [scores 2 points], personal history [scores 1 point], or family history [scores 1 point]).

Figure 3a: PASI 50/75/90 response at week 8

| | Placebo | UCB4940 80mg/ 40mg/ 40mg | UCB4940 160mg/ 80mg/ 80mg | UCB4940 240mg/ 160mg/ 160mg | UCB4940 560mg/ 320mg/ 320mg | UCB4940 Combined 3 top doses group |
|---|---|---|---|---|---|---|
| Subjects with BSA ≥ 3% psoriasis n (%) | 5 (50%) | 2 (50%) | 4 (67%) | 9 (60%) | 2 (40%) | 15 (58%) |
| PASI50 n (%) [95% CI] | 1 (20%) [4% - 62%] | 2 (100%) [34% - 100%] | 4 (100%) [51% - 100%] | 9 (100%) [70% - 100%] | 2 (100%) [34% - 100%] | 15 (100%) [80% - 100%] |
| PASI75 n (%) [95% CI] | 0 [0% - 43%] | 1 (50%) [10% - 91%] | 4 (100%) [51% - 100%] | 9 (100%) [70% - 100%] | 2 (100%) [34% - 100%] | 15 (100%) [80% - 100%] |
| PASI90 n (%) [95% CI] | 0 [0% - 43%] | 1 (50%) [10% - 91%] | 4 (100%) [51% - 100%] | 8 (89%) [57% - 98%] | 1 (50%) [10% - 91%] | 13 (87%) [62% - 96%] |

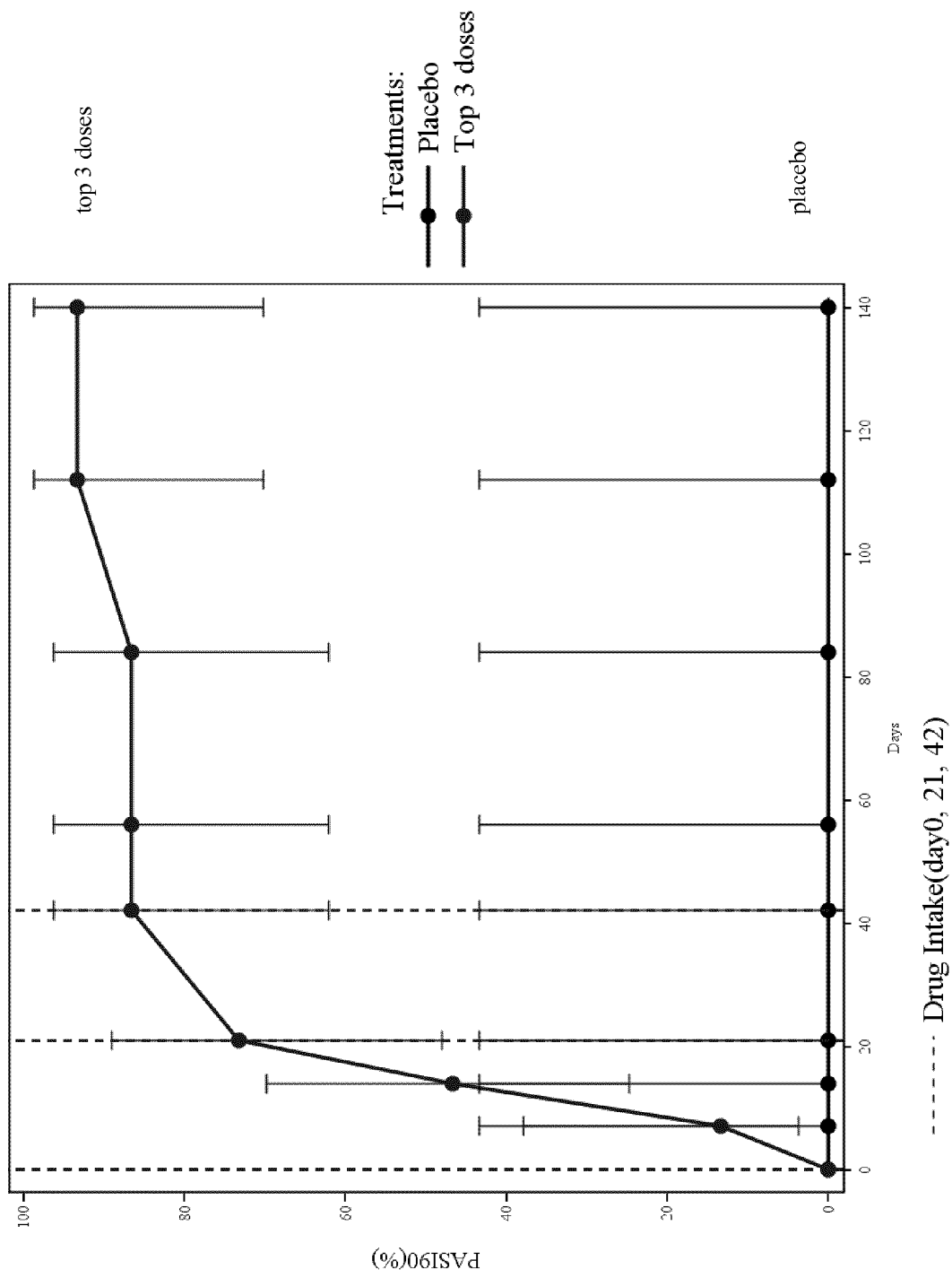
Figure 3b: Time course of PASI 90-response (PA0007) from first dose(day 0) to day 140 (week 20)

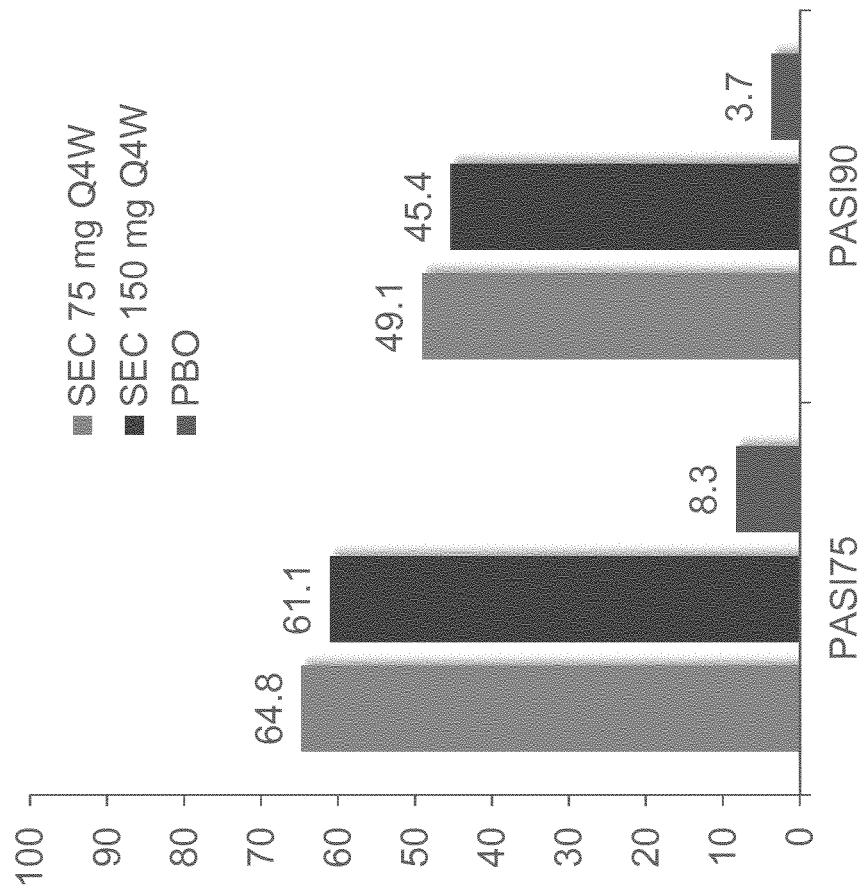
Figure 4: Secukinumab Future 1 Results: PASI (week 24)

Figure 5a: ACR20/50/70 response at week 8

| | Placebo (N=12) | UCB4940 80mg/ 40mg/ 40mg (N=6) | UCB4940 160mg/ 80mg/ 80mg (N=6) | UCB4940 240mg/ 160mg/ 160mg (N=19) | UCB4940 560mg/ 320mg/ 320mg (N=5) | UCB4940 Combined 3 top doses group (N=30) |
|---|---|---|---|---|---|---|
| ACR20 n (%) [95% CI] | 2 (17%) [5% - 45%] | 3 (50%) [19% - 81%] | 5 (83%) [44% - 97%] | 15 (79%) [57% - 92%] | 4 (80%) [38% - 96%] | 24 (80%) [63% - 91%] |
| ACR50 n (%) [95% CI] | 1 (8%) [2% - 35%] | 1 (17%) [3% - 56%] | 3 (50%) [19% - 81%] | 7 (37%) [19% - 59%] | 2 (40%) [12% - 77%] | 12 (40%) [25% - 58%] |
| ACR70 n (%) [95% CI] | 0 [0% - 24%] | 0 [0% - 39%] | 0 [0% - 39%] | 5 (26%) [12% - 49%] | 2 (40%) [12% - 77%] | 7 (23%) [12% - 41%] |

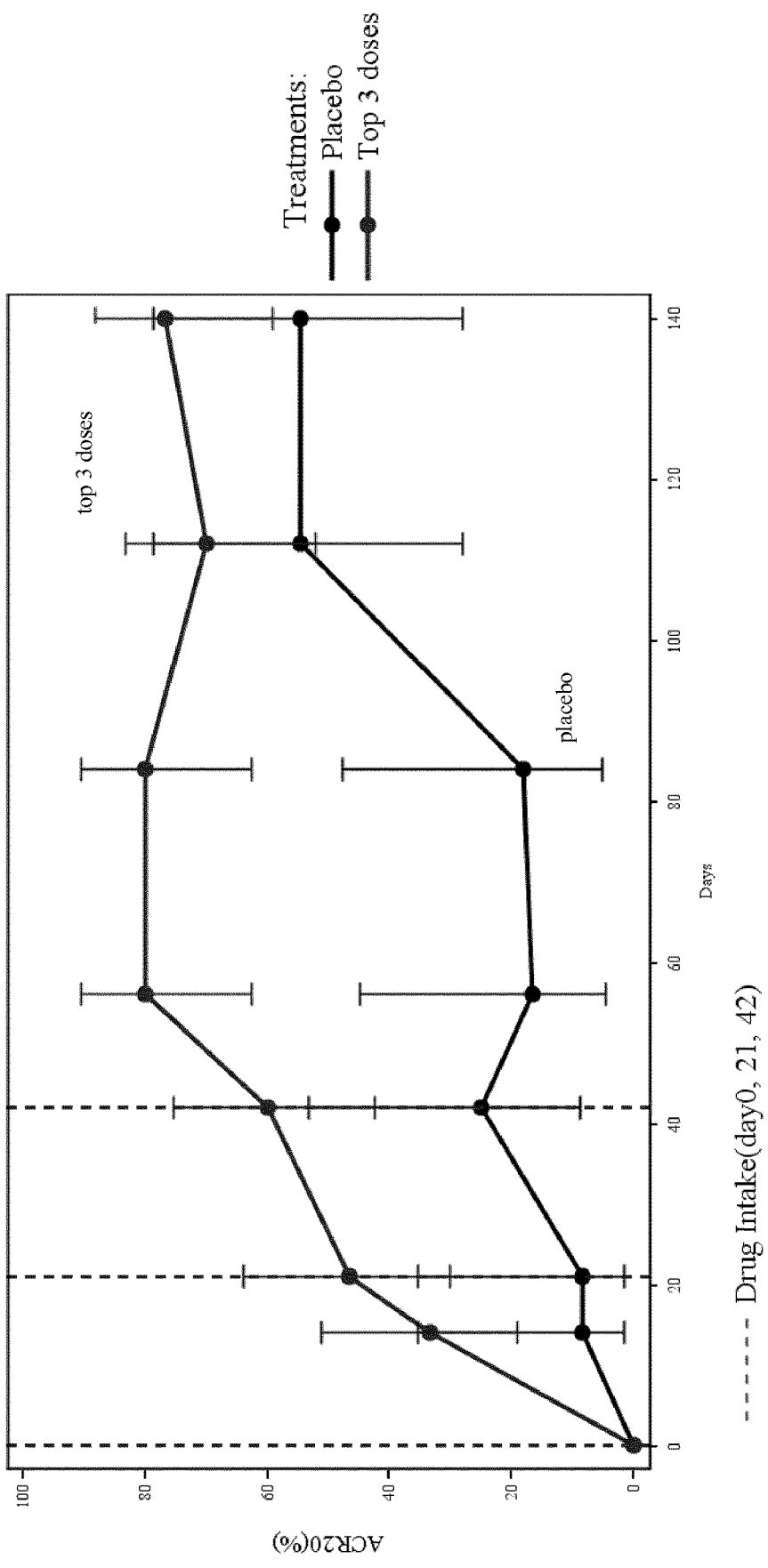
Figure 5b: Summary Plot of the ACR20 response rates from PA0007 from start of study (day 0) to day 140 (week 20).

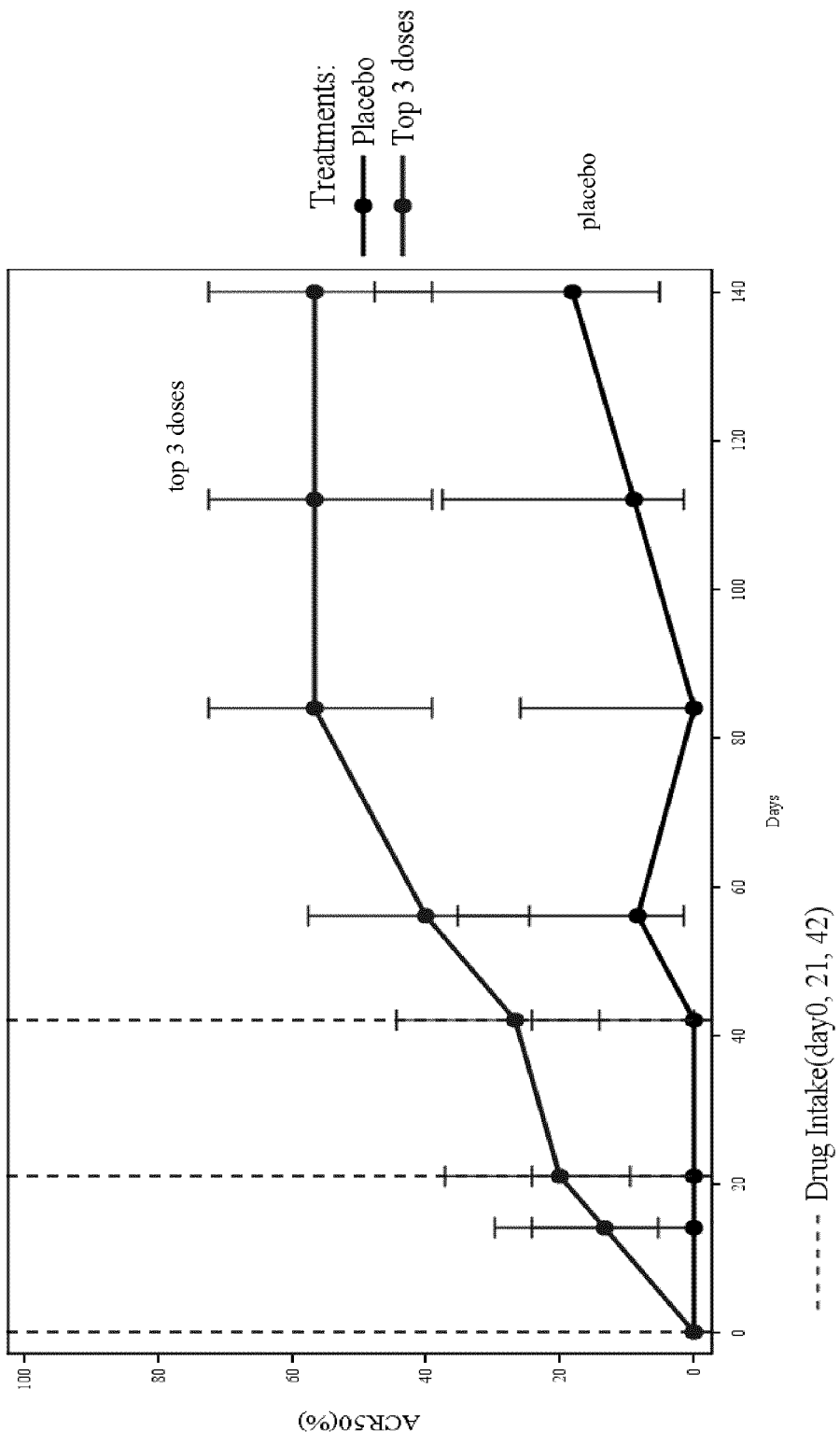
Figure 5c: Summary Plot of the ACR50 response rates from PA0007 from start of study (day 0) to day 140 (week 20).

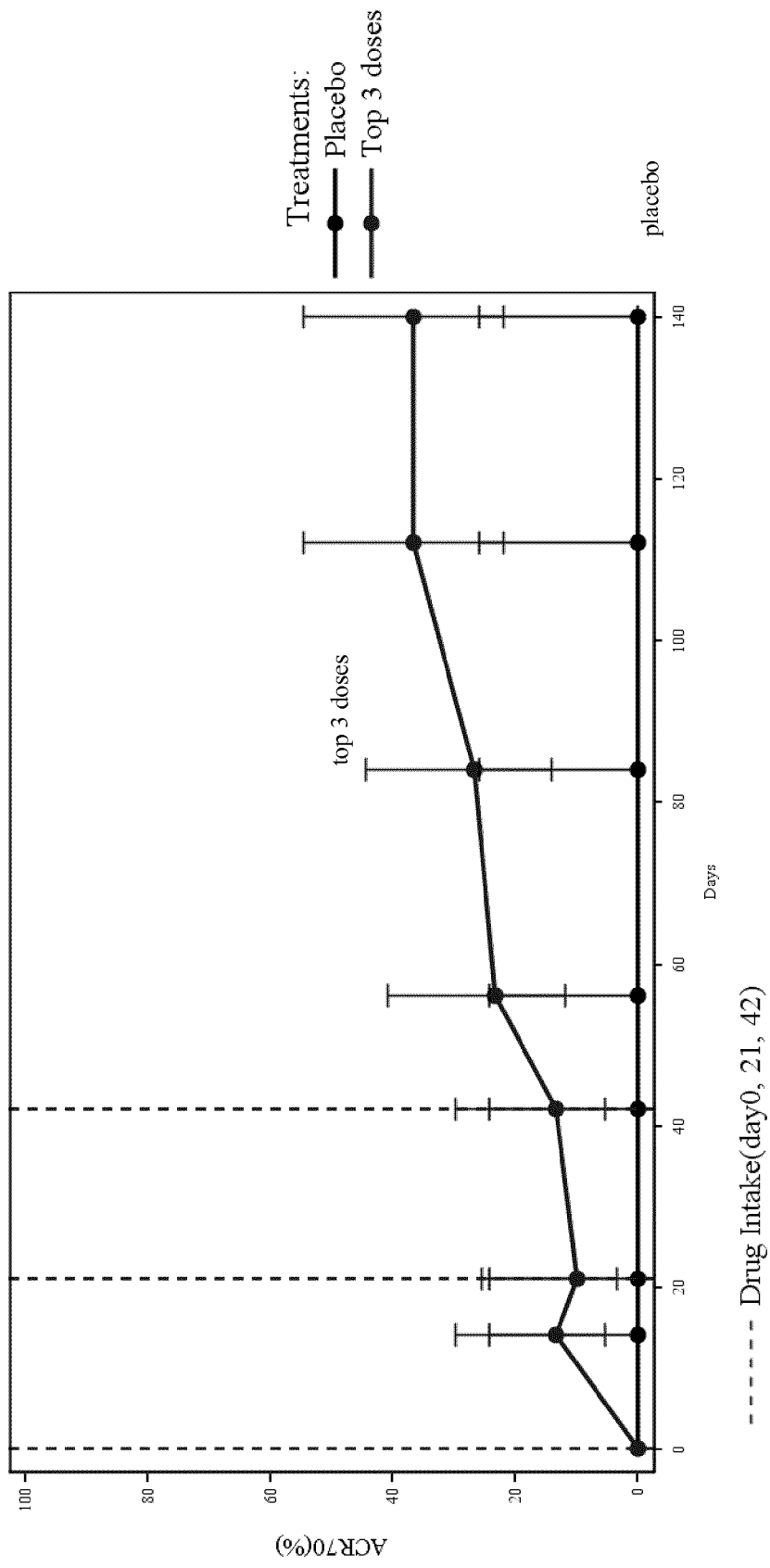
Figure 5d: Summary Plot of the ACR70 response rates from PA0007 from start of study (day 0) to day 140 (week 20).

Figure 6: Secukinumab Future 1 Results and Cimzia RAPID-PsA Results: ACR20
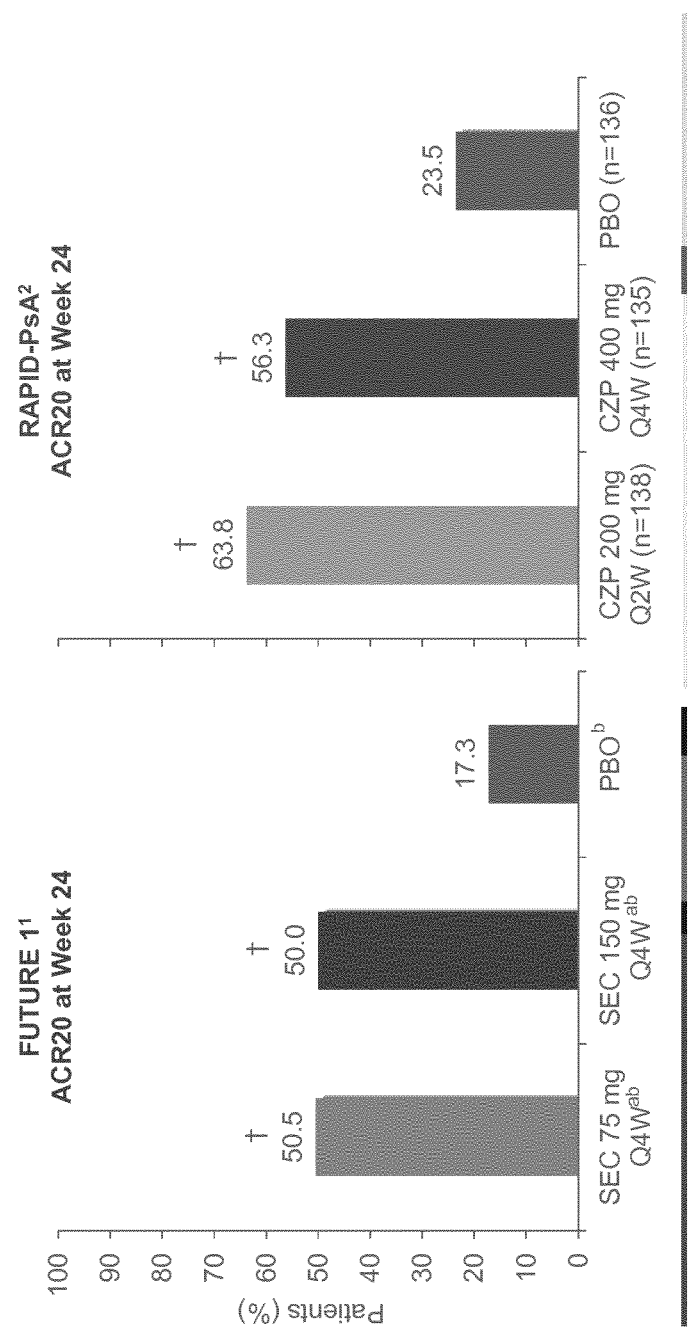

Figure 7: Summary Table of Bayesian Analysis

| Dose Group | N | Observed ACR20 | Estimated ACR20 | Credible Intervals | |
|---|---|---|---|---|---|
| | | | | 95% | 99% |
| Placebo | 12 | 16.7% | 22% | 12% - 36% | 9% - 41% |
| Pooled top doses | 30 | 80.0% | 81% | 64% - 92% | 59% - 94% |

Figure 8: Summary Table of ACR20 response at week 8 in psoriatic arthritis for registered anti-TNFs or Phase III results. Observed ACR20 response rates for registered Anti-TNF's at Week 8 when administered at registered doses

| Drug name (Active ingredient) | Active | Placebo | Δ (Difference between active and placebo) | Reference |
|---|---|---|---|---|
| | | ANTI-TNF's | | |
| Humira (Adalimumab) | 56.7 | 11.6 | 45.1 | (1) |
| Simponi (Golimumab) | 43.5 | 8.3 | 35.2 | (2) |
| Cimzia (Cetrolizumab Pegol) | 49.4 | 22.3 | 27.1 | (3) |
| | | ANTI-IL17's | | |
| Cosentyx (Secukinumab) | 59.73 | 21.25 | 38.5 | (4) |
| | | ANTI-IL12/23 | | |
| Stelara (Ustekinumab) | 33.34 | 20.83 | 12.51 | (5) |

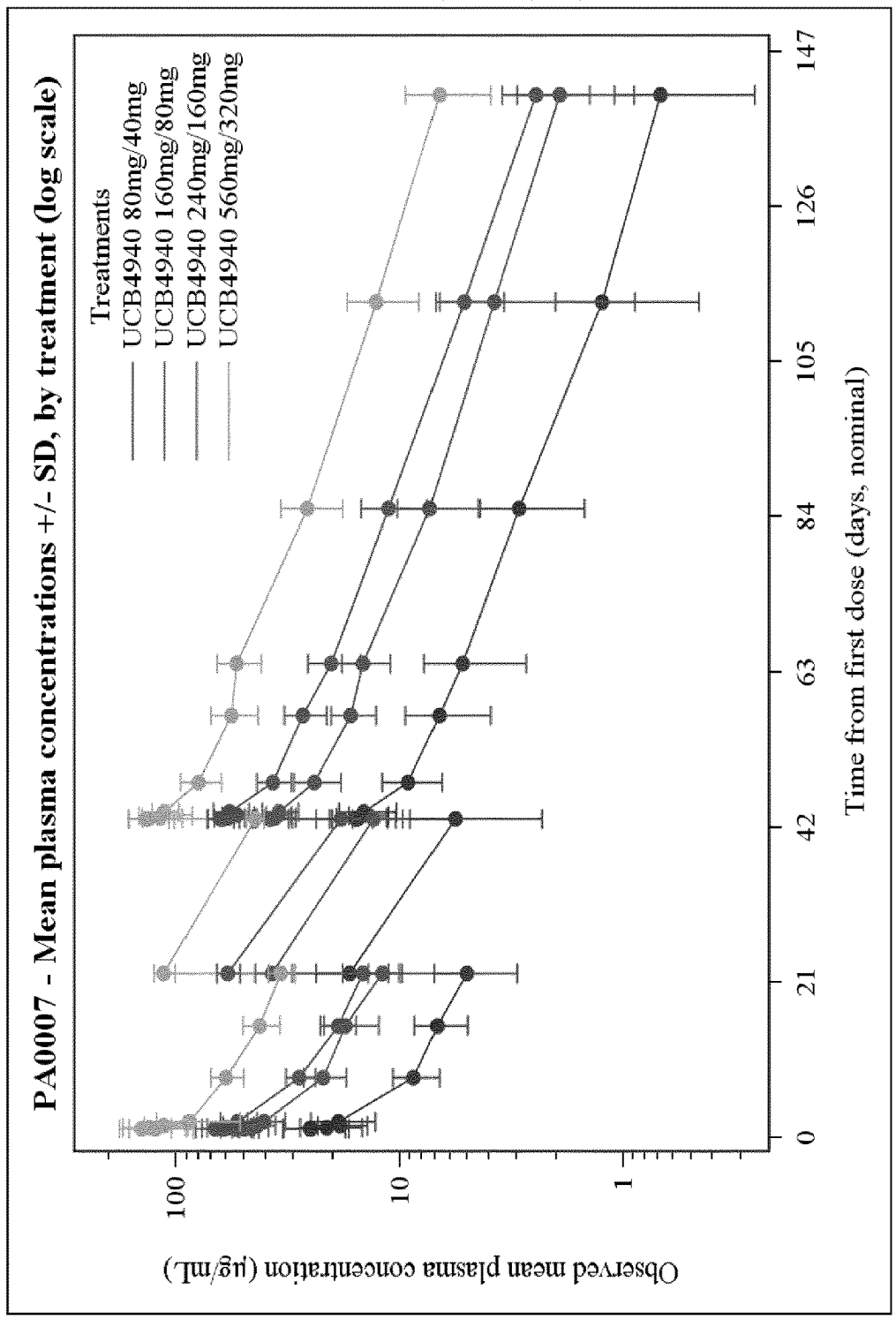
Figure 9: Targeted UCB4940 PK concentrations

Figure 9 continued

| | Week 0 | Week 3 | Week 6 | Czp (TBC) Trough |
|---|---|---|---|---|
| Group 1 | 240 mg | 160 mg | 160 mg | >20 ug/mL |
| Group 2 | 160 mg | 80 mg | 80 mg | > 10 ug/mL |
| Group 3 | 560 mg | 320 mg | 320 mg | > 40 ug/mL |
| Group 4 | 80 mg | 80 mg | 80 mg | < 10 ug/mL |

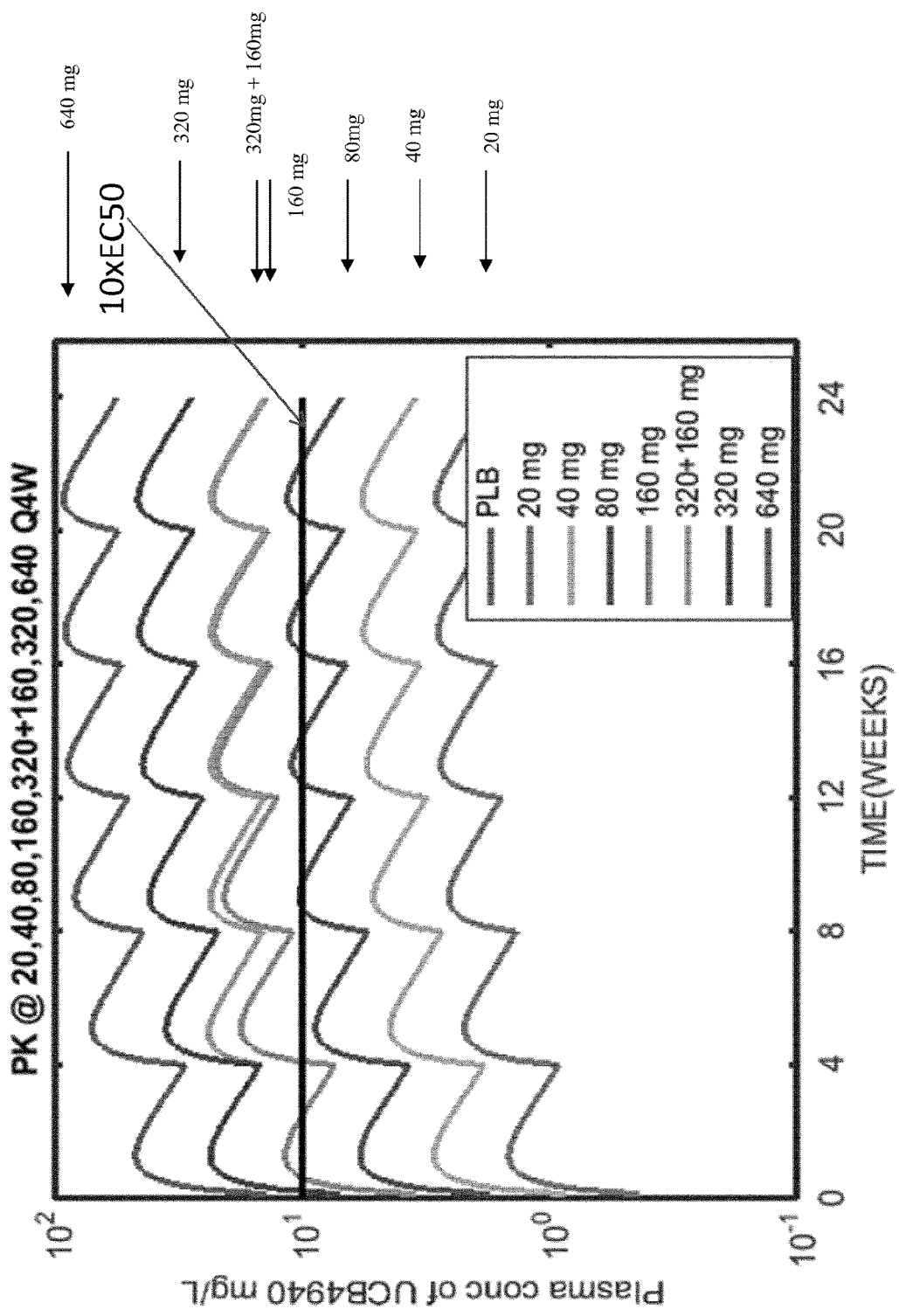
Figure 10: Summary PK plot of predicted SC dosing, illustrating that a dose of 320 loading followed by 160mg Q4W or 160 mg Q4W and higher, are able to achieve the plasma concentrations studied in PA0007 at the top 3 doses.

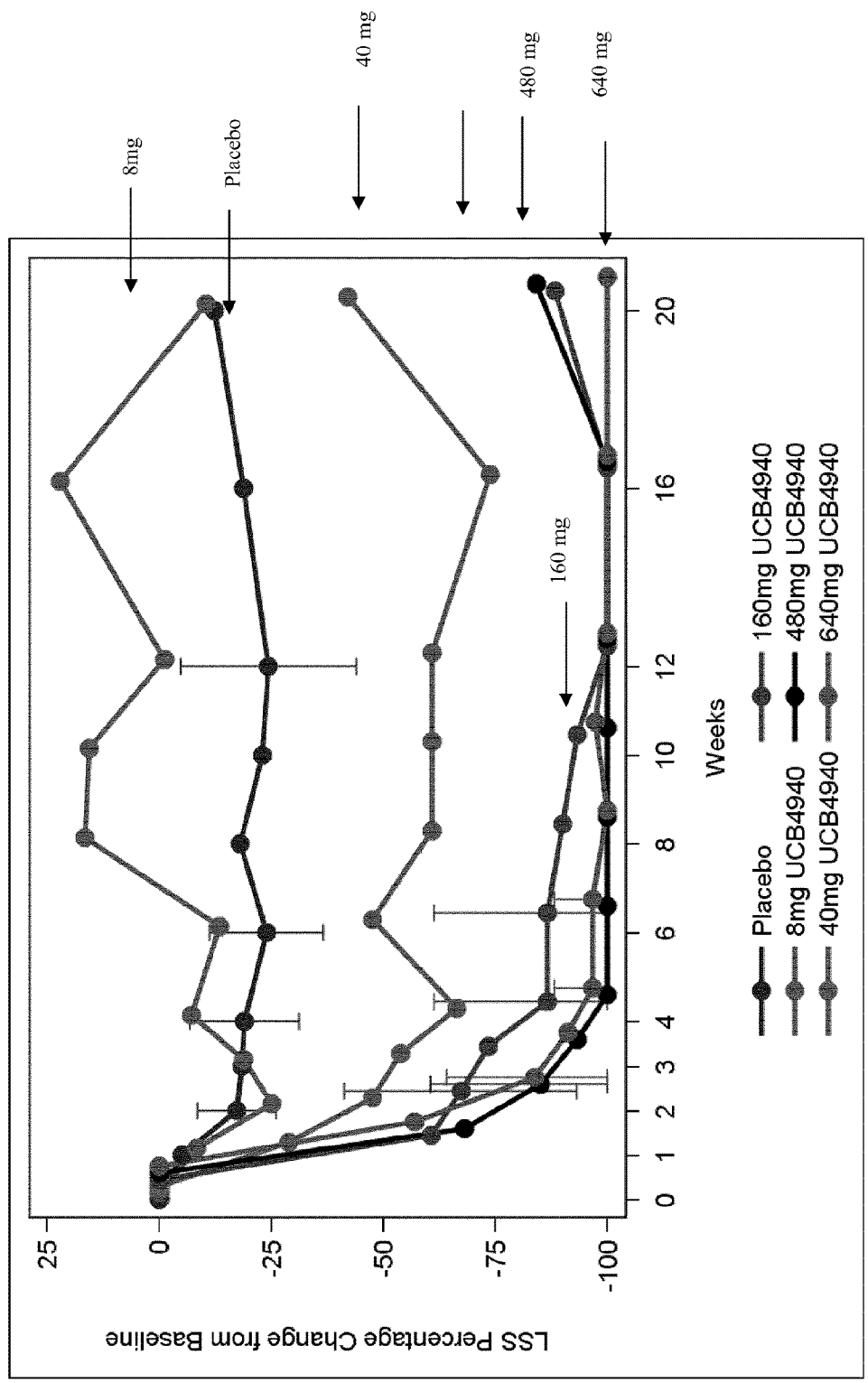
Figure 11: Percent change from baseline in lesional severity score

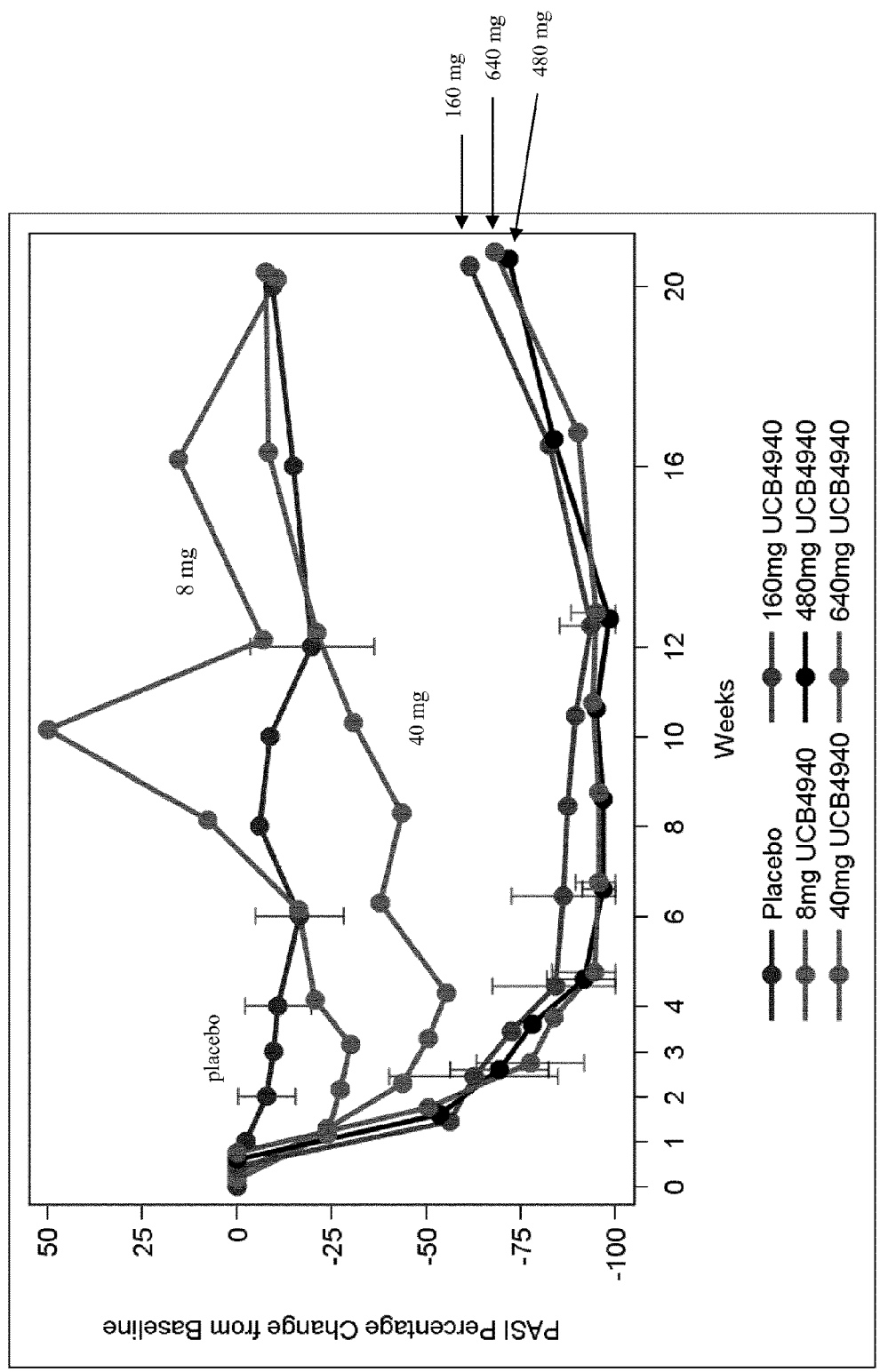
Figure 12: Percent Change for baseline in PASI

Figure 13: Summary Table of PASI 90 response

| Week | Placebo N=13 | 8mg N=4 | 40mg N=4 | 160mg N=6 | 480mg N=6+ | 640mg N=6 |
|---|---|---|---|---|---|---|
| 4 | 0 | 0 | 0 | 3 (50%) | 4 (67%) | 5 (83%) |
| 6 | 0 | 0 | 0 | 2 (33%) | 5 (83%) | 5 (83%) |
| 12 | 0 | 0 | 0 | 4 (67%) | 5 (100%) | 5 (83%) |

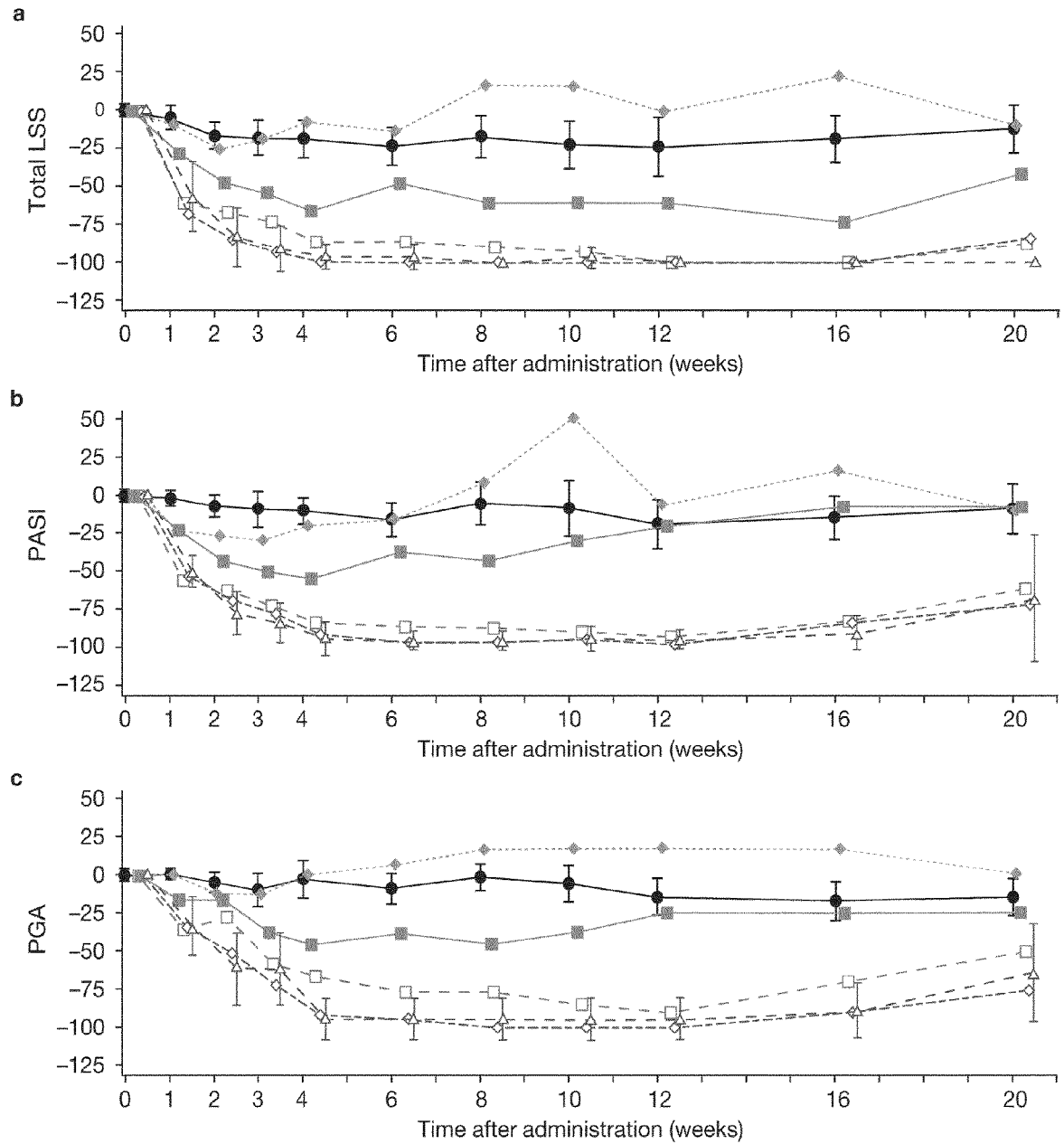
Figure 14: Mean percentage change from baseline in (a) LSS, (b) PASI and (c) PGA in the placebo and bimekizumab cohorts

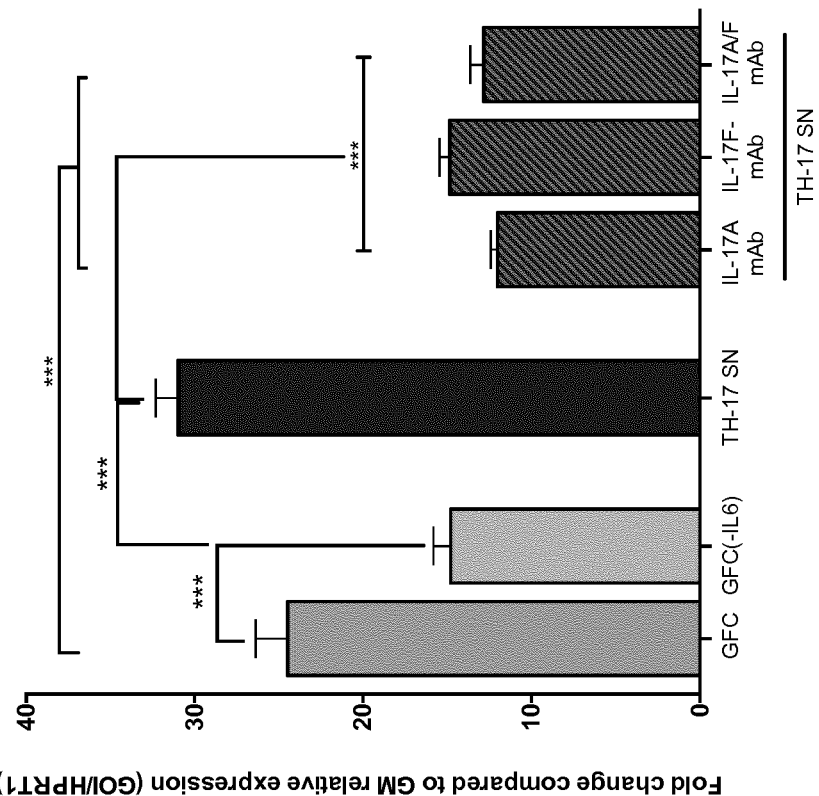
Figure 15A RUNX2
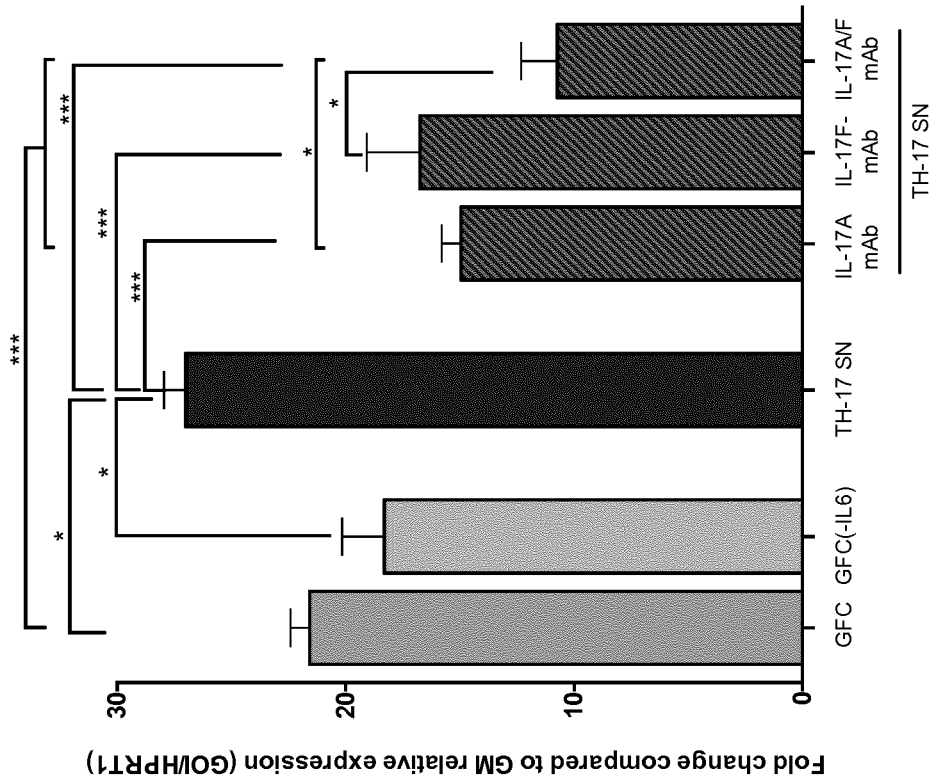
Figure 15B SP7

METHODS OF TREATMENT USING ANTI-IL-17A/F ANTIBODIES

FIELD OF THE INVENTION

The application relates to antibody molecules having specificity for antigenic determinants of both IL-17A and IL-17F, as well as therapeutic uses of the antibody molecules.

BACKGROUND

Interleukin 17 (IL-17), also known as CTLA-8 or IL-17A, is a pro-inflammatory cytokine which stimulates the secretion of a wide range of other cytokines from various non-immune cells. IL-17A is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in the presence of irradiated fibroblasts (Fossiez et al., 1998, Int. Rev. Immunol. 16, 541-551). IL-17A is predominantly produced by activated memory T cells and acts by binding to a ubiquitously distributed cell surface receptor (IL-17R) (Yao et al., 1997, Cytokine, 9, 794-800). It may also act through binding to a complex of IL-17RA and IL-17RC (Toy et al., 2006, J. Immunol. 177(11); 36-39). IL-17 producing T cells called 'TH17 cells' have been implicated in the pathogenesis of certain cancers (Weaver et al., 2006, Immunity, 24, 677-688; Langowski et al., 2006, 442, 461-465; Iwakura and Ishigame, 2006, J. Clin. Invest. 116, 5, 1218-1222).

A number of homologues of IL-17 have been identified which have both similar and distinct roles in regulating inflammatory responses. For a review of IL-17 cytokine/receptor families see Dumont, 2003, Expert Opin. Ther. Patents, 13, 287-303. One such homologue is IL-17F, also known as IL-24 and ML-1, which has been reported as around 55% identical to IL-17A and is thought to share the same receptors as IL-17A (Kolls and Linden 2004, Immunity, 21, 467-476; Hymowitz, et al., 2001, EMBO J. 20(19), 5332-5341; Kuestner et al., 2007, Journal of Immunology, 179, 5462-5473). While individual signalling molecules of IL-17A are more potent than those of IL-17F, IL-17F has a greater impact in cooperation with other molecules. For example, when IL-17F is added with TNFα to RA synoviocytes, the induction of the potent inflammatory pathway is similar to the response observed with IL-17A and TNFα. (Hot et al., 2011, Ann. Rheumatic Dis., 70, 341-348.)

IL-17A and IL-17F are expressed as homodimers, but may also be expressed as the IL-17A/F heterodimer (Wright et al. 2008, J. Immunol. 181: 2799-2805). IL-17A and F signal through the receptors IL-17R, IL-17RC or an IL-17RA/RC receptor complex (Gaffen 2008, Cytokine. 43: 402-407).

IL-17A and IL-17F have been associated with dermatological and rheumatological conditions. Such dermatological conditions include, but are not limited to, psoriasis, atopic dermatitis, discoid lupus erythematosus, alopecia areata, autoimmune urticaria, bullous pemphigoid, dermatitis herpetiformis, hidradenitis suppurativa, linear IgA dermatosis, morphea, pemphigus vulgaris, and pyoderma gangrenosum. Such rheumatological conditions include psoriatic arthritis, axial spondyloarthritis including ankylosing spondylitis, systemic lupus erythematosus (SLE), rheumatoid arthritis, vasculitis, Sjogren's syndrome (extraglandular), juvenile idiopathic arthritis, granulomatosis, Behçet's disease (mucocutaneous), antiphospholipid syndrome, giant cell arteritis, scleroderma, polyarteritis nodosa, Behçet's disease (thrombosis), and Takayasu disease.

Psoriatic arthritis is an inflammatory condition which affects both the joints and the skin. It can lead to significant joint damage and disability over time and can involve both skin and nail abnormalities seen in psoriasis. (Schett et al., 2011, Arthritis Research and Therapy, 13 Suppl. 1: S4.) Psoriatic arthritis may be difficult to distinguish from other forms of arthritis, particularly when skin changes are minimal or absent. Psoriatic arthritis patients often experience a number of other diseases at a higher frequency than the general population including autoimmune conditions such as iritis/uveitis (swelling and irritation of the eye) and inflammatory bowel disease (IBD), as well as cardiovascular disease and osteoporosis.

Psoriatic arthritis can negatively affect many aspects of a patient's life, imposing burdens of pain, physical functioning and fatigue, as well as reductions in psychological, emotional and social well-being and overall health-related quality of life. (Husted et al., 2001, Arthritis Care and Research, 45:151-8; Picchianti-Diamani et al., 2010, Qual. Life Res., 19:821-6.) Studies suggest many aspects of health-related quality of life (HRQol) are affected to a similar degree in patients with psoriatic arthritis and rheumatoid arthritis. (Husted et al., 2001, Arthritis Care and Research, 45:151-8). Psoriatic arthritis is associated with a considerable economic burden, both in terms of direct costs (money spent on medication, hospital care, informal care and over-the-counter medication) and indirect costs (those associated with a loss of productivity at work). (Ackermann & Kavanaugh, 2008, Pharmacoeconomics, 26 (2):121-9).

Psoriatic arthritis can develop in individuals with psoriasis, an inflammatory disorder of the skin (Shbeeb et al., 2000, J Rheumatol., 27: 1247-50). Psoriatic arthritis typically develops in patients after the onset of psoriasis. (Gladman et al., 2006, Annuals of the Rheumatic Diseases, 65 (Suppl. III): iii12-iii24). The mean age at which patients with psoriatic arthritis are diagnosed is 41 years, with men often diagnosed at a younger age (20-39 years) than women (40-59 years). (Shbeed et al., 2000, J Rheumatol., 27:1247-50.) Between 3 and 8 people per 100,000 are newly diagnosed with psoriatic arthritis each year. (Gladman et al., 2005, Annuals of the Rheumatic Diseases, 64(Suppl II): ii14-ii17.)

Certain genes have been associated with psoriatic arthritis, particularly the HLA-B27 (human leukocyte antigen) gene, which is present in approximately 50% of psoriatic arthritis patients, compared to just 3-18% of the Western European general population. (Gladman et al., 2005, Annuals of the Rheumatic Diseases, 64(Suppl II): ii14-ii17; Salvarani & Fries, 2009, World J. Gastroenterol., 15 (20): 2449-55.)

However, environmental factors may induce disease onset as well. Risk factors associated with psoriatic arthritis include: psoriasis involving the scalp, intergluteal areas, more than 3 affected sites, nail dystrophy, recent oral ulceration, and trauma leading to medical care. (Ogdie & Gelfand, 2010, Arch. Dermatol. 146 (7):785-8; Pattison et al., 2008, Ann. Rheum. Dis., 67 (5):672-6.)

There is a strong association between psoriasis, psoriatic arthritis and obesity. (Russolillo et al., 2013, J. Rheumatol., 52:62-67). In 80% of psoriatic arthritis cases, arthritis develops after the appearance of psoriasis.

Symptoms of psoriatic arthritis include, but are not limited, to: stiffness, pain, tenderness, swelling and throbbing in one or more joints, usually in the hands or feet, but sometimes in the wrists, ankles, knee or lower back; swollen fingers or toes that may result in a "sausage-like" appearance (dactylitis); reduced ability to move; nail changes, such as pitting or separation from the nail bed causing functional impairment, pain and emotional distress; eye redness and pain (uveitis); fatigue and morning stiffness (in affected joints); tenderness, pain and swelling over tendons (enthesitis); psoriatic arthritis may affect a small number of joints (oligoarthritis) or many joints (polyarthritis) and/or spine.

People with psoriatic arthritis symptoms, especially those with psoriasis or a family history of psoriatic arthritis, need to see a specialist (e.g. a rheumatologist), as their joint problems may be similar to those seen in other forms of arthritis (e.g. rheumatoid arthritis, gout and reactive arthritis). (Conaghan & Coates, 2009, The Practioner, 253(1724): 15-18.) Diagnosis is based on symptoms, medical history, physical examination, results of blood tests and X rays. (Conaghan & Coates, 2009, The Practioner, 253 (1724); 15-18.)

Mild cases of psoriatic arthritis are usually treated with non-steroidal anti-inflammatory drugs (NSAIDs), low doses of oral steroids or steroid injections into painful joints. (Mease, 2011, Ann. Rheum. Dis., 70(Suppl 1):i77-i84.) More severe psoriatic arthritis is often treated with disease-modifying anti-rheumatic drugs (DMARDs). (Weger, 2010, British Journal of Pharmacology, 160:810-20.) More recently, biological agents including anti-tumour necrosis factor alpha antibodies (TNFα blockers) have become available. (Weger, 2010, British Journal of Pharmacology, 160: 810-20.) Clinical evidence has demonstrated that minimal disease activity was achieved in 64% of patients treated with TNF-inhibitors, which means that a considerable portion of patients (36%) did not achieve even this target. (Haddad A et al, Arthritis Care Res. 2015; 67, 842-7).

Some subjects are not responsive to previously known treatments, do not maintain a clinical response (defined as achieving American College of Rheumatology 20% response criteria ("ACR20"), or have contraindications or intolerance to these agents. The availability of effective medicines for psoriatic arthritis that have an alternative mechanism of action will improve the treatment of patients, especially those patients who have not gained benefit from, lost effectiveness to, or could not use TNF-inhibitor medications for safety or tolerability reasons. (Mease P, Curr Opin Rheumatol. 2015, 27: 127-33). Because ACR score is a scale that measures symptoms such as joint effects associated with psoriatic arthritis and rheumatoid arthritis, improvements in ACR score are associated with the treatment of both psoriatic arthritis and rheumatoid arthritis.

Breakthroughs in the understanding of immunopathogenesis of psoriatic arthritis have led to novel therapies beyond TNF-inhibitors. These therapies are reviewed in Sritheran and Ying Leung, Ther. Adv. Musculoskel. Dis., 2015, 7(5), 173-186). Table 1 of this paper sets out the ACR and PASI scores for the various therapies.

Drugs that inhibit IL-17 and IL-23 have demonstrated significant benefit in psoriasis and emerging studies are also showing benefit in psoriatic arthritis and ankylosing spondylitis. (Mease P, Curr Opin Rheumatol 2015, 27: 127-33). Biological therapies are being developed which target IL-17A, including the anti-IL-17A antibodies secukinumab and ixekizumab which are currently in Phase III clinical trials for psoriatic arthritis. The results of a Phase II clinical study of secukinumab in psoriatic arthritis are described in Mease et al., 2015, N Engl J Med, 373, 14, 1329-1339 and in ankylosing spondylitis in Baeten et al., N. Engl. J. Med, 2015, 373 (26), 2534-48. The results of a Phase III clinical study of ixekizumab in psoriatic arthritis are described in Mease et al, 2015, ACR Abstract number 977. Brodalumab is an anti IL-17RA monoclonal antibody which, by targeting IL-17RA, blocks IL-17A, IL-17F and IL-17E (IL-25) activity. The results of a Phase II clinical study of brodalumab in psoriatic arthritis are described in Mease et al., 2015, N Engl J Med, 370, 24, 2295-2306. The efficacy of current therapies at week 24 is around 60%, 40% and 20% for ACR20, ACR50 and ACR70 respectively, along with a PASI 75 of around 65% (Table 1 in Sritheran and Ying Leung, Ther. Adv. Musculoskel. Dis., 2015, 7(5), 173-186).

SUMMARY OF THE INVENTION

The invention relates to antibody molecules having specificity for antigenic determinants of both IL-17A and IL-17F, therapeutic uses of the antibody molecules in the treatment of dermatological and rheumatological diseases, such as psoriatic arthritis, and methods for producing said antibody molecules. In one example, the antibody of the invention may be used in the treatment of dermatological conditions (such as, but not limited to, psoriasis, atopic dermatitis, discoid lupus erythematosus, alopecia areata, autoimmune urticaria, bullous pemphigoid, dermatitis herpetiformis, hidradenitis suppurativa, linear IgA dermatosis, morphea, pemphigus vulgaris, and pyoderma gangrenosum) and/or rheumatological conditions (such as, but not limited to psoriatic arthritis, axial spondyloarthritis including non-radiographic axial spondyloarthritis and ankylosing spondylitis, systemic lupus erythematosus (SLE), rheumatoid arthritis, vasculitis, Sjogren's syndrome (extraglandular), juvenile idiopathic arthritis, granulomatosis, Behçet's disease (mucocutaneous), antiphospholipid syndrome, giant cell arteritis, scleroderma, polyarteritis nodosa, Behçet's disease (thrombosis), and Takayasu disease). In one example, the antibody of the invention may be used in the treatment of psoriatic arthritis. Neutralising antibodies which bind both IL-17A and IL-17F, such as bimekizumab, may provide a significant improvement over existing psoriatic arthritis therapies, both in the speed and magnitude of clinical effect. For example, they may mediate equivalent or even improved clinical scores by week 8. Suitable clinical scores include American College of Rheumatology ("ACR") 20/50/70 response for joints and, for skin, the clinical features of psoriasis, Psoriasis Area and Severity Index ("PASI") 50/75/90 response. For example, these antibodies may increase the number of patients achieving ACR20, ACR50, ACR70 and PASI75 at week 8 or week 12 to greater than 60%, 40%, 20% and 65% respectively (average response rate). They may even have the potential to increase the number of patients achieving ACR20, ACR50, ACR70 and PASI75 at week 8 or week 12 to 60-95%, 40-60%, 20-40% and 80-100% respectively. For example these may be 80%, 60%, 40% and close to 90% or close to 100% respectively. The speed to achieving a beneficial response in subjects administered an antibody as described herein also is remarkable. For example, in various embodiments, the subject achieves ACR20 or ACR50 (or PASI 20 or PASI50) within four weeks (e.g., within three weeks or within two weeks) of a first administration. Additionally, in various embodiments, the beneficial response to the methods described herein may be sustained for a remarkable period of time. For instance, subjects administered three doses of anti-IL-17A/F antibody described herein (e.g., at days 0, 21, and 42) enjoyed near maximal-response to week 20. Thus in various aspects, the methods described herein may achieve a biological response in a subject at week 8 or week 12 that diminishes no more than 10%, no more than 20%, no more than 30%, no more than 40%, or no more than 50% at week 20. In one example, the antibody of the invention may be used in the treatment of any of the symptoms of psoriatic arthritis listed herein below, including but not limited to dactylitis, enthesitis, nail dystrophy, skin manifestations; signs and symptoms of peripheral arthritis; axial disease and structural progression of the disease. In one example, the antibody of the invention may be used to prevent the development of psoriatic arthritis or other conditions in psoriasis patients.

The invention further provides the use of an antibody molecule according to the invention in the manufacture of a medicament for the treatment or prophylaxis of a pathological disorder that is mediated by IL-17A and/or IL-17F or associated with an increased level of IL-17A and/or IL-17F. Preferably the pathological disorder may be one of the medical indications described herein. In one embodiment, the pathological disorder may comprise psoriatic arthritis. In other embodiments, the pathological disorder may comprise psoriasis, rheumatoid arthritis, and/or arthritis. In various embodiments, the pathological disorder is ankylosing spondylitis. In various embodiments, the pathological disorder is axial spondyloarthritis or non-radiographic axial spondyloarthritis.

An antibody molecule of the invention may be utilised in any therapy where it is desired to reduce the effects of IL-17A and/or IL-17F in the human or animal body. IL-17A and/or IL-17F may be circulating in the body or may be present in an undesirably high level localised at a particular site in the body, for example a site of inflammation.

In one embodiment, the invention provides a method of treating human or animal subjects suffering from or at risk of a disorder mediated by IL-17A and/or IL-17F, the method comprising administering to the subject an effective amount of an antibody molecule of the invention.

In one embodiment, the invention also provides an antibody molecule of the invention, in particular a neutralising antibody which binds human IL-17A and human IL-17F, for use in the treatment of human or animal subjects suffering from or at risk of a disorder mediated by IL-17A and/or IL-17F. Preferably the pathological disorder may be one of the medical indications described herein. In one embodiment, the pathological disorder may comprise psoriatic arthritis. In other embodiments, the pathological disorder may comprise psoriasis, rheumatoid arthritis, and/or arthritis. In one embodiment the pathological disorder may comprise ankylosing spondylitis. In one embodiment the pathological disorder may comprise axial spondyloarthritis or non-radiographic axial spondyloarthritis.

In one embodiment, the invention therefore provides an antibody molecule of the invention, in particular a neutralising antibody which binds human IL-17A and human IL-17F, for use in the treatment of psoriatic arthritis, psoriasis, rheumatoid arthritis, arthritis, axial spondyloarthritis, ankylosing spondylitis or non-radiographic axial spondyloarthritis.

"Psoriasis" encompasses disorders or skin-related components (i.e., symptoms) of disorders such as, but not limited to, plaque psoriasis, pustular psoriasis, generalised pustular psoriasis, palmo-plantar psoriasis, scalp psoriasis, guttate psoriasis, erythrodermic psoriasis, inversive psoriasis, acrodermatitis continua, SAPHO (Synovitis, Acne, Pustulosis, Hyperostosis and Osteitis) syndrome, hidradenitis suppurativa, and DITRA (deficiency of the IL-36 receptor [IL-36R] antagonist)/DIRA (deficiency of the interleukin 1 (IL-1) receptor antagonist). The severity of psoriasis may vary and may be selected, for example, from mild, mild to moderate, moderate, severe and moderate to severe psoriasis.

An antibody molecule according to the invention may also be used in diagnosis, for example in the in vivo diagnosis and imaging of disease states involving IL-17A and/or IL-17F.

The invention provides a method of treating psoriatic arthritis in a human comprising the step of administering to the human a neutralizing antibody which binds human IL-17A and human IL-17F. In an embodiment, the antibody specifically binds an epitope of human IL-17F, the epitope comprising one or more residues selected from ARG47, ARG73, LEU75 and ILE86 of SEQ ID NO: 27. In the same or a different embodiment, the antibody specifically binds an epitope of human IL-17A, the epitope comprising one or more residues selected from TYR44, ASN45, ARG46, TRP51, ASN52, HIS54 and ASP84 of SEQ ID NO: 28. In various embodiments, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. Optionally, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. In various embodiments, the antibody comprises a light chain variable domain and a heavy chain variable domain, wherein the variable domain of the light chain comprises the sequence given in SEQ ID NO:10. In one aspect, the antibody is bimekizumab. Optionally, the antibody is administered as a pharmaceutical composition. In various embodiments, the antibody is administered subcutaneously or intravenously.

In any of the embodiments of the method of treating psoriatic arthritis in a human comprising the step of administering to the human a neutralizing antibody which binds human IL-17A and human IL-17F, the human optionally has a diagnosis of adult-onset psoriatic arthritis.

Optionally, the human is at least 18 years of age and/or was diagnosed at least six months prior to administration of the antibody. Also optionally, the human was diagnosed based on the CASPAR criteria. In any of the embodiments described above, the human has active arthritis. This is typically defined as ≥3 tender and ≥3 swollen joints. The patients may have coexistent or concomitant psoriasis and/or a history of psoriasis. For example, the human optionally has active psoriatic lesions or a history of psoriatic lesions.

In any of the embodiments of the method of treating psoriatic arthritis, psoriasis, rheumatoid arthritis or axial spondylitis, including ankylosing spondylitis and non-radiographic spondylitis in a human comprising the step of administering to the human a neutralizing antibody which binds human IL-17A and human IL-17F described herein, the antibody may be administered as a monotherapy.

In any of the embodiments of the method of treating psoriatic arthritis, psoriasis, rheumatoid arthritis or axial spondylyitis, including ankylosing spondylitis and non-radiographic spondylitis in a human comprising the step of administering to the human a neutralizing antibody which binds human IL-17A and human IL-17F described herein, the human optionally is biologic-naïve i.e. has not been previously treated with a biological agent, such as a TNF alpha inhibitor such as an anti-TNF antibody.

In any of the embodiments of the method of treating psoriatic arthritis in a human comprising the step of administering to the human a neutralizing antibody which binds human IL-17A and human IL-17F described herein, the human optionally is an inadequate responder to at least one non-biologic disease-modifying antirheumatic drug ("DMARD") and/or one or more approved biologic DMARD (e.g., a TNF inhibitor such as an anti-TNF antibody, examples including infliximab or adalimumab, or a soluble TNF receptor, such as etanercept). Examples of non-biologic DMARDs include sulfsalazine, methotrexate, cyclosporine, hydrozychloroquine, azathioprine and leflunomide. Optionally the human is an inadequate responder to at least one non-steroidal anti-inflammatory drug (NSAID). Examples of suitable NSAIDs include but are not limited to, propionic acid derivative, acetic acid derivative, enolic acid derivatives, fenamic acid derivatives, cox inhibitors, ibuprofen, fenoprofen and aspirin.

The invention also provides a method of treating psoriatic arthritis in a human concurrently treated with methotrexate or other non-biologic DMARD (such as leflunomide) or non-steroidal anti-inflammatory drug (NSAID) and/or steroid comprising the step of administering to the human a neutralizing antibody which binds human IL-17A and human IL-17F. In various embodiments, the antibody specifically binds an epitope of human IL-17F, the epitope comprising one or more residues selected from ARG47, ARG73, LEU75 and ILE86 of SEQ ID NO: 27. In the same or different embodiments, the antibody specifically binds an epitope of human IL-17A, the epitope comprising one or more residues selected from TYR44, ASN45, ARG46, TRP51, ASN52, HIS54 and ASP84 of SEQ ID NO: 28. Optionally, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. Also optionally, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. In various aspects of the method, the antibody comprises a light chain variable domain and a heavy chain variable domain, wherein the variable domain of the light chain comprises the sequence given in SEQ ID NO:10. In a preferred embodiment, the antibody is bimekizumab. The antibody may be administered as a pharmaceutical composition. The antibody is optionally administered subcutaneously or intravenously.

The invention includes a method of treating psoriatic arthritis in a human comprising the step of administering to the human a therapeutically effective amount of a neutralizing antibody which binds human IL-17A and human IL-17F. In various aspects, the antibody specifically binds an epitope of human IL-17F, the epitope comprising one or more residues selected from ARG47, ARG73, LEU75 and ILE86 of SEQ ID NO: 27. In the same or different aspects, the antibody specifically binds an epitope of human IL-17A, the epitope comprising one or more residues selected from TYR44, ASN45, ARG46, TRP51, ASN52, HIS54 and ASP84 of SEQ ID NO: 28. Optionally, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various embodiments, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. The antibody, in various embodiments, comprises a light chain variable domain and a heavy chain variable domain, wherein the variable domain of the light chain comprises the sequence given in SEQ ID NO:10. In a preferred embodiment, the antibody is bimekizumab. The antibody is optionally administered as a pharmaceutical composition. The antibody may be administered subcutaneously or intravenously.

An embodiment of the invention includes a method of treating psoriatic arthritis in a human patient comprising the step of administering to the patient a neutralizing antibody which binds human IL-17A and human IL-17F in an amount that is effective to provide an ACR20 response at week 8 or week 12, an ACR50 response at week 8 or week 12, or an ACR70 response at week 8 or week 12 in a population of patients in need of treatment. For example, the administered amount is effective to provide an ACR50 response at week 8 or week 12, or an ACR70 response at week 8 or week 12 in the population of patients. In a preferred aspect, the amount is effective to provide an ACR70 response at week 8 or week 12 in the population of patients. Alternatively or in addition, the neutralizing antibody is administered in an amount that is effective to provide a PASI50 response at week 8 or week 12, PASI75 response at week 8 or week 12, or a PASI90 response at week 8 or week 12, such as an amount that is effective to provide a PASI75 response at week 8 or week 12, or a PASI90 response at week 8 or week 12 in the population of patients. In a preferred aspect, the neutralizing antibody is administered in an amount that is effective to provide a PASI90 response or a PASI100 response at week 8 or week 12 in the population of patients. Typically the response is sustained such that ACR50, ACR70 and/or PASI responses may be maintained to week 16, 20, 24 or later. In various aspects, the antibody specifically binds an epitope of human IL-17F, the epitope comprising one or more residues selected from ARG47, ARG73, LEU75 and ILE86 of SEQ ID NO: 27 and/or specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody is optionally administered as a pharmaceutical composition. The antibody may be administered subcutaneously or intravenously.

The invention further provides a method of reducing psoriasis in a human comprising the step of administering to the human a neutralizing antibody which binds human IL-17A and human IL-17F. In various embodiments, the psoriasis is plaque psoriasis. In various embodiments the psoriasis is mild to moderate plaque psoriasis. In various embodiments the psoriasis is moderate to severe plaque psoriasis. The reduction of plaque psoriasis is optionally measured by PASI criteria. In various embodiments, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. Optionally, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. In various embodiments, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously. In one or more embodiments, the psoriasis treated using the method of the present invention may be selected from plaque psoriasis, pustular psoriasis, generalised pustular psoriasis, palmo-plantar psoriasis, nail psoriasis, scalp psoriasis, guttate psoriasis, erythrodermic psoriasis, inversive psoriasis.

The invention also includes a method of treating psoriasis in a human comprising the step of administering to the human a therapeutically effective amount of a neutralizing antibody which binds human IL-17A and human IL-17F.

The invention further provides a method of treating psoriasis in a human patient comprising the step of administering to the patient a neutralizing antibody which binds human IL-17A and human IL-17F in an amount that is effective to provide a PASI75 response at week 8 or week 12, or a PASI90 response at week 8 or week 12. In a preferred aspect, the neutralizing antibody is administered in an amount that is effective to provide a PASI75 response or a PASI90 response at week 8 or week 12 in the population of patients. In various aspects, the antibody specifically binds an epitope of human IL-17F, the epitope comprising one or more residues selected from ARG47, ARG73, LEU75 and ILE86 of SEQ ID NO: 27 and/or specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody is optionally administered as a pharmaceutical composition. The antibody may be administered subcutaneously or intravenously.

The method of treating psoriasis optionally comprises administering to the human a loading dose of the neutralizing antibody followed by at least one maintenance dose of the antibody. In various embodiments, the loading dose is between 80 and 560 mg and the at least one maintenance dose is between 40 and 320 mg. In one aspect of the method, the loading dose is 80 mg and the at least one maintenance dose is 40 mg. In another aspect of the method, the loading dose is 160 mg and the at least one maintenance dose is 80 mg. In a further aspect, the loading dose is 240 mg and the at least one maintenance dose is 160 mg. In a further aspect, the loading dose is 320 mg and the at least one maintenance dose is 160 mg. In another aspect, the loading dose is 560 mg and the at least one maintenance dose is 320 mg. In various embodiments, the loading dose is administered followed by two maintenance doses. Optionally, the loading dose is administered followed by at least one maintenance dose at a three week interval or a four week interval.

In any of the embodiments of the method of treating psoriasis in a human comprising the step of administering to the human a neutralizing antibody which binds human IL-17A and human IL-17F described herein, the human optionally is an inadequate responder to at least one non-biologic disease-modifying antirheumatic drug ("DMARD") and/or one or more approved biologic DMARD (e.g., a TNF inhibitor such as an anti-TNF antibody, examples including infliximab or adalimumab, or a soluble TNF receptor, such as etanercept). Examples of non-biologic DMARDs include sulfsalazine, methotrexate, cyclosporine, hydrozychloroquine, azathioprine and leflunomide. Optionally the human is an inadequate responder to at least one non-steroidal anti-inflammatory drug (NSAID). Examples of suitable NSAIDs include but are not limited to, propionic acid derivative, acetic acid derivative, enolic acid derivatives, fenamic acid derivatives, cox inhibitors, ibuprofen, fenoprofen and aspirin.

The invention also provides a method of treating psoriasis in a human concurrently treated with methotrexate or other non-biologic DMARD (such as leflunomide) or non-steroidal anti-inflammatory drug (NSAID) and/or steroid comprising the step of administering to the human a neutralizing antibody which binds human IL-17A and human IL-17F.

The invention also provides a method of reducing joint effects in a human comprising the step of administering to the human a neutralizing antibody which binds human IL-17A and human IL-17F. The reduction of joint effects is optionally measured by ACR criteria. In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously. Such joint effects may also include peripheral joint involvement, including synovitis, enthesitis and/or dactylitis.

The invention provides a method of reducing psoriasis and reducing joint effects in a human comprising the step of administering to the human a neutralizing antibody which binds human IL-17A and human IL-17F. In various embodiments, the psoriasis is plaque psoriasis. The reduction of plaque psoriasis is optionally measured by PASI criteria and/or the reduction of joint effects is optionally measured by ACR criteria. Alternatively or in addition, the reduction of joint effects, such as structural progression, may be measured by modified total sharp score (mTSS). Where measured, a reduction in enthesitis or dactylitis may be measured by a reduction in Leeds enthesitis index (LEI) and Leeds dactylitis index (LDI) scores respectively. In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

The invention further provides a method of treating psoriatic arthritis in a human, comprising the step of administering to the human a loading dose of a neutralizing antibody which binds human IL-17A and human IL-17F followed by at least one maintenance dose of the antibody. Optionally, the loading dose is between 80 and 560 mg and the at least one maintenance dose is between 40 and 320 mg. In one aspect of the method, the loading dose is 80 mg and the at least one maintenance dose is 40 mg. In another aspect of the method, the loading dose is 160 mg and the at least one maintenance dose is 80 mg. In a further aspect, the loading dose is 240 mg and the at least one maintenance dose is 160 mg. In a further aspect, the loading dose is 320 mg and the at least one maintenance dose is 160 mg. In another aspect, the loading dose is 560 mg and the at least one maintenance dose is 320 mg. In various embodiments, the loading dose is administered followed by two maintenance doses. Optionally, the loading dose is administered followed by at least one maintenance dose at a three week interval or a four week interval. The antibody, in various embodiments, specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. In various aspects, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

An embodiment of the invention may include a method of treating psoriatic arthritis in a human, comprising the step of administering to the human at least one dose of a neutralizing antibody which binds human IL-17A and human IL-17F. In various embodiments, at least one dose is between 40 and 640 mg of the antibody. For example, in various aspects, at least one dose is 40 mg of the antibody. In various aspects, at least one dose is 80 mg of the antibody. In various aspects, at least one dose is 160 mg of the antibody. In various aspects, at least one dose is 240 mg of the antibody. In various aspects, at least one dose is 320 mg of the antibody. In various aspects, at least one dose is 480 mg of the antibody. In various aspects, at least one dose is 560 mg of the antibody. In various aspects, at least one dose is 640 mg of the antibody. In any of the aspects, the doses are optionally administered at a three week interval or a four week interval. In any of the aspects, the doses are optionally administered at an eight week interval or a twelve week interval. In any of the aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

The invention also provides a method of treating rheumatoid arthritis in a human comprising the step of administering to the human a neutralizing antibody which binds human IL-17A and human IL-17F. In various aspects, the antibody specifically binds an epitope of human IL-17F, the epitope comprising one or more residues selected from ARG47, ARG73, LEU75 and ILE86 of SEQ ID NO: 27.

Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various embodiments, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. Optionally, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. In various embodiments, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

In various embodiments of the method of treating rheumatoid arthritis in a human, the human has a diagnosis of adult-onset rheumatoid arthritis; optionally, the human is at least 18 years of age. Also optionally, the human was diagnosed at least six months prior to administration of the antibody. In various embodiments, the human was classified based on the ACR/EULAR 2010 criteria. In various embodiments of the method of treating rheumatoid arthritis in a human, the human has active arthritis. In various aspects of the method of treating rheumatoid arthritis in a human, the human is an inadequate responder to at least one non-biologic disease-modifying antirheumatic drug ("DMARD") and/or at least one approved biologic DMARD. Alternatively, or in addition, the human may be an inadequate responder to at least one non-steroidal anti-inflammatory drug (NSAID).

The invention provides a method of treating rheumatoid arthritis in a human concurrently treated with methotrexate or other non-biologic DMARD (such as leflunomide) or non-steroidal anti-inflammatory drug (NSAID) and/or steroid comprising the step of administering to the human a neutralizing antibody which binds human IL-17A and human IL-17F. In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. Optionally, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. In various aspects, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

The invention includes a method of treating rheumatoid arthritis in a human comprising the step of administering to the human a therapeutically effective amount of a neutralizing antibody which binds human IL-17A and human IL-17F. In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

The invention further includes a method of treating rheumatoid arthritis in a human patient comprising the step of administering to the patient a neutralizing antibody which binds human IL-17A and human IL-17F in an amount that is effective to provide an ACR20 response at week 8 or week 12, an ACR50 response at week 8 or week 12, or an ACR70 response at week 8 or week 12 in a population of patients in need of treatment. For example, in various aspects, the amount administered is effective to provide an ACR50 response at week 8 or week 12, or an ACR70 response at week 8 or week 12 in the population of patients. In a preferred aspect, the amount is effective to provide an ACR70 response at week 8 or week 12 in a population of patients in need of treatment. In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various embodiments, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various embodiments, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect of the invention, the antibody is bimekizumab. The antibody may be administered as a pharmaceutical composition. The antibody is optionally administered subcutaneously or intravenously.

The invention also provides a method of treating rheumatoid arthritis in a human, comprising the step of administering to the human a loading dose of a neutralizing antibody which binds human IL-17A and human IL-17F followed by at least one maintenance dose of the antibody. In various aspects, the loading dose is between 80 and 560 mg and the at least one maintenance dose is between 40 and 320 mg. For example, in various embodiments, the loading dose is 80 mg and the at least one maintenance dose is 40 mg, the loading dose is 160 mg and the at least one maintenance dose is 80 mg, the loading dose is 240 mg and the at least one maintenance dose is 160 mg, the loading dose is 320 mg and the at least one maintenance dose is 160 mg, or the loading dose is 560 mg and the at least one maintenance dose is 320 mg. Optionally, the loading dose is administered followed by two maintenance doses. Also optionally, the loading dose is administered followed by at least one maintenance dose at a three week interval or a four week interval. In various embodiments, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

The invention further provides a method of treating rheumatoid arthritis in a human, comprising the step of administering to the human at least one dose of a neutralizing antibody which binds human IL-17A and human IL-17F. Optionally, the at least one dose is between 40 and 640 mg of the antibody. For example, at least one dose is 40 mg of the antibody or 80 mg of the antibody or 160 mg of the antibody or 240 mg of the antibody or 320 mg of the antibody or 480 mg of the antibody or 560 mg of the antibody or 640 mg of the antibody. Also optionally, the doses are administered at a three week interval or a four week interval. In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously.

The invention also provides a method of treating axial spondyloarthritis (e.g., ankylosing spondylosis) comprising the step of administering to the human a neutralizing antibody which binds human IL-17A and human IL-17F. Axial spondyloarthritis refers to a group of inflammatory arthritis diseases which primarily affects the spine and other joints, causing inflammation and chronic pain in the spine and sacroliliac joints which may eventually result in syndemophyte formation and which includes both ankylosing spondylitis and nonradiographic spondylitis. Thus, the invention provides a method for treating (e.g., ameliorating the symptoms of, reducing the progression of) ankylosing spondylosis and/or nonradiographic axial spondyloarthritis (nr-axSpA). In various aspects, the antibody specifically binds an epitope of human IL-17F, the epitope comprising one or more residues selected from ARG47, ARG73, LEU75 and ILE86 of SEQ ID NO: 27. Alternatively or in addition, the antibody specifically binds an epitope of human IL-17A, the epitope comprising one or more residues selected from TYR44, ASN45, ARG46, TRP51, ASN52, HIS54 and ASP84 of SEQ ID NO: 28. In various aspects, the antibody binds to the same epitope on human IL-17A, human IL-17F, or IL-17 A/F heterodimer as a neutralising antibody that has a heavy chain comprising the sequence given in SEQ ID NO: 11 and a light chain comprising the sequence given in SEQ ID NO: 10. In various aspects, the antibody cross-blocks a neutralising antibody that has a heavy chain comprising the sequence given in SEQ ID NO: 11 and a light chain comprising the sequence given in SEQ ID NO: 10 and binds human IL-17A and human IL-17F. Optionally, the antibody comprises a light chain variable domain and a heavy chain variable domain, wherein the variable domain of the light chain comprises the sequence given in SEQ ID NO:10. In a preferred aspect, the antibody is bimekizumab. The antibody may be administered as a pharmaceutical composition. The antibody is optionally administered subcutaneously or intravenously. Preferably the antibody is administered in a therapeutically effective amount. Any of the dosing regimens described herein are suitable for use in the context of this method. For example, in various embodiments, the method comprises administering to a subject a 16 mg, 64 mg, 160 mg, or 320 mg of antibody every four weeks, optionally for a treatment period of 12 weeks, 36 weeks, 48 weeks, or 52 weeks. The amount and timing of administration is preferably sufficient to achieve at least an ASAS20 response (e.g., ASAS40,) at week 2, week 4, week 8, or week 12 of treatment. ASAS scoring and methods of evaluating the severity of axial spondylitis are further described in Ann Rheum Dis 2009; 68; ii1-ii44. In one example the amount and timing of administration is preferably sufficient to achieve an ASAS40 at week 12 of treatment. In one example the amount and timing of administration is preferably sufficient to provide at least 30% or at least 40% or at least 45% or at least 50% of subjects achieving an ASAS40 response at week 12 of treatment. In various embodiments, the invention provides a method of inhibiting (e.g., slowing the progression of) periosteal bone formation in a human, such as a human suffering from spondyloarthritis (e.g., ankylosing spondylosis), by administering a neutralizing antibody which binds human IL-17A and human IL-17F as described herein. Periosteal bone formation is evaluated via, e.g., radiography In any of the embodiments of the method of treating axial spondyloarthritis including ankylosing spondylitis and nr-axSpA in a human comprising the step of administering to the human a neutralizing antibody which binds human IL-17A and human IL-17F, the human optionally has a diagnosis of adult-onset ankylosing spondylitis or nr-axSpA. Optionally, the human is at least 18 years of age and/or was diagnosed at least six months prior to administration of the antibody. Also optionally, the human has been classified based on the modified New York or ASAS criteria. In any of the embodiments described above, the human has active axial arthritis.

In any of the embodiments of the method of treating axial spondyloarthritis including ankylosing spondylitis and/or nr-axSpA in a human comprising the step of administering to the human a neutralizing antibody which binds human IL-17A and human IL-17F described herein, the human optionally is an inadequate responder to at least one non-steroidal anti-inflammatory drug ("NSAID") and/or one or more approved biologic DMARD (e.g., a TNF inhibitor such as an anti-TNF antibody, examples including infliximab or adalimumab, or a soluble TNF receptor, such as etanercept).

The invention also provides a method of treating axial spondyloarthritis including ankylosing spondylitis and/or nr-axSpA in a human concurrently treated with a non-steroidal anti-inflammatory drug (NSAID) comprising the step of administering to the human a neutralizing antibody which binds human IL-17A and human IL-17F.

Also included in the invention is a method of treating psoriatic arthritis comprising the step of administering a neutralizing antibody which binds human IL-17A and human IL-17F in an amount that is effective to provide at least 50% of subjects achieving an ACR20 response at week 8 or week 12. For example, the amount is effective to provide at least 51, 52, 53, 54, 55, 56, 57, 58, 59, 60, 61, 62, 63, 64 or 65% of subjects achieving an ACR20 response at week 8 or week 12. In one example, the amount is effective to provide at least 50-90% or 60-90% or 63-91% of subjects achieving an ACR20 response at week 8 or week 12. In one example, the amount is effective to provide at least 40%, at least 45%, at least 50% or at least 55% of subjects achieving an ACR50 response at week 8 or week 12 or week 20. Alternatively or in addition, the amount of neutralizing antibody is effective to provide at least 80% of subjects achieving a PASI75 response at week 8 or week 12. For example, the amount is effective to provide 80-100% of subjects achieving a PASI75 response at week 8 or week 12, such as an amount effective to provide at least 80, 85, 90, 95 or 99% of subjects achieving a PASI75 response at week 8 or week 12. In various embodiments, the amount of neutralizing antibody is effective to provide at least 60% of subjects achieving a PASI90 response or a PASI100 response at week 8 or week 12, e.g., an amount effective to provide 60-100% or 62-96% of subjects achieving a PASI90 response at week 8 or week 12 (such as an amount effective to provide at least 60, 65, 70, 75, 80, 85, 90, 95 or 96% of subjects achieving a PASI90 response at week 8 or week 12).

BRIEF DESCRIPTION OF THE FIGURES

FIG. 1: Nucleotide and Amino Acid Sequences
FIG. 2: CASPAR criteria

FIG. 3a: PASI 50/75/90 response at week 8 for cohorts 1-4 described in Example 1.
FIG. 3b: Time course of PASI 90-response (PA0007) from first dose (day 0) to day 140 (week 20) in Example 1.
FIG. 4: Secukinumab Future 1 Results: PASI
FIG. 5a: ACR20/50/70 response at week 8 for cohorts 1-4 described in Example 1.
FIGS. 5(b)-5(d): Summary Plots of the ACR20/50/70 response rates from PA0007 from start of study (day 0) to day 140 (week 20) (Example 1).
FIG. 6: Secukinumab Future 1 Results and Cimzia RAPID PSA results: ACR20
FIG. 7: Summary Table of Bayesian Analysis
FIG. 8: Summary Table of ACR20 response at week 8 in psoriatic arthritis for registered anti-TNFs or Phase III results. References 1. Mease P J, Gladman D D, Ritchlin C T, Ruderman E M, Steinfeld S D, Choy E H, et al. Adalimumab for the treatment of patients with moderately to severely active psoriatic arthritis: results of a double-blind, randomized, placebo-controlled trial. Arthritis and rheumatism. 2005; 52(10):3279-89. 2. Kavanaugh A, McInnes I, Mease P, Krueger G G, Gladman D, Gomez-Reino J, et al. Golimumab, a new human tumor necrosis factor alpha antibody, administered every four weeks as a subcutaneous injection in psoriatic arthritis: Twenty-four-week efficacy and safety results of a randomized, placebo-controlled study. Arthritis and rheumatism. 2009; 60(4):976-86. 3. Mease P J, Fleischmann R, Deodhar A A, Wollenhaupt J, Khraishi M, Kielar D, et al. Effect of certolizumab pegol on signs and symptoms in patients with psoriatic arthritis: 24-week results of a Phase 3 double-blind randomised placebo-controlled study (RAPID-PsA). Annals of the rheumatic diseases. 2014; 73(1):48-55. 4. McInnes I B, Mease P J, Kirkham B, Kavanaugh A, Ritchlin C T, Rahman P, et al. Secukinumab, a human anti-interleukin-17A monoclonal antibody, in patients with psoriatic arthritis (FUTURE 2): a randomised, double-blind, placebo-controlled, phase 3 trial. Lancet. 2015; 386(9999):1137-46. 5. McInnes I B, Kavanaugh A, Gottlieb A B, Puig L, Rahman P, Ritchlin C, et al. Efficacy and safety of ustekinumab in patients with active psoriatic arthritis: 1 year results of the phase 3, multicentre, double-blind, placebo-controlled PSUMMIT 1 trial. Lancet. 2013; 382(9894):780-9.

FIG. 9: Targeted CA028_0496.g3 PK concentrations
FIG. 10: Summary PK plot of predicted SC dosing, illustrating that a dose of 320 loading followed by 160 mg Q4W or 160 mg Q4W and higher, are able to achieve the plasma concentrations studied in PA0007 at the top 3 doses.
FIG. 11: Percent change from baseline in lesional severity score in study UP0008
FIG. 12: Percent Change for baseline in PASI in study UP0008
FIG. 13: Summary Table of PASI 90 response in study UP0008
FIGS. 14A-14C: Mean percentage change from baseline in (A) LSS, (B) PASI and (C) PGA in the placebo and bimekizumab cohorts. Closed circles=placebo; diamonds=8 mg bimekizumab; closed squares=40 mg bimekizumab; open squares=160 mg bimekizumab; open diamonds=480 mg bimekizumab; open triangles=640 mg bimekizumab.
FIGS. 15A-15G: FIGS. 15A-15E are bar graphs illustrating osteogenic gene expression in hPDSCs following treatment with GFC (growth factor cocktail; first bar from left), GFC (-IL-6) (growth factor cocktail without IL-6; second bar), TH-17SN (TH-17 supernatant in (GFC-IL-6), third bar), TH-17SN+IL-17A mAb ((TH-17 supernatant in (GFC-IL-6) with IL-17A monoclonal antibody treatment; fourth bar), or IL-17F mAb ((TH-17 supernatant in (GFC-IL-6) with IL-17F monoclonal antibody treatment; fifth bar), or IL-17A/F mAb ((TH-17 supernatant in (GFC-IL-6) with IL-17A/F monoclonal antibody treatment; sixth bar). FIG. 15F is a bar graph illustrating in vitro mineralisation (y-axis=Absorbance at 595 nm; bars from left to right: Control, GFC, GFC-IL-6, TH-17SN, IL-17A mAb, IL-17F mAb, IL-17A/F mAb). FIG. 15G is a bar graph illustrating IL-6 gene expression following treatment with GFC (growth factor cocktail; first bar from left), GFC (-IL-6) (growth factor cocktail without IL-6; second bar), TH-17SN (TH-17 supernatant in (GFC-IL-6), third bar), TH-17SN+IL-17A mAb ((TH-17 supernatant in (GFC-IL-6) with IL-17A monoclonal antibody treatment; fourth bar), or IL-17F mAb ((TH-17 supernatant in (GFC-IL-6) with IL-17F monoclonal antibody treatment; fifth bar), or IL-17A/F mAb ((TH-17 supernatant in (GFC-IL-6) with IL-17A/F monoclonal antibody treatment; sixth bar). Results are expressed as the mean fold change in expression compared to GM±SEM. *$p<0.001$; $p<0.01$; *$p<0.05$ as compared by one-way ANOVA (n=3) between all treatment groups.

DETAILED DESCRIPTION OF THE INVENTION

Antibodies

Figure 15C:
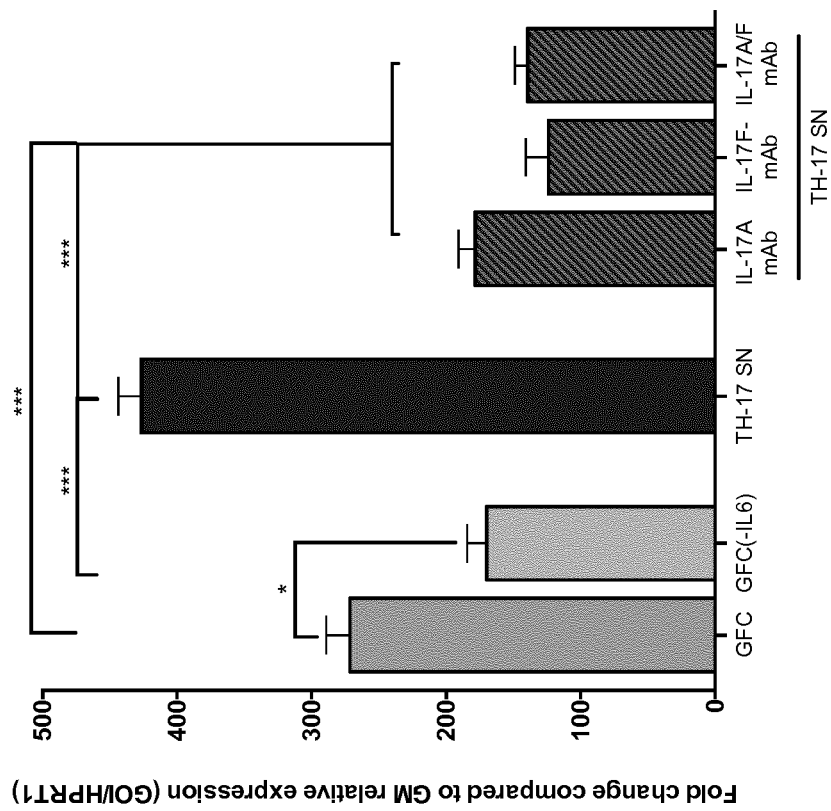
Figures 15D, 15E:
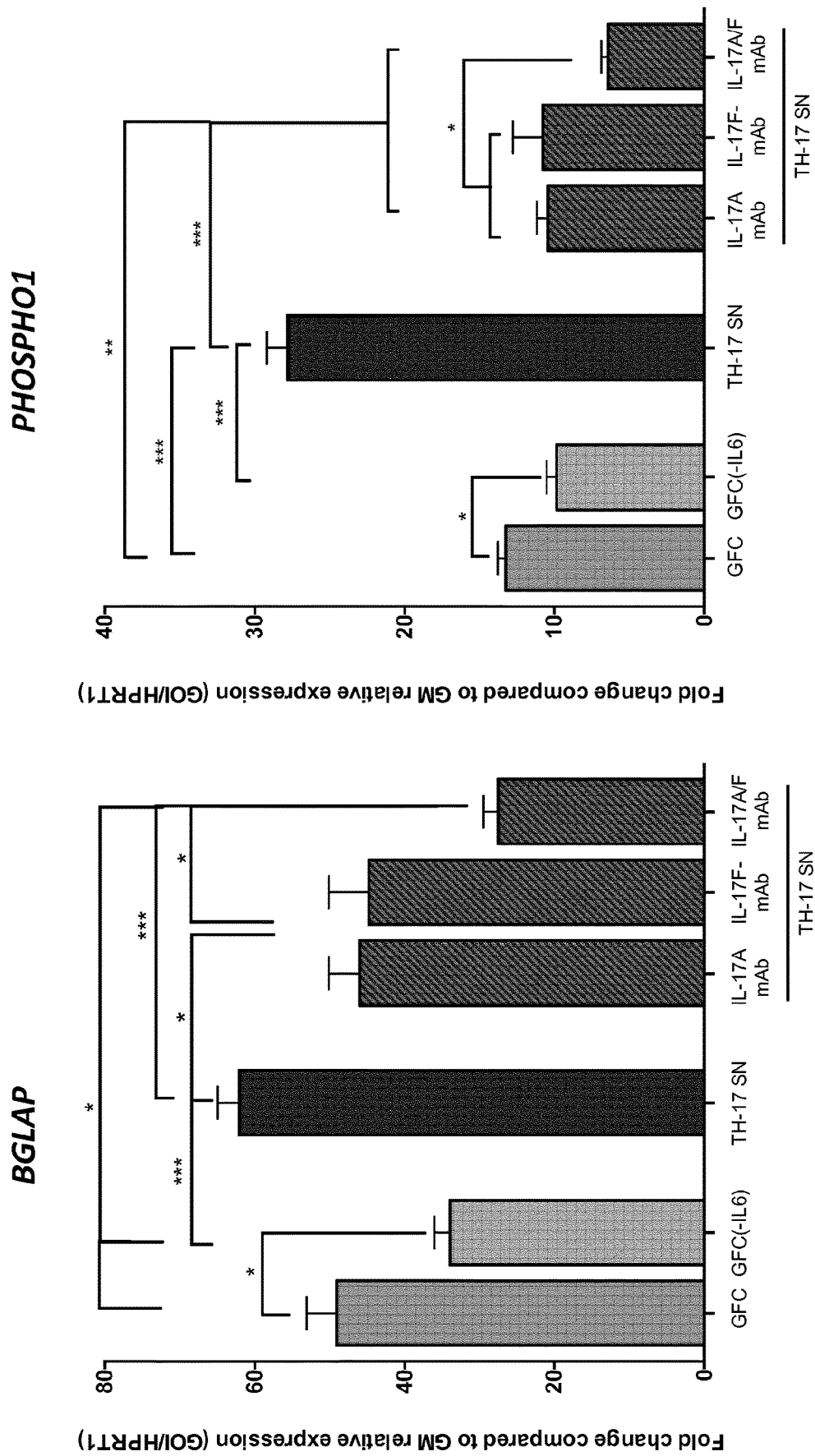
Figure 15G:
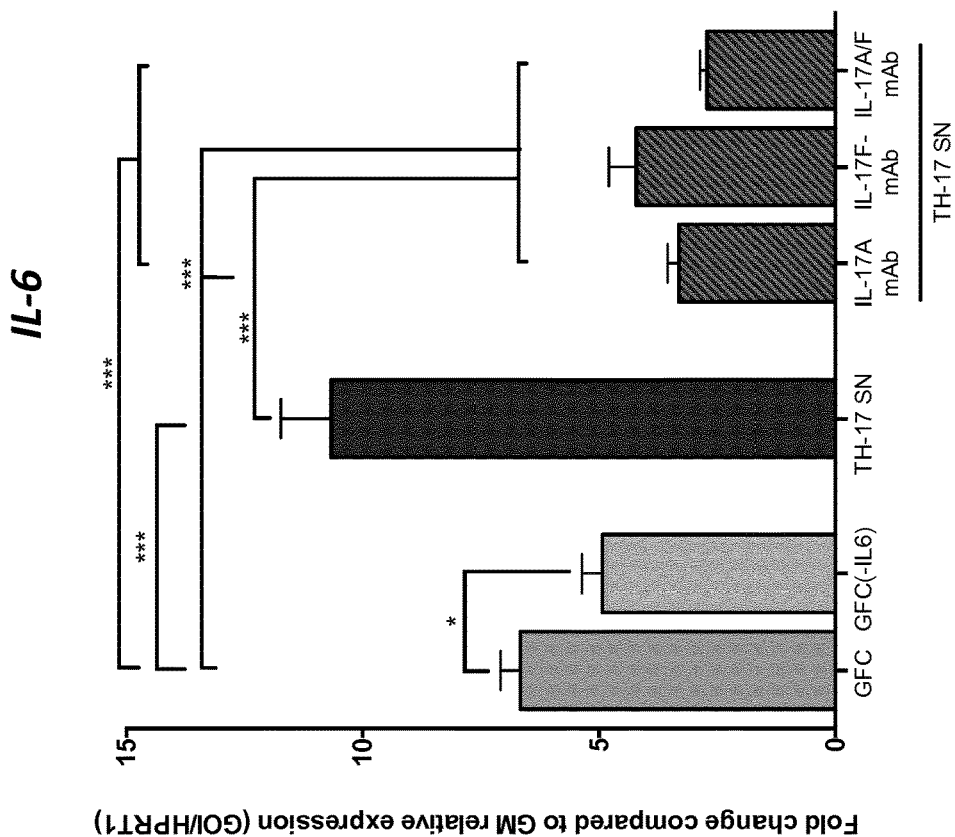
Figure 15F:
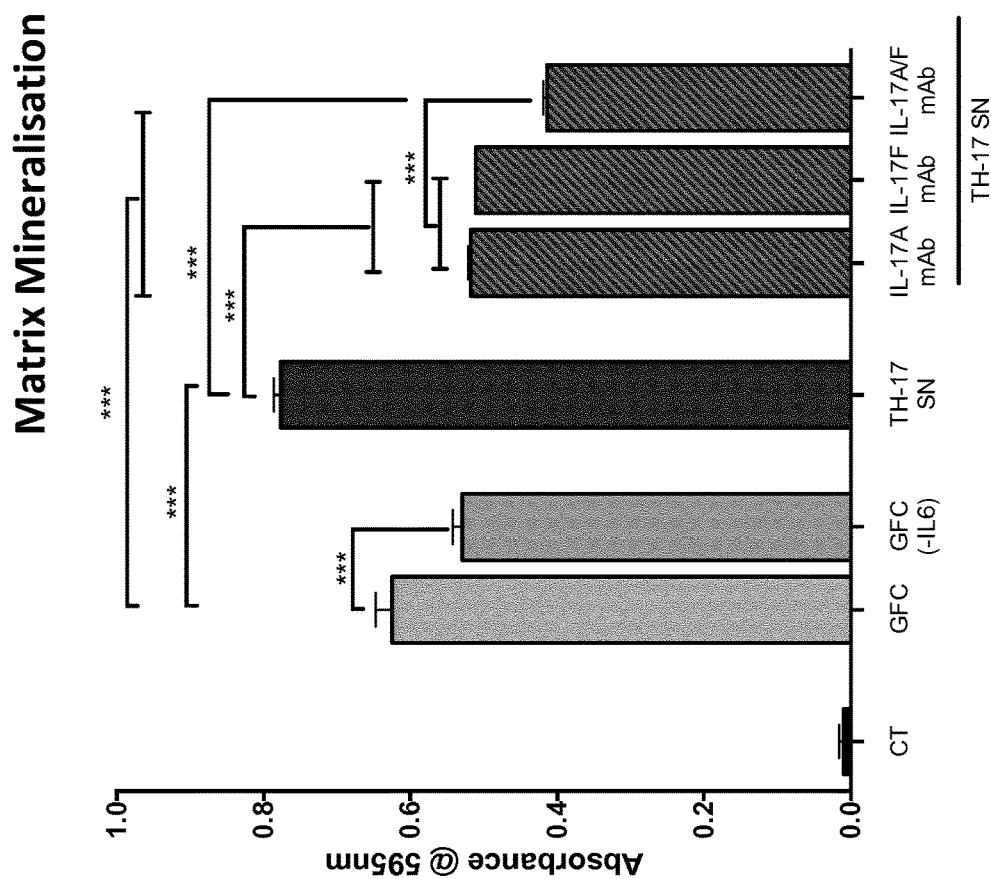

In one embodiment, the antibodies of the invention specifically bind to IL-17A. Specifically binding means that the antibodies have a greater affinity for IL-17A polypeptides than for other polypeptides.

In one embodiment, the antibodies of the invention specifically bind to IL-17F. Specifically binding means that the antibodies have a greater affinity for IL-17F polypeptides than for other polypeptides.

In a preferred embodiment, the antibodies of the invention specifically bind to IL-17A and IL-17F. Specifically binding means that the antibodies have a greater affinity for IL-17A and IL-17F polypeptides (including the IL-17A/IL-17F heterodimer) than for other polypeptides.

Preferably, the IL-17A and IL-17F polypeptides are human. In one embodiment, the antibody also binds cynomolgus IL-17A and/or IL-17F.

It will be appreciated that an antibody of the invention that neutralizes both IL-17A and IL-17F may be generated as a cross-reactive antibody as described herein below or by combining both an IL-17A binding domain with an IL-17F binding domain in a bispecific antibody.

In one embodiment, an antibody of the invention which is capable of binding to both IL-17A and IL-17F is capable of neutralising the activity of both isoforms of IL-17. Preferably, an antibody of the invention neutralises the activity of both IL-17A and IL-17F. In one embodiment, an antibody of the invention also neutralises the activity of the IL-17A/IL-17F heterodimer. The antibodies provided by this aspect of the invention therefore have the advantageous property that they can inhibit the biological activity of both IL-17A and IL-17F. Accordingly, the invention also provides the use of such antibodies in the treatment of and/or prophylaxis of a disease mediated by either or both of IL-17A or IL-17F such as autoimmune or inflammatory disease.

As used herein, the term "neutralising antibody" describes an antibody that is capable of neutralising the biological signalling activity of IL-17A and/or IL17F and/or IL-17A/F heterodimer, for example by blocking binding of IL-17A and/or IL17F to one or more of their receptors and by blocking binding of the IL-17A/IL-17F heterodimer to one or more of its receptors. It will be appreciated that the term "neutralizing" as used herein refers to a reduction in biological signalling activity which may be partial or complete. Further, it will be appreciated that the extent of neutralisation of IL-17A and IL-17F activity by an antibody which binds both IL-17A and IL-17F may be the same or different. In one embodiment, the extent of neutralisation of the activity of the IL-17A/IL-17F heterodimer may be the same or different as the extent of neutralisation of IL-17A or IL-17F activity.

IL-17A or IL-17F polypeptides, or a mixture of the two, or cells expressing one or both of said polypeptides, can be used to produce antibodies which specifically recognise one or both polypeptides. The IL-17 polypeptides (IL-17A and IL-17F) may be "mature" polypeptides or biologically active fragments or derivatives thereof which preferably include the receptor binding site. Preferably the IL-17 polypeptides are the mature polypeptides provided in SEQ ID NOs: 27 and 28 for IL-17A and IL-17F respectively. IL-17 polypeptides may be prepared by processes well known in the art from genetically engineered host cells comprising expression systems or they may be recovered from natural biological sources.

In the application, the term "polypeptides" includes peptides, polypeptides and proteins. These are used interchangeably unless otherwise specified.

The IL-17 polypeptide may in some instances be part of a larger protein such as a fusion protein for example fused to an affinity tag. Antibodies generated against these polypeptides may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warmblooded animals, such as rabbits, mice, rats, sheep, cows or pigs may be immunized. Mice, rabbits, pigs and rats may be preferred.

Antibodies for use in the invention include whole antibodies and functionally active fragments or derivatives thereof and may be, but are not limited to, monoclonal, multi-valent, multi-specific, bispecific, fully human, humanized or chimeric antibodies, domain antibodies e.g. VH, VL, VHH, single chain antibodies, Fab fragments, Fab' and F(ab')$_2$ fragments and epitope-binding fragments of any of the above. Other antibody fragments include those described in International patent applications WO2005003169, WO2005003170, WO2005003171, WO2009040562 and WO2010035012. Antibody fragments and methods of producing them are well known in the art, see for example Verma et al., 1998, Journal of Immunological Methods, 216, 165-181; Adair and Lawson, 2005. Therapeutic antibodies. *Drug Design Reviews—Online* 2(3):209-217.

Antibodies for use in the invention include immunoglobulin molecules and immunologically active portions of immunoglobulin molecules, i.e., molecules that contain an antigen binding site that specifically binds an antigen. The immunoglobulin molecules of the invention can be of any class (e.g. IgG, IgE, IgM, IgD and IgA) or subclass of immunoglobulin molecule.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanized antibodies are antibody molecules from non-human species having one or more complementarity determining regions (CDRs) from the non-human species and a framework region from a human immunoglobulin molecule (see, e.g. U.S. Pat. No. 5,585,089; WO91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multi-valent antibodies may comprise multiple specificities or may be monospecific (see for example WO 92/22853 and WO05/113605).

In one embodiment, the antibody provided by the invention is a monoclonal antibody. In one embodiment, the antibody provided by the invention is a humanized antibody. In one embodiment, the antibody provided by the invention is a chimeric antibody. The antibody molecules of the invention preferably comprise a complementary light chain or a complementary heavy chain, respectively.

The antibodies for use in the invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies which bind to IL-17A and IL-17F. Also, transgenic mice, or other organisms, including other mammals, may be used to express humanized antibodies, including those within the scope of the invention.

In one embodiment, the antibody provided by the invention is a CDR-grafted antibody molecule. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment, rather than the entire CDR being transferred, only one or more of the specificity determining residues from any one of the CDRs described herein above are transferred to the human antibody framework (see, for example, Kashmiri et al., 2005, Methods, 36, 25-34). In one embodiment, only the specificity determining residues from one or more of the CDRs described herein above are transferred to the human antibody framework. In another embodiment, only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Preferably, the CDR-grafted antibody according to the invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at, for example: http://vbase.mrc-cpe.cam.ac.uk/. In a CDR-grafted antibody of the invention, the acceptor heavy and light chains do not necessarily need to be derived from the same antibody and may, if desired, comprise composite chains having framework regions derived from different chains.

As described herein above, the antibody molecule of the invention may comprise a complete antibody molecule having full length heavy and light chains or a fragment thereof, such as a domain antibody e.g. VH, VL, VHH, Fab, modified Fab, Fab', F(ab')$_2$, Fv or scFv fragment.

It will be appreciated that the antibodies of the invention, in particular the antibody fragments described above, may be incorporated into other antibody formats, in particular, multi-specific antibodies, such as bi or tri specific antibodies, where specificity is provided by an antibody of the invention, i.e., specificity for IL-17A and IL-17F (including IL-17A/F heterodimer). Accordingly, in one embodiment, the invention provides a multi-specific antibody comprising one or more of the antibody fragments described herein above. Such multi-specific antibodies may comprise one or more further antibody fragments with binding specificity for another antigen, such as serum albumin, such as human serum albumin in order to extend the half life of the multi-specific antibody. For example, antibody fragments described in WO2012/156219 and combinations or variants thereof which comprise both an anti-IL-17A/F VHH binding domain and a serum albumin VHH binding domain.

Examples of multi-specific antibodies include bi, tri or tetra-valent antibodies, Bis-scFv, diabodies, triabodies, tetrabodies, bibodies and tribodies (see for example Holliger and Hudson, 2005, Nature Biotech 23(9): 1126-1136; Schoonjans et al. 2001, Biomolecular Engineering, 17 (6), 193-202). Other multi-specific antibodies include Fab-Fv, Fab-dsFv, Fab-Fv-Fv. Fab-Fv-Fc and Fab-dsFv-PEG fragments described in WO2009040562, WO2010035012, WO2011/08609, WO2011/030107 and WO2011/061492 respectively.

The constant region domains of the antibody molecule of the invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity. For example IgG4 molecules in which the serine at position 241 has been changed to proline as described in Angal et al., Molecular Immunology, 1993, 30 (1), 105-108 may be used. Particularly preferred is the IgG4 constant domain that comprises this change.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain, for example as given in FIG. 1 SEQ ID NO: 16, may be absent.

In one embodiment, the antibody heavy chain comprises a CH1 domain and the antibody light chain comprises a CL domain, either kappa or lambda.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts, e.g., as described in general terms in EP0546073 B1, U.S. Pat. Nos. 5,545,806, 5,569,825, 5,625,126, 5,633,425, 5,661,016, 5,770,429, EP 0438474 B1 and EP0463151 B1.

The above antibodies are described for purposes of reference and example only and do not limit the scope of invention.

Inhibitors of IL-17A and IL-17F activity are known in the art, for example those described herein. Antibodies which bind both IL-17A and IL-17F have been described in WO2007/106769, WO2008/047134, WO2009/136286, WO2010/025400, and WO2012/156219. IL-17A and IL-17F activity can also be antagonized through use of an anti-IL-17RC antibody or an IL-17RC fusion protein, as described in US2007196371A.

U.S. Pat. No. 8,303,953 (Oct. 18, 2006 priority date) describes a high affinity antibody, CA028_00496 which binds human IL-17A, IL-17F and IL-17A/F heterodimer, the sequence of which is provided herein in FIG. 1. CA028_0496 is a humanised neutralising antibody which comprises the grafted variable regions gL7 and gH9, the sequences of which are provided in U.S. Pat. No. 8,303,953 (priority date 18 Oct. 2006) and herein in FIG. 1. The heavy chain acceptor framework is the human germline sequence VH3 1-3 3-07 with framework 4 coming from this portion of the human JH-region germline JH4. The light chain acceptor framework is the human germline sequence VK1 2-1-(1) L4, with framework 4 coming from this portion of the human JK-region germline JK1. Examples 2-4 of U.S. Pat. No. 8,303,953, as well as the DNA Manipulations and General Methods section therein, describe characterization and testing of the neutralizing activity and affinity of CA028_0496.

U.S. Pat. No. 8,580,265 (Jan. 14, 2011 priority date) describes a second, higher affinity antibody, CA028_00496.g3, also known as UCB4940 or Bimekizumab, which binds human IL-17A, IL-17F and IL-17A/F heterodimer, the sequence of which is provided herein in FIG. 1. As described in U.S. Pat. No. 8,580,265, antibody CA028_0496 was affinity matured to improve the affinity of the antibody for IL-17F while retaining affinity for IL-17A. This affinity matured antibody, CA028_0496.g3 (also known as UCB4940 or bimekizumab), was expressed as an IgG1. The final sequence of the affinity matured variable regions of CA028_0496.g3 is given in FIGS. 1a and 1b of U.S. Pat. No. 8,580,265, and herein in FIG. 1. U.S. Pat. No. 8,679,494 (Apr. 23, 2008 priority date) provides novel neutralising epitopes on IL-17A and IL-17F and antibodies which bind to, and/or interact with, those epitopes, the sequences of which are provided herein in FIG. 1. The aforementioned patents are incorporated by reference as if fully set forth herein.

In antibody CA028_0496.g3, the heavy chain variable region sequence is the same as that of the parent antibody CA028_0496. In contrast, the light chain variable region differs by 5 amino acids. The five residues that differ between the light chain of antibody CA028_0496 and antibody CA028_0496.g3 are underlined in FIG. 1a of U.S. Pat. No. 8,580,265. Three residues were in the CDRs and two in the framework. Accordingly in one embodiment, the light chain variable domain comprises an arginine residue at position 30, a serine residue at position 54, an isoleucine residue at position 56, an aspartic acid residue at position 60 and an arginine residue at position 72.

Antibody CA028_0496.g3 selectively and potently inhibits the activity of both IL-17A and IL-17F isoforms in-vitro. Antibody CA028_0496.g3 binds to IL-17A, IL-17F and the IL-17A/F heterodimer and neutralizes the bioactivity of each cytokine by blocking the cytokines from signalling through the IL-17RA/RC complex.

Characterization of CA028_0496.g3 and CA028_0496 and their properties is described in Examples 2 and 3 of U.S. Pat. No. 8,580,265 as if fully set forth herein. As detailed in U.S. Pat. No. 8,580,265, biomolecular analysis of antibody CA028_0496.g3 was performed using the Biacore 3000 (Biacore AB). The assay format was a capture of the antibody CA028_0496.g3 by an immobilised anti-human IgG Fc-specific antibody, followed by the titration of recombinant human IL-17A or human IL-17F over the captured surface. Additional detail regarding surface plasmon resonance (Biacore) assays are as follows; while the details are described by referencing a particular antibody, the parameters described herein are suitable for use in characterizing any antibody described herein. Assays were performed at 25° C. Affinipure F(ab')$_2$ fragment goat anti-human IgG Fc specific (Jackson ImmunoResearch) was immobilised on a CM5 Sensor Chip (Biacore AB) via amine coupling chemistry to a level of approximately 6000 response units (RU). HBS-EP buffer (10 mM HEPES pH7.4, 0.15M NaCl, 3 mM EDTA, 0.005% Surfactant P20, Biacore AB) was used as the running buffer with a flow rate of 10 microL/minute (min). A 10 µL injection of CA028_00496.g3 at 0.5 µg/mL was used for capture by the immobilised anti-human IgG Fc. Human IL-17A was titrated over the captured CA028_00496.g3 from 5 nM at a flow rate of 30 µL/min for 3 min followed by a 20 min dissociation. Human IL-17F (R&D systems) was titrated over the captured CA028_00496.g3 from 10 nM at a flow rate of 30 µL/min for 3 min followed by a 5 min dissociation. The surface was regenerated at a flow rate of 10 µL/min by a 10 µL injection of 40 mM HCl followed by a 5 µL injection of 5 mM NaOH. Double referenced background subtracted binding curves were analysed using the BIA evaluation software (version 4.1) following standard procedures. Kinetic parameters were determined from the fitting algorithm.

Data are detailed in Table 1.

TABLE 1

Affinity of bimekizumab against human IL-17F and IL-17A.

|  | ka (M-1s-1) | kd (s-1) | KD (M) | KD (pM) |
|---|---|---|---|---|
| hIL-17F | 2.49E+06 | 8.74E−05 | 3.51E−11 | 35 |
|  | 3.49E+06 | 5.08E−05 | 1.46E−11 | 15 |
|  | 2.99E+06 | 6.91E−05 | 2.31E−11 | 23 |
| hIL-17A | 4.66E+06 | 2.04E−05 | 4.38E−12 | 4.4 |
|  | 4.52E+06 | 8.66E−06 | 1.92E−12 | 1.9 |
|  | 4.59E+06 | 1.45E−05 | 3.17E−12 | 3.2 |

As described in U.S. Pat. No. 8,580,265, the preferred framework region for the heavy chain of CA028_0496.g3 is derived from the human sub-group VH3 sequence 1-3 3-07 together with JH4, as previously described in WO2008/047134. Accordingly, an embodiment of the invention may be a neutralising CDR-grafted antibody comprising at least one non-human donor CDR wherein the heavy chain framework region is derived from the human subgroup sequence 1-3 3-07 together with JH4. The sequence of human JH4 is as follows: (YFDY)WGQGTLVTVSS. The YFDY motif is part of CDR-H3 and is not part of framework 4 (Ravetch, J V. et al., 1981, Cell, 27, 583-591).

As described in U.S. Pat. No. 8,580,265, the preferred framework region for the light chain of CA028_0496.g3 is derived from the human germline sub-group VK1 sequence 2-1-(1) L4 together with JK1, as previously described in WO2008/047134. Accordingly, an embodiment of the invention may be a neutralising CDR-grafted antibody comprising at least one non-human donor CDR wherein the light chain framework region is derived from the human subgroup sequence VK1 2-1-(1) L4 together with JK1. The JK1 sequence is as follows: (WT)FGQGTKVEIK. The WT motif is part of CDR-L3 and is not part of framework 4 (Hieter, P A., et al., 1982, J. Biol. Chem., 257, 1516-1522).

Also, in CA028_0496.g3, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

In one embodiment, in CA028_0496.g3, if the acceptor heavy chain has the human VH3 sequence 1-3 3-07 together with JH4, then the acceptor framework regions of the heavy chain comprise, in addition to one or more donor CDRs, a donor residue at least position 94 (according to Kabat et al., (supra)). Accordingly, an embodiment of the invention may be a CDR-grafted antibody, wherein at least the residue at position 94 of the variable domain of the heavy chain is a donor residue.

In one embodiment, in CA028_0496.g3, if the acceptor light chain has the human sub-group VK1 sequence 2-1-(1) L4 together with JK1, then no donor residues are transferred i.e. only the CDRs are transferred. Accordingly, an embodiment of the invention may be a CDR-grafted antibody wherein only the CDRs are transferred to the donor framework.

Donor residues are residues from the donor antibody, i.e. the antibody from which the CDRs were originally derived.

Antibody CA028_0496.g3 is not pharmacologically active in rodents as it does not bind to either IL-17A or IL-17F from rat or mouse. Antibody CA028_0496.g3 has been shown to bind to IL-17A and IL-17F in the cynomolgus monkey and nonclinical evaluation demonstrates it to be pharmacologically active in vivo in the cynomolgus monkey. In humans, antibody CA028_0496.g3 displays a long half-life in a dose-proportional manner, with PK for doses between 8 mg and 640 mg ranging between 17.00 days and 25.55 days (e.g., 23.6 days) across the treatment groups.

The above antibodies are described for purposes of reference and example only and do not limit the scope of invention. For example, as described herein, it will be appreciated that the affinity of antibodies provided by the invention may be altered using any suitable method known in the art. The invention therefore also relates to variants of the antibody molecules of the invention, which have an improved affinity for IL-17A and/or IL-17F. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

Screening for antibodies can be performed using assays to measure binding to human IL-17A and human IL-17F, for example BIAcore™ assays. BIAcore™ (i.e., surface plasmon resonance assays) are described herein. Suitable neutralisation assays are known in the art, see for example WO2008/047134. An exemplary cell-based neutralization assay utilizes HeLa cells. For example, HeLa cells are grown in Dulbecco's modified Eagle's medium (DMEM) supplemented with 10% foetal calf serum, penicillin, gentamycin and glutamine. $1 \times 10^4$ cells are plated out into 96 well flat bottomed tissue culture plates. Cells are incubated overnight and washed once in assay buffer. HeLa cells are stimulated with a combination of recombinant human IL-17F (125 ng/ml) or human IL-17A (25 ng/ml) and tumour necrosis factor-alpha (TNF-α) (1 ng/ml) for 48 hours in the presence of varying concentrations of candidate antibody. In the HeLa cell line, IL-17A or IL-17F synergises with TNF-alpha to induce the production of IL-6, which can be quantified using a specific MSD assay kit. The resulting amount of secreted IL-6 is measured using Meso Scale Discovery (MSD) assay technology and IC50 values calculated. The activity of an antibody can be expressed as the dose required to inhibit 50% of the activity of IL-17A or IL-17F ($IC_{50}$).

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment, the antibody provided by the invention is a CDR-grafted antibody molecule comprising one or more of the CDRs provided in SEQ ID NOs:1 to 8.

In one embodiment, the invention provides a neutralising antibody having specificity for human IL-17A and human IL-17F, comprising a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3.

In one embodiment, the invention provides a neutralising antibody having specificity for human IL-17A and human IL-17F, comprising a light chain, wherein the variable domain of the light chain comprises the sequence given in SEQ ID NO:4 or SEQ ID NO:7 for CDR-L1, the sequence given in SEQ ID NO:5 or SEQ ID NO:8 for CDR-L2 and the sequence given in SEQ ID NO:6 for CDR-L3.

It will be appreciated that one or more amino acid substitutions may be made to the CDRs provided by the invention without significantly altering the ability of the antibody to bind to IL-17A and IL-17F and to neutralise IL-17A and IL-17F activity. The effect of any amino acid substitutions on binding and neutralisation can be readily tested by one skilled in the art, for example by using the methods described herein. Accordingly, the invention provides an antibody comprising one or more CDRs selected from CDR-H1 (SEQ ID NO:1), CDR-H2 (SEQ ID NO:2), CDR-H3 (SEQ ID NO:3), CDR-L1 (SEQ ID NO:4 or SEQ ID NO:7), CDR-L2 (SEQ ID NO:5 or SEQ ID NO:8) and CDR-L3 (SEQ ID NO:6) in which one or more amino acids in one or more of the CDRs has been substituted with another amino acid. It will also be appreciated that the length of one or more of the CDRs may be altered without significantly altering the ability of the antibody to bind to IL-17A and IL-17F and to neutralise IL-17A and IL-17F activity.

In another embodiment, the invention provides a neutralising antibody having specificity for human IL-17A and human IL-17F, comprising a heavy chain, wherein at least two of CDR-H1, CDR-H2 and CDR-H3 of the variable domain of the heavy chain are selected from the following: the sequence given in SEQ ID NO:1 for CDR-H1, the sequence given in SEQ ID NO:2 for CDR-H2 and the sequence given in SEQ ID NO:3 for CDR-H3. For example, the antibody may comprise a heavy chain wherein CDR-H1 has the sequence given in SEQ ID NO:1 and CDR-H2 has the sequence given in SEQ ID NO:2. Alternatively, the antibody may comprise a heavy chain wherein CDR-H1 has the sequence given in SEQ ID NO:1 and CDR-H3 has the sequence given in SEQ ID NO:3, or the antibody may comprise a heavy chain wherein CDR-H2 has the sequence given in SEQ ID NO:2 and CDR-H3 has the sequence given in SEQ ID NO:3. For the avoidance of doubt, it is understood that all permutations are included.

In another embodiment, the invention provides a neutralising antibody having specificity for human IL-17A and human IL-17F, comprising a light chain, wherein at least two of CDR-L1, CDR-L2 and CDR-L3 of the variable domain of the light chain are selected from the following: the sequence given in SEQ ID NO:4 or SEQ ID NO:7 for CDR-L1, the sequence given in SEQ ID NO:5 or 8 for CDR-L2 and the sequence given in SEQ ID NO:6 for CDR-L3. For example, the antibody may comprise a light chain wherein CDR-L1 has the sequence given in SEQ ID NO:4 and CDR-L2 has the sequence given in SEQ ID NO:5. Alternatively, the antibody may comprise a light chain wherein CDR-L1 has the sequence given in SEQ ID NO:4 and CDR-L3 has the sequence given in SEQ ID NO:6, or the antibody may comprise a light chain wherein CDR-L2 has the sequence given in SEQ ID NO:5 and CDR-L3 has the sequence given in SEQ ID NO:6. For the avoidance of doubt, it is understood that all permutations are included.

In one embodiment, an antibody according to the invention comprises a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and a light chain wherein the variable domain of the light chain comprises the sequence given in SEQ ID NO:4 for CDR-L1, the sequence given in SEQ ID NO:5 for CDR-L2 and the sequence given in SEQ ID NO:6 for CDR-L3.

In one embodiment, an antibody according to the invention comprises a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and a light chain wherein the variable domain of the light chain comprises the sequence given in SEQ ID NO:7 for CDR-L1, the sequence given in SEQ ID NO:8 for CDR-L2 and the sequence given in SEQ ID NO:6 for CDR-L3.

In one embodiment, an antibody of the invention comprises a heavy chain, wherein the variable domain of the heavy chain comprises three CDRs wherein the sequence of CDR-H1 has at least 60% identity or similarity to the sequence given in SEQ ID NO:1, CDR-H2 has at least 60% identity or similarity to the sequence given in SEQ ID NO:2 and/or CDR-H3 has at least 60% identity or similarity to the sequence given in SEQ ID NO:3. In another embodiment, an antibody of the invention comprises a heavy chain, wherein the variable domain of the heavy chain comprises three CDRs wherein the sequence of CDR-H1 has at least 70%, 80%, 90%, 95% or 98% identity or similarity to the sequence given in SEQ ID NO:1, CDR-H2 has at least 70%, 80%, 90%, 95% or 98% identity or similarity to the sequence given in SEQ ID NO:2 and/or CDR-H3 has at least 70%, 80%, 90%, 95% or 98% identity or similarity to the sequence given in SEQ ID NO:3.

In another embodiment, an antibody of the invention comprises a light chain, wherein the variable domain of the light chain comprises three CDRs wherein the sequence of CDR-L1 has at least 60% identity or similarity to the sequence given in SEQ ID NO:4, CDR-L2 has at least 60% identity or similarity to the sequence given in SEQ ID NO:5 and/or CDR-L3 has at least 60% identity or similarity to the sequence given in SEQ ID NO:6. In another embodiment, an antibody of the invention comprises a light chain, wherein the variable domain of the heavy chain comprises three CDRs wherein the sequence of CDR-L1 has at least 70%, 80%, 90%, 95% or 98% identity or similarity to the sequence given in SEQ ID NO:4, CDR-L2 has at least 70%, 80%, 90%, 95% or 98% identity or similarity to the sequence given in SEQ ID NO:5, and/or CDR-L3 has at least 70%, 80%, 90%, 95% or 98% identity or similarity to the sequence given in SEQ ID NO:6.

In another embodiment, an antibody of the invention comprises a light chain, wherein the variable domain of the light chain comprises three CDRs wherein the sequence of CDR-L1 has at least 60% identity or similarity to the sequence given in SEQ ID NO:4, CDR-L2 has at least 60% identity or similarity to the sequence given in SEQ ID NO:5 and/or CDR-L3 has at least 60% identity or similarity to the sequence given in SEQ ID NO:6. In another embodiment, an antibody of the invention comprises a light chain, wherein the variable domain of the heavy chain comprises three CDRs wherein the sequence of CDR-L1 has at least 70%, 80%, 90%, 95% or 98% identity or similarity to the sequence given in SEQ ID NO:7, CDR-L2 has at least 70%, 80%, 90%, 95% or 98% identity or similarity to the sequence given in SEQ ID NO:8, and/or CDR-L3 has at least 70%, 80%, 90%, 95% or 98% identity or similarity to the sequence given in SEQ ID NO:6.

In one embodiment, an antibody of the invention comprises a light chain, wherein the variable domain of the light chain comprises the sequence given in SEQ ID NO:9 (gL7).

In another embodiment, an antibody of the invention comprises a light chain, wherein the variable domain of the light chain comprises a sequence having at least 60% identity or similarity to the sequence given in SEQ ID NO:9. In one embodiment, the antibody of the invention comprises a light chain, wherein the variable domain of the light chain comprises a sequence having at least 70%, 80%, 90%, 95% or 98% identity or similarity to the sequence given in SEQ ID NO:9.

In one embodiment, an antibody of the invention comprises a light chain, wherein the variable domain of the light chain comprises the sequence given in SEQ ID NO:10 (gL57).

In another embodiment, an antibody of the invention comprises a light chain, wherein the variable domain of the light chain comprises a sequence having at least 60% identity or similarity to the sequence given in SEQ ID NO:10. In one embodiment, the antibody of the invention comprises a light chain, wherein the variable domain of the light chain comprises a sequence having at least 70%, 80%, 90%, 95% or 98% identity or similarity to the sequence given in SEQ ID NO:10.

In one embodiment, an antibody of the invention comprises a heavy chain, wherein the variable domain of the heavy chain comprises the sequence given in SEQ ID NO:11 (gH9).

In another embodiment, an antibody of the invention comprises a heavy chain, wherein the variable domain of the heavy chain comprises a sequence having at least 60% identity or similarity to the sequence given in SEQ ID NO:11. In one embodiment, an antibody of the invention comprises a heavy chain, wherein the variable domain of the heavy chain comprises a sequence having at least 70%, 80%, 90%, 95%, 96, 97, 98 or 99% identity or similarity to the sequence given in SEQ ID NO:11.

In one embodiment, an antibody of the invention comprises a heavy chain, wherein the variable domain of the heavy chain comprises the sequence given in SEQ ID NO:11 and a light chain, wherein the variable domain of the light chain comprises the sequence given in SEQ ID NO:9.

In another embodiment of the invention, the antibody comprises a heavy chain and a light chain, wherein the variable domain of the heavy chain comprises a sequence having at least 60% identity or similarity to the sequence given in SEQ ID NO:11 and the variable domain of the light chain comprises a sequence having at least 60% identity or similarity to the sequence given in SEQ ID NO:9. Preferably, the antibody comprises a heavy chain, wherein the variable domain of the heavy chain comprises a sequence having at least 70%, 80%, 90%, 95%, 96%, 97%, 98 or 99% identity or similarity to the sequence given in SEQ ID NO:11 and a light chain, wherein the variable domain of the light chain comprises a sequence having at least 70%, 80%, 90%, 95% 96, 97, 98 or 99% identity or similarity to the sequence given in SEQ ID NO:9.

In one embodiment, an antibody of the invention comprises a heavy chain, wherein the variable domain of the heavy chain comprises the sequence given in SEQ ID NO:11 and a light chain, wherein the variable domain of the light chain comprises the sequence given in SEQ ID NO:10.

In another embodiment of the invention, the antibody comprises a heavy chain and a light chain, wherein the variable domain of the heavy chain comprises a sequence having at least 60% identity or similarity to the sequence given in SEQ ID NO:11 and the variable domain of the light chain comprises a sequence having at least 60% identity or similarity to the sequence given in SEQ ID NO:10. Preferably, the antibody comprises a heavy chain, wherein the variable domain of the heavy chain comprises a sequence having at least 70%, 80%, 90%, 95%, 96%, 97%, 98 or 99% identity or similarity to the sequence given in SEQ ID NO:11 and a light chain, wherein the variable domain of the light chain comprises a sequence having at least 70%, 80%, 90%, 95% 96, 97, 98 or 99% identity or similarity to the sequence given in SEQ ID NO:10.

In a preferred embodiment the antibody provided by the invention is a neutralising antibody having specificity for human IL-17A and human IL-17F in which the heavy chain constant region comprises the human IgG1 constant region. Accordingly, the invention provides an antibody in which the heavy chain comprises or consists of the sequence given in SEQ ID NO:15.

In one embodiment, of the invention, the antibody comprises a heavy chain, wherein the heavy chain comprises a sequence having at least 60% identity or similarity to the sequence given in SEQ ID NO:15. Preferably, the antibody comprises a heavy chain, wherein the heavy chain comprises a sequence having at least 70%, 80%, 90%, 95%, 97%, 98%, or 99% identity or similarity to the sequence given in SEQ ID NO:15.

In one embodiment, an antibody molecule according to the invention comprises a light chain comprising the sequence given in SEQ ID NO:12.

In one embodiment, of the invention, the antibody comprises a light chain, wherein the light chain comprises a sequence having at least 60% identity or similarity to the sequence given in SEQ ID NO:12. Preferably, the antibody comprises a light chain, wherein the light chain comprises a sequence having at least 70%, 80%, 90%, 95% or 98% identity or similarity to the sequence given in SEQ ID NO:12.

In one embodiment, the invention provides an antibody in which the heavy chain comprises or consists of the sequence given in SEQ ID NO:15, and the light chain comprises or consists of the sequence given in SEQ ID NO:12.

In one embodiment, of the invention, the antibody comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:12. Preferably, the antibody comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:12.

In a preferred embodiment the antibody provided by the invention is a neutralising antibody having specificity for human IL-17A and human IL-17F in which the heavy chain constant region comprises the human IgG1 constant region. Accordingly, the invention provides an antibody in which the heavy chain comprises or consists of the sequence given in SEQ ID NO:16.

In one embodiment, of the invention, the antibody comprises a heavy chain, wherein the heavy chain comprises a sequence having at least 60% identity or similarity to the sequence given in SEQ ID NO:16. Preferably, the antibody comprises a heavy chain, wherein the heavy chain comprises a sequence having at least 70%, 80%, 90%, 95%, 97%, 98%, or 99% identity or similarity to the sequence given in SEQ ID NO:16.

In one embodiment, an antibody molecule according to the invention comprises a light chain comprising the sequence given in SEQ ID NO:13.

In one embodiment, of the invention, the antibody comprises a light chain, wherein the light chain comprises a sequence having at least 60% identity or similarity to the sequence given in SEQ ID NO:13. Preferably, the antibody comprises a light chain, wherein the light chain comprises a sequence having at least 70%, 80%, 90%, 95% or 98% identity or similarity to the sequence given in SEQ ID NO:13.

In one embodiment, the invention provides an antibody in which the heavy chain comprises or consists of the sequence given in SEQ ID NO:16 and the light chain comprises or consists of the sequence given in SEQ ID NO:13.

In one embodiment, of the invention, the antibody comprises a heavy chain and a light chain, wherein the heavy chain comprises a sequence having at least 60% identity or similarity to the sequence given in SEQ ID NO:16 and the light chain comprises a sequence having at least 60% identity or similarity to the sequence given in SEQ ID NO:13. Preferably, the antibody comprises a heavy chain, wherein the heavy chain comprises a sequence having at least 70%, 80%, 90%, 95% or 98% identity or similarity to the sequence given in SEQ ID NO:16 and a light chain, wherein the light chain comprises a sequence having at least 70%, 80%, 90%, 95% or 98% identity or similarity to the sequence given in SEQ ID NO:13.

In one embodiment, the invention provides an antibody in which the heavy chain comprises or consists of the sequence given in SEQ ID NO:15 and the light chain comprises or consists of the sequence given in SEQ ID NO:13.

In one embodiment, of the invention, the antibody comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:13. Preferably, the antibody comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:13.

In one embodiment, the invention provides an antibody in which the heavy chain comprises or consists of the sequence given in SEQ ID NO:16 and the light chain comprises or consists of the sequence given in SEQ ID NO:12.

In one embodiment, of the invention, the antibody comprises a heavy chain and a light chain, wherein the heavy chain comprises a sequence having at least 60% identity or similarity to the sequence given in SEQ ID NO:16 and the light chain comprises a sequence having at least 60% identity or similarity to the sequence given in SEQ ID NO:12. Preferably, the antibody comprises a heavy chain, wherein the heavy chain comprises a sequence having at least 70%, 80%, 90%, 95% or 98% identity or similarity to the sequence given in SEQ ID NO:16 and a light chain, wherein the light chain comprises a sequence having at least 70%, 80%, 90%, 95% or 98% identity or similarity to the sequence given in SEQ ID NO:12.

Binding Affinity

The neutralising antibody molecule of any aspect of the invention preferably has a high binding affinity, preferably nanomolar, even more preferably picomolar. It will be appreciated that the binding affinity of an antibody according to the invention for human IL-17A may be different from the binding affinity of the same antibody for human IL-17F and/or the IL-17A/F heterodimer.

In one example, the antibody molecule of the invention has an affinity for IL-17A that is greater than its affinity for IL-17F. In one example, the antibody molecule of the invention has an affinity for IL-17A which is at least 10 fold greater than its binding affinity for IL-17F. In one example, the antibody molecule of the invention has an affinity for IL-17A which is at least 50 fold greater than its binding affinity for IL-17F. In one example, the antibody molecule of the invention has an affinity for IL-17A which is at least 100 fold greater than its binding affinity for IL-17F. In one example, the antibody molecule of the invention has a nanomolar affinity for IL-17F and a picomolar affinity for IL-17A.

In one example, the antibody molecule of the invention has an affinity for IL-17F that is greater than its affinity for IL-17A. In one example, the antibody molecule of the invention has an affinity for IL-17F which is at least 10 fold greater than its binding affinity for IL-17A. In one example, the antibody molecule of the invention has an affinity for IL-17F which is at least 50 fold greater than its binding affinity for IL-17A. In one example, the antibody molecule of the invention has an affinity for IL-17F which is at least 100 fold greater than its binding affinity for IL-17A. In one example, the antibody molecule of the invention has a picomolar affinity for IL-17A and a nanomolar affinity for IL-17F.

In one example, the antibody molecule of the invention has an affinity for IL-17A that is the same as its affinity for IL-17F. In one example, the antibody molecule of the invention has a nanomolar affinity for both IL-17A and IL-17F. In one example, the antibody molecule of the invention has a picomolar affinity for both IL-17A and IL-17F.

Affinity may be measured using any suitable method known in the art, including BIAcore™ using isolated natural or recombinant IL-17A and IL-17F which both exist as homodimers.

Preferably the antibody molecule of the invention has a binding affinity for IL-17A of less than 10 nM. In one embodiment, the antibody molecule of the invention has a binding affinity for IL-17A of less than 500 pM. In one embodiment, the antibody molecule of the invention has a binding affinity for IL-17A of 100 pM or less. In one embodiment, the antibody molecule of the invention has a binding affinity for IL-17A of 20 pM or less. In one embodiment, the antibody of the invention has an affinity for IL-17A of 16 pM. In one embodiment, the antibody molecule of the invention has a binding affinity for IL-17A of 10 pM or less. In one embodiment, the antibody molecule of the invention has a binding affinity for IL-17A of 5 pM or less. In one embodiment, the antibody of the invention has an affinity for IL-17A of 3.2 pM.

Preferably the antibody molecule of the invention has a binding affinity for IL-17F of less than 10 nM. In one embodiment, the antibody of the invention has an affinity for IL-17F of less than 2 nM. In one embodiment, the antibody of the invention has an affinity for IL-17F of 1.75 nM.

In one embodiment, the antibody of the invention has an affinity for IL-17F of less than 500 pM. In one embodiment, the antibody molecule of the invention has a binding affinity for IL-17F of 100 pM or less. In one embodiment, the antibody of the invention has an affinity for IL-17F of 50 pM or less. In one embodiment, the antibody of the invention has an affinity for IL-17F of 23 pM. In one embodiment, the antibody molecule of the invention has a binding affinity for IL-17F of 10 pM or less. In one embodiment, the antibody molecule of the invention has a binding affinity for IL-17F of 5 pM or less.

Preferably the antibody molecule of the invention has a binding affinity for IL-17A/F heterodimer of 10 nM or less. In one embodiment, the antibody molecule of the invention has a binding affinity for IL-17A/F heterodimer of 500 pM or less. In one embodiment, the antibody molecule of the invention has a binding affinity for IL-17A/F heterodimer of 150 pM or less. In one embodiment, the antibody molecule of the invention has a binding affinity for IL-17A/F heterodimer of 116 pM. In one embodiment, the antibody molecule of the invention has a binding affinity for IL-17A/F heterodimer of better than 100 pM. In one embodiment, the antibody molecule of the invention has a binding affinity for IL-17A/F heterodimer of 10 pM or less. In one embodiment, the antibody molecule of the invention has a binding affinity for IL-17A/F heterodimer of 5 pM or less.

In one embodiment, the antibody molecule of the invention has a binding affinity for cynomolgus IL-17F of less than 2 nM. In one embodiment, the antibody molecule of the invention has a binding affinity for cynomolgus IL-17F of 1.03 nM.

Cross-Blocking Antibodies

Antibodies which cross-block the binding of an antibody according to the invention, in particular, an antibody comprising the heavy chain sequence gH9 (SEQ ID NO:11) and the light chain sequence gL57 (SEQ ID NO:10) or the light chain sequence gL7 (SEQ ID NO:9), is useful in neutralising IL-17A and IL-17F activity. Accordingly, the invention also provides a neutralising antibody which binds human IL-17A and human IL-17F, which cross-blocks the binding of any one of the antibodies described above to human IL-17A and/or human IL-17F and/or human IL-17A/F heterodimer and/or is cross-blocked from binding IL-17A and/or IL-17F and/or human IL-17A/F heterodimer by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the invention or an epitope that borders and/or overlaps with said epitope.

Cross-blocking antibodies can be identified using any suitable method in the art, for example by using competition ELISA or BIAcore where binding of the cross blocking antibody to human IL-17A and/or human IL-17F prevents the binding of an antibody of the invention or vice versa. For surface plasmon resonance (BIAcore), target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560 65 (1993)). Conditions suitable for surface plasmon resonance (BIAcore) assays are known in the art and described elsewhere herein.

ELISA-based methods for determining cross-blocking also are well known in the art. A non-limiting, exemplary assay format suitable for both IL-17A and IL-17F is as follows, illustrated with IL-17A. An anti-IL-17A/F antibody (Ab-1) is coated (e.g., 50 µL of 1 µg/ml) onto a 96-well ELISA plate [e.g. Corning 96 Well EIA/RIA Flat Bottom Microplate (Product #3590), Corning Inc., Acton, Mass.] for at least one hour. After this coating step the antibody solution is removed, the plate is washed once or twice with wash solution (e.g., PBS and 0.05% Tween 20) and is then blocked using an appropriate blocking solution (e.g., PBS, 1% BSA, 1% goat serum and 0.5% Tween 20) and procedures known in the art. Blocking solution is then removed from the ELISA plate and a second anti-IL17A/F antibody (Ab-2), which is being tested for its ability to cross-block the coated antibody, is added in excess (e.g., 50 µl of 10 µg/ml) in blocking solution to the appropriate wells of the ELISA plate. Following this, a limited amount (e.g. 50 µl of 10 ng/ml) of IL-17A in blocking solution is then added to the appropriate wells and the plate is incubated for at least one hour at room temperature while shaking. The plate is then washed 2-4 times with wash solution. An appropriate amount of a IL-17A detection reagent [e.g., biotinylated anti-IL-17 polyclonal antibody that has been pre-complexed with an appropriate amount of a streptavidin-horseradish peroxidase (HRP) conjugate] in blocking solution is added to the ELISA plate and incubated for at least one hour at room temperature. The plate is then washed with wash solution and is developed with an appropriate reagent [e.g. HRP substrates such as TMB (colorimetric) or various HRP luminescent substrates]. The background signal for the assay is defined as the signal obtained in wells with the coated antibody (in this case Ab-1), second solution phase antibody (in this case Ab-2), IL-17A buffer only (i.e., no IL-17A) and IL-17A detection reagents. The positive control signal for the assay is defined as the signal obtained in wells with the coated antibody (in this case Ab-1), second solution phase antibody buffer only (i.e. no second solution phase antibody), IL-17A and IL-17A detection reagents. Preferably, the ELISA assay is run in such a manner so as to have the positive control signal be at least six times the background signal.

In one embodiment, there is provided a neutralising antibody which binds to human IL-17A and human IL-17F, which cross-blocks the binding of an antibody whose heavy chain comprises the sequence gH9 (SEQ ID NO:11) and whose light chain comprises the sequence gL57 (SEQ ID NO:10) to human IL-17A and to human IL-17F. In one embodiment, the cross-blocking antibodies provided by the invention inhibit the binding of an antibody comprising the heavy chain sequence gH9 (SEQ ID NO:11) and the light chain sequence gL57 (SEQ ID NO:10) to IL-17A by greater than 80%, preferably by greater than 85%, more preferably by greater than 90%, even more preferably by greater than 95% and to IL-17F by greater than 80%, preferably by greater than 85%, more preferably by greater than 90%, even more preferably by greater than 95%.

In one embodiment, there is provided a neutralising antibody which binds to human IL-17A and human IL-17F, which cross-blocks the binding of an antibody whose heavy chain comprises the sequence gH9 (SEQ ID NO:11) and whose light chain comprises the sequence gL7 (SEQ ID NO:9) to human IL-17A and to human IL-17F. In one embodiment, the cross-blocking antibodies provided by the invention inhibit the binding of an antibody comprising the heavy chain sequence gH9 (SEQ ID NO:11) and the light chain sequence gL7 (SEQ ID NO:9) to IL-17A by greater than 80%, preferably by greater than 85%, more preferably by greater than 90%, even more preferably by greater than 95% and to IL-17F by greater than 80%, preferably by greater than 85%, more preferably by greater than 90%, even more preferably by greater than 95%.

In one embodiment, there is provided a neutralising antibody which binds to human IL-17A and human IL-17F, which cross-blocks the binding of an antibody whose heavy chain comprises the sequence gH9 (SEQ ID NO:11) and whose light chain comprises the gL57 (SEQ ID NO:10) to human IL-17A and to human IL-17F and to human IL-17A/F heterodimer. In one embodiment, the cross-blocking antibodies provided by the invention inhibit the binding of an antibody comprising the heavy chain sequence gH9 (SEQ ID NO:11) and the light chain sequence gL57 (SEQ ID NO:10) to IL-17A by greater than 80%, preferably by greater than 85%, more preferably by greater than 90%, even more preferably by greater than 95% and to IL-17F by greater than 80%, preferably by greater than 85%, more preferably by greater than 90%, even more preferably by greater than 95% and to IL-17A/F heterodimer to IL-17F by greater than 80%, preferably by greater than 85%, more preferably by greater than 90%, even more preferably by greater than 95%.

In one embodiment, there is provided a neutralising antibody which binds to human IL-17A and human IL-17F, which cross-blocks the binding of an antibody whose heavy chain comprises the sequence gH9 (SEQ ID NO:11) and whose light chain comprises the gL7 (SEQ ID NO:9) to human IL-17A and to human IL-17F and to human IL-17A/F heterodimer. In one embodiment, the cross-blocking antibodies provided by the invention inhibit the binding of an antibody comprising the heavy chain sequence gH9 (SEQ ID NO:11) and the light chain sequence gL7 (SEQ ID NO:9) to IL-17A by greater than 80%, preferably by greater than 85%, more preferably by greater than 90%, even more preferably by greater than 95% and to IL-17F by greater than 80%, preferably by greater than 85%, more preferably by greater than 90%, even more preferably by greater than 95% and to IL-17A/F heterodimer to IL-17F by greater than 80%, preferably by greater than 85%, more preferably by greater than 90%, even more preferably by greater than 95%.

In one embodiment, there is provided a neutralising antibody which binds to human IL-17A and human IL-17F, which cross-blocks the binding of an antibody whose heavy chain comprises the sequence gH9 (SEQ ID NO:11) and whose light chain comprises the sequence gL57 (SEQ ID NO:10) to human IL-17A or to human IL-17F or human IL-17A/F heterodimer. In one embodiment, the cross-blocking antibodies provided by the invention inhibit the binding of an antibody comprising the heavy chain sequence gH9 (SEQ ID NO:11) and the light chain sequence gL57 (SEQ ID NO:10) to IL-17A or IL-17F or IL-17A/F by greater than 80%, preferably by greater than 85%, more preferably by greater than 90%, even more preferably by greater than 95%.

In one embodiment, there is provided a neutralising antibody which binds to human IL-17A and human IL-17F, which cross-blocks the binding of an antibody whose heavy chain comprises the sequence gH9 (SEQ ID NO:11) and whose light chain comprises the sequence gL7 (SEQ ID NO:9) to human IL-17A or to human IL-17F or human IL-17A/F heterodimer. In one embodiment, the cross-blocking antibodies provided by the invention inhibit the binding of an antibody comprising the heavy chain sequence gH9 (SEQ ID NO:11) and the light chain sequence gL7 (SEQ ID NO:9) to IL-17A or IL-17F or IL-17A/F by greater than 80%, preferably by greater than 85%, more preferably by greater than 90%, even more preferably by greater than 95%.

Alternatively or in addition, neutralising antibodies according to this aspect of the invention may be cross-blocked from binding to human IL-17A and human IL-17F by an antibody comprising the heavy chain sequence gH9 (SEQ ID NO:11) and the light chain sequence gL57 (SEQ ID NO:10). Also provided therefore is a neutralising antibody molecule which binds to human IL-17A and to human IL-17F which is cross-blocked from binding human IL-17A and human IL-17F by an antibody comprising the heavy chain sequence gH9 (SEQ ID NO:11) and the light chain sequence gL57 (SEQ ID NO:10). In one embodiment, the neutralising antibodies provided by this aspect of the invention are inhibited from binding to human IL-17A and human IL-17F by an antibody comprising the heavy chain sequence gH9 (SEQ ID NO:11) and the light chain sequence gL57 (SEQ ID NO:10) by greater than 80%, preferably by greater than 85%, more preferably by greater than 90%, even more preferably by greater than 95%.

Alternatively or in addition, neutralising antibodies according to this aspect of the invention may be cross-blocked from binding to human IL-17A and human IL-17F by an antibody comprising the heavy chain sequence gH9 (SEQ ID NO:11) and the light chain sequence gL7 (SEQ ID NO:9). Also provided therefore is a neutralising antibody molecule which binds to human IL-17A and to human IL-17F which is cross-blocked from binding human IL-17A and human IL-17F by an antibody comprising the heavy chain sequence gH9 (SEQ ID NO:11) and the light chain sequence gL7 (SEQ ID NO:9). In one embodiment, the neutralising antibodies provided by this aspect of the invention are inhibited from binding to human IL-17A and human IL-17F by an antibody comprising the heavy chain sequence gH9 (SEQ ID NO:11) and the light chain sequence gL7 (SEQ ID NO:9) by greater than 80%, preferably by greater than 85%, more preferably by greater than 90%, even more preferably by greater than 95%.

In another embodiment there is provided a neutralising antibody molecule which binds to human IL-17A and to human IL-17F which is cross-blocked from binding human IL-17A and human IL-17F and IL-17A/F heterodimer by an antibody comprising the heavy chain sequence gH9 (SEQ ID NO:11) and the light chain sequence gL57 (SEQ ID NO:10). In one embodiment, the neutralising antibodies provided by this aspect of the invention are inhibited from binding to human IL-17A and human IL-17F and human IL-17A/F heterodimer by an antibody comprising the heavy chain sequence gH9 (SEQ ID NO:11) and the light chain sequence gL57 (SEQ ID NO:10) by greater than 80%, preferably by greater than 85%, more preferably by greater than 90%, even more preferably by greater than 95%.

In another embodiment there is provided a neutralising antibody molecule which binds to human IL-17A and to human IL-17F which is cross-blocked from binding human IL-17A and human IL-17F and IL-17A/F heterodimer by an antibody comprising the heavy chain sequence gH9 (SEQ ID NO:11) and the light chain sequence gL7 (SEQ ID NO:9). In one embodiment, the neutralising antibodies provided by this aspect of the invention are inhibited from binding to human IL-17A and human IL-17F and human IL-17A/F heterodimer by an antibody comprising the heavy chain sequence gH9 (SEQ ID NO:11) and the light chain sequence gL7 (SEQ ID NO:9) by greater than 80%, preferably by greater than 85%, more preferably by greater than 90%, even more preferably by greater than 95%.

Also provided therefore is a neutralising antibody molecule which binds to human IL-17A and to human IL-17F which is cross-blocked from binding human IL-17A or human IL-17F or human IL-17A/F by an antibody comprising the heavy chain sequence gH9 (SEQ ID NO:11) and the light chain sequence gL57 (SEQ ID NO:10). In one embodiment, the neutralising antibodies provided by this aspect of the invention are inhibited from binding to human IL-17A or human IL-17F or human IL-17A/F by an antibody comprising the heavy chain sequence gH9 (SEQ ID NO:11) and the light chain sequence gL57 (SEQ ID NO:10) by greater than 80%, preferably by greater than 85%, more preferably by greater than 90%, even more preferably by greater than 95%.

Also provided therefore is a neutralising antibody molecule which binds to human IL-17A and to human IL-17F which is cross-blocked from binding human IL-17A or human IL-17F or human IL-17A/F by an antibody comprising the heavy chain sequence gH9 (SEQ ID NO:11) and the light chain sequence gL7 (SEQ ID NO:9). In one embodiment, the neutralising antibodies provided by this aspect of the invention are inhibited from binding to human IL-17A or human IL-17F or human IL-17A/F by an antibody comprising the heavy chain sequence gH9 (SEQ ID NO:11) and the light chain sequence gL7 (SEQ ID NO:9) by greater than 80%, preferably by greater than 85%, more preferably by greater than 90%, even more preferably by greater than 95%.

Epitopes of IL-17A/17-F

Also provided by the invention is a specific region or epitope of human IL-17A and/or a specific region or epitope of human IL-17F and/or a specific region or epitope of human IL-17A/F heterodimer which is bound by an antibody provided by the invention, in particular an antibody comprising the heavy chain sequence gH9 (SEQ ID NO:11) and/or the light chain sequence gL7 (SEQ ID NO:9) and/or the light chain sequence gL57 (SEQ ID NO:10). The sequences for human IL-17A and human IL-17F are provided herein in FIG. 1 (SEQ ID NOS: 27 and 28).

Examples of epitopes of the invention, and methods of determining those epitopes, are provided in Examples 5-7 of U.S. Pat. No. 8,679,494 (Apr. 23, 2008 priority date).

Any suitable method known in the art may be used to determine the residues bound by an antibody provided by the invention e.g. hydrogen-deuterium exchange, site-directed mutagenesis, mass spectrometry, NMR and X-ray crystallography. See for example the methods described in WO2007/149032.

The specific region or epitope of the human IL-17A polypeptide and/or the specific region or epitope of the human IL-17F polypeptide and/or the specific region or epitope of the human IL-17A/F heterodimer can be identified by any suitable epitope mapping method known in the art in combination with any one of the antibodies provided by the invention. Examples of such methods include screening peptides of varying lengths derived from IL-17A and IL-17F for binding to the antibody of the invention with the smallest fragment that can specifically bind to the antibody containing the sequence of the epitope recognised by the antibody. The IL-17 peptides may be produced synthetically or by proteolytic digestion of the appropriate IL-17 polypeptide. Peptides that bind the antibody can be identified by, for example, mass spectrometric analysis. In another example, NMR spectroscopy can be used to identify the epitope bound by an antibody of the invention. In another example, NMR spectroscopy can be used to identify residues which interact with an antibody of the invention. Once identified, the epitopic fragment which binds an antibody of the invention can be used, if required, as an immunogen to obtain additional neutralising antibodies which bind the same epitope.

In one embodiment, the invention provides a neutralising epitope of IL-17A which comprises or consists of one or more of the residues selected from the group consisting of TYR44, ASN45, TRP51, ASN52 and ASP84 of human IL-17A (SEQ ID NO:27).

In one embodiment, the invention provides a neutralising epitope of IL-17A which comprises or consists of one or more of the residues selected from the group consisting of SER41, TYR44, ASN45, TRP51, ASN52, HIS54, ARG72, HIS73 and ASP84 of human IL-17A (SEQ ID NO:27).

In one embodiment, the invention provides a neutralising epitope of IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:27).

In one embodiment, the invention provides a neutralising epitope of IL-17A which comprises one or more of the residues selected from the group consisting of TYR44, ASN45, TRP51, ASN52 and ASP84 of human IL-17A (SEQ ID NO:27) and optionally one or more of the residues selected from the group consisting of SER41, ARG46, HIS54, ARG72, HIS73, HIS86, VAL128, HIS129 and VAL131 of human IL-17A (SEQ ID NO:27).

In one embodiment, the invention provides a neutralising epitope of IL-17A which comprises amino acid residues TYR44, ASN45, TRP51, ASN52 and ASP84 of human IL-17A (SEQ ID NO:27) and optionally one or more of the residues selected from the group consisting of SER41, ARG46, HIS54, ARG72, HIS73, HIS86, VAL128, HIS129 and VAL131 of human IL-17A (SEQ ID NO:27).

IL-17A is a dimer, and in various embodiments, the epitope bound by the antibody comprises one or more residues selected from the group consisting of ARG72, HIS73, ASP80, GLY81, ASN82, ASP84, HIS86, VAL128, HIS129, and VAL131 (of SEQ ID NO: 27) from the first chain of the dimer, and one or more residues selected from the group consisting of SER41, TYR44, ASN45, ARG46, TRP51, ASN52, and HIS54 (e.g., selected from the group consisting of SER41, TYR44, ASN45, and ARG46) (of SEQ ID NO: 27) from the second chain of the dimer.

In various embodiments, the neutralizing antibody specifically binds an epitope of human IL-17A comprising or consisting of one or more of the residues L74, Y85, H73, N82 and R72, preferably L74 and Y85 of SEQ ID NO:27.

In various embodiments, the neutralizing antibody specifically binds an epitope of human IL-17A (e.g., the sequence of which is set forth in GenBank Accession No. Q16552) comprising or consisting of one or more of the residues L74 and G75.

The invention also provides a novel neutralising epitope of human IL-17F (SEQ ID NO:28) which comprises or consists of one or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

The invention also provides a novel neutralising epitope of human IL-17F (SEQ ID NO:28) which comprises or consists of one or more of the following residues: SER39, MET40, SER41, ARG42, ARG47, ASN53, CYS72, ARG73, ASN74, LEU75, LYS83, GLU84, ASP85, ILE86, SER87, MET88, ASN89, SER90, VAL91, PRO92, GLN94, THR119, CYS122, VAL125, THR126, PRO127, VAL128.

In one embodiment, the neutralising epitope of human IL-17F (SEQ ID NO:28) comprises or consists of one or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

In one embodiment, the neutralising epitope of human IL-17F (SEQ ID NO:28) comprises or consists of (or further comprises or further consists of) one or more of the following residues: GLN71, CYS72, ILE86, ASN89, SER90 and VAL128, for example, from a first chain in an IL17F dimer.

In one embodiment, the neutralising epitope of human IL-17F (SEQ ID NO:28) comprises or consists of (or further comprises or further consists of) one or more of the following residues: ARG47, for example, from a second chain in an IL17F dimer.

In one embodiment, the neutralising epitope of human IL-17F (SEQ ID NO:28) comprises or consists of one or more of the following residues: GLN71, CYS72, ASN74, LEU75, ILE86, ASN89, SER90, PRO92, VAL128, HIS131 and GLN133, for example, from a first chain in an IL17F dimer.

In one embodiment, the neutralising epitope of human IL-17F (SEQ ID NO:28) comprises or consists of (or further comprises or further consists of) one or more of the following residues: ARG37, SER39, SER41 and ARG47, for example, from a second chain in an IL17F dimer.

In one embodiment, the neutralising epitope of human IL-17F (SEQ ID NO:28) comprises or consists of one or more of the following residues: GLN71, CYS72, ARG73, ASN74, LEU75, ILE86, SER87 ASN89, SER90, VAL91, PRO92, VAL128, HIS131 and GLN133, for example, from a first chain in an IL17F dimer.

In one embodiment, the neutralising epitope of human IL-17F (SEQ ID NO:28) comprises or consists of (or further comprises or further consists of) one or more of the following residues: ASN33, GLN36, ARG37, SER39, SER41, ARG42, ILE44 and ARG47, for example, from a second chain in an IL17F dimer.

In one embodiment, the neutralising epitope of human IL-17F (SEQ ID NO:28) comprises or consists of one or more of the following residues: GLN12, LYS13, SER24, IS032, ASN33 GLU34, ASN35, GLN36, VAL38, SER46, ASN53, TYR54, GLN69, IS078, ASP85, SER87, MET88, ASN89, GLN94, LYS103 and THR126.

In one embodiment, the neutralising epitope of human IL-17F (SEQ ID NO:28) comprises or consists of one or more of the following residues: GLN12, SER24, ASN33, GLU34, GLN36, VAL38, ASN53, TYR54, ASP85, MET88, ASM89, and THR126.

In one embodiment, the neutralising epitope of human IL-17F (SEQ ID NO:28) comprises or consists of one or more of the following residues: GLN12, SER24, ASN33, GLU34, ASP85 and MET88.

In one embodiment, the neutralising epitope of human IL-17F (SEQ ID NO:28) comprises or consists of amino acids V33 to V38 inclusive.

In one embodiment, the neutralising epitope of human IL-17F (SEQ ID NO:28) comprises or consists of amino acids V87 to Q94 inclusive.

In one embodiment, the neutralising epitope of IL-17F (SEQ ID NO:28) further comprises one or more of the following residues: ILE129, HIS130, H131, V132, Q133.

In one embodiment, there is provided one or more neutralising epitopes of human IL-17F (SEQ ID NO:28) that each independently comprise or consist of amino acids V33 to V38 inclusive and/or V87 to Q94 inclusive.

In various embodiments, the antibody specifically binds an epitope of human IL-17F comprising or consisting of R73, I86, N89, and R47 of SEQ ID NO: 28.

In various embodiments, the neutralizing antibody specifically binds an epitope of human IL-17F (e.g., the sequence of which is set forth in GenBank Accession No. Q96PD4) comprising or consisting of one or more of the residues L75 and G76.

In various embodiments, the antibody specifically binds an epitope of human IL-17F comprising or consisting of S39, S41, N89, C72, N74, L75, S90, V91, P92, V198 of SEQ ID NO: 28.

In various embodiments, the epitope bound by the antibody comprises one or more residues selected from the group consisting of GLN71, CYS72, ARG73, ASN74, LEU75, ILE86, SER87, ASN89, SER90, VAL91, PRO92, VAL128, HIS131, and GLN133 (of SEQ ID NO: 28) from the first chain of the dimer, and one or more residues selected from the group consisting of ASN33, GLN36, ARG37, SER39, SER41, ARG42, ILE44, ARG47 (of SEQ ID NO: 28) from the second chain of the dimer.

In one embodiment, the epitope is defined as amino acid residues located within 4 Angstroms, 3.5 Angstroms, or 3.0 Angstroms of a binding entity, such as an antibody or fragment.

The invention also provides epitopic fragments of IL-17A that can be used, if required, as an immunogen to obtain neutralising antibodies which bind to the neutralising epitope of IL-17A. For example, epitopic fragments comprising one or more of the amino acid residues of IL-17A provided herein above may be used as an immunogen.

The invention also provides epitopic fragments of IL-17F that can be used, if required, as an immunogen to obtain neutralising antibodies which bind to the neutralising epitope of IL-17F. For example, epitopic fragments comprising one or more of the amino acid residues of IL-17F provided herein above may be used as an immunogen.

The invention also provides antibodies which bind to, and/or interact with, a neutralising epitope provided by the invention. It will be appreciated that an antibody can interact directly or indirectly with an epitope of the invention, e.g. by direct binding or by allosteric interaction.

In one embodiment, the invention provides antibodies which bind to, and/or interact with, a neutralising epitope of IL-17A provided by the invention.

Accordingly, in one embodiment, the invention provides a neutralising antibody which binds human IL-17A and human IL-17F that binds to, and/or interacts with, an epitope of human IL-17A comprising or consisting of one or more of the residues selected from the group consisting of TYR44, ASN45, TRP51, ASN52 and ASP84 of human IL-17A (SEQ ID NO:27).

In one embodiment, the invention provides a neutralising antibody which binds human IL-17A and human IL-17F that binds to an epitope of human IL-17A comprising ASN52 of human IL-17A (SEQ ID NO:27).

In one embodiment, the invention provides a neutralising antibody which binds human IL-17A and human IL-17F that binds to an epitope of human IL-17A comprising ASN52 and ASP84 of human IL-17A (SEQ ID NO:27).

In one embodiment, the invention provides a neutralising antibody which binds human IL-17A and human IL-17F that binds to an epitope of human IL-17A comprising ARG46 and HIS54 of human IL-17A (SEQ ID NO:27).

In one embodiment, the invention provides a neutralising antibody which binds human IL-17A and human IL-17F that binds to an epitope of human IL-17A which comprises or consists of one or more of the residues selected from the group consisting of SER41, ASN52, ARG72, HIS73 and ASP84 of human IL-17A (SEQ ID NO:27).

In one embodiment, the invention provides a neutralising antibody which binds human IL-17A and human IL-17F that binds to an epitope of human IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:27).

In one embodiment, the invention provides antibodies which bind to, and/or interact with, a neutralising epitope of IL-17F provided by the invention.

Accordingly, in one embodiment, the invention provides a neutralising antibody which binds human IL-17F that binds to an epitope of human IL-17F comprising one or more of the following residues: SER39, MET40, SER41, ARG42, ARG47, ASN53, ARG73, ASN74, LEU75, LYS83, GLU84, ASP85, ILE86, SER87, MET88, ASN89, SER90, VAL91, PRO92, GLN94, THR126, PRO127, VAL128 of IL-17F (SEQ ID NO:28).

In one embodiment, the invention provides a neutralising antibody which binds human IL-17F that binds to an epitope of human IL-17F within one or more of the following regions: (i) 39-42 (SER39, MET40, SER41, ARG42) (ii) 47 (ARG47) (iii) 53 (ASN53) (iv) 72-75 (CYS72, ARG73, ASN74, LEU75) (v) 83-92 (LYS83, GLU84, ASP85, ILE86, SER87, MET88, ASN89, SER90, VAL91, PRO92) (vi) 94 (GLN94) (vii) 119 (THR119) (viii) 122 (CYS122) (ix) 125-128 (VAL125, THR126, PRO127, VAL128).

In one embodiment, an antibody of the invention binds human IL-17A and human IL-17F. In one embodiment, an antibody of the invention binds human IL-17A/F heterodimer. In one embodiment, an antibody of the invention binds human IL-17A and human IL-17A/F heterodimer. In one embodiment, an antibody of the invention binds human IL-17F and human IL-17A/F heterodimer. In a preferred embodiment, an antibody of the invention binds human IL-17A, human IL-17F and human IL-17A/F heterodimer.

In one embodiment, the invention provides a neutralising antibody which binds human IL-17A and IL-17F that binds to an epitope of human IL-17F within one or more of the following regions: (i) 39-42 (SER39, MET40, SER41, ARG42) (ii) 47 (ARG47) (iii) 53 (ASN53) (iv) 72-75 (CYS72, ARG73, ASN74, LEU75) (v) 83-92 (LYS83, GLU84, ASP85, ILE86, SER87, MET88, ASN89, SER90, VAL91, PRO92) (vi) 94 (GLN94) (vii) 119 (THR119) (viii) 122 (CYS 122) (ix) 125-128 (VAL125, THR126, PRO127, VAL128).

Accordingly, in one embodiment, the invention provides a neutralising antibody which binds human IL-17A and human IL-17F that binds to, and/or interacts with, an epitope of human IL-17F comprising or consisting of one or more of the residues selected from the group consisting of SER39, MET40, SER41, ARG42, ARG47, ASN53, ARG73, ASN74, LEU75, LYS83, GLU84, ASP85, ILE86, SER87, MET88, ASN89, SER90, VAL91, PRO92, GLN94, THR126, PRO127, VAL128 of SEQ ID NO:28 (IL-17F).

In one embodiment, the invention provides a neutralising antibody which binds human IL-17A and human IL-17F that binds, and/or interacts with, an epitope of human IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:27) and binds to, and/or interacts with, an epitope of human IL-17F comprising or consisting of one or more of the residues selected from the group consisting of SER39, MET40, SER41, ARG42, ARG47, ASN53, ARG73, ASN74, LEU75, LYS83, GLU84, ASP85, ILE86, SER87, MET88, ASN89, SER90, VAL91, PRO92, GLN94, THR126, PRO127, VAL128 of SEQ ID NO:28 (IL-17F).

In one embodiment, the invention provides a neutralising antibody which binds human IL-17A and human IL-17F that binds to, and/or interacts with, an epitope of human IL-17F comprising or consisting of one or more of the residues selected from the group consisting of SER39, SER41, ASN74, LEU75, ASN89, SER90, VAL91, PRO92 and VAL128 of SEQ ID NO:28 (IL-17F).

Accordingly, in one embodiment, the invention provides a neutralising antibody which binds human IL-17A and human IL-17F that binds to, and/or interacts with, an epitope of human IL-17F comprising or consisting of one or more of the residues selected from the group consisting of ARG47, ARG73, LEU75 and ILE86 of SEQ ID NO:28 (IL-17F).

Accordingly, in one embodiment, the invention provides a neutralising antibody which binds human IL-17A and human IL-17F that binds to, and/or interacts with, an epitope of human IL-17F comprising LEU75 of SEQ ID NO:28 (IL-17F).

Isolated DNA Sequences of Antibodies

The invention also provides an isolated DNA comprising a nucleic acid sequence encoding the heavy and/or light chain(s) of an antibody molecule of the invention. Preferably, the DNA sequence encodes the heavy or the light chain of an antibody molecule of the invention. The DNA of the invention may comprise synthetic DNA, for instance produced by chemical processing, cDNA, genomic DNA or any combination thereof.

DNA comprising nucleic acid sequences which encode an antibody molecule of the invention can be obtained by methods well known to those skilled in the art. For example, DNA comprising nucleic acid sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in SEQ ID NO:18; SEQ ID NO:19; SEQ ID NO:20; SEQ ID NO:21; SEQ ID NO:22; SEQ ID NO:23; SEQ ID NO:24; SEQ ID NO:25; and SEQ ID NO:26. The invention also relates to a cloning or expression vector comprising one or more DNA sequences of the invention. Accordingly, the invention provides a cloning or expression vector comprising one or more DNA sequences encoding an antibody of the invention. Preferably, the cloning or expression vector comprises two DNA sequences, encoding the light chain and the heavy chain of the antibody molecule of the invention, respectively, along with suitable signal sequences. Preferably, a vector according to the invention comprises the sequences given in SEQ ID NO:21 and SEQ ID NO:24. In one embodiment, a vector according to the invention comprises the sequences given in SEQ ID NO:21 and SEQ ID NO:24.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also the invention provides a host cell comprising one or more cloning or expression vectors comprising one or more DNA sequences encoding an antibody of the invention. Any suitable host cell/vector system may be used for expression of the DNA sequences encoding the antibody molecule of the invention. Bacterial, for example E. coli, and other microbial systems may be used or eukaryotic, for example mammalian, host cell expression systems may also be used. Suitable mammalian host cells include CHO, myeloma or hybridoma cells.

The invention also provides a process for the production of an antibody molecule according to the invention comprising culturing a host cell containing a vector of the invention under conditions suitable for leading to expression of protein from DNA encoding the antibody molecule of the invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Conjugation with Effector Molecules

If desired, an antibody for use in the invention may be conjugated to one or more effector molecule(s). It will be appreciated that the effector molecule may comprise a single effector molecule or two or more such molecules so linked as to form a single moiety that can be attached to the antibodies of the invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof, e.g., DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g., angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins, or albumin binding compounds, such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g., a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example, antibodies for use in the invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971). In one example, the antibody molecule of the invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g., maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment which is PEGylated, i.e., has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example, PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly (ethyleneglycol) polymer having a molecular weight of approximately 20,000 Da. The total molecular weight of the PEG attached to the Fab fragment may therefore be approximately 40,000 Da.

In one embodiment, a neutralising antibody molecule of the invention is a modified Fab fragment having at the C-terminal end of its heavy chain a modified hinge region containing at least one cysteine residue to which an effector molecule is attached. In one embodiment, the invention provides a neutralising antibody molecule having specificity for human IL-17A and human IL-17F, which is a modified Fab fragment having a heavy chain comprising the sequence given in SEQ ID NO:11 and a light chain comprising the sequence given in SEQ ID NO:9 or the sequence given in SEQ ID NO:10 and having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

Pharmaceutical Compositions, Administration Regimens

As the antibodies of the invention are useful in the treatment and/or prophylaxis of a pathological condition, the invention also provides a pharmaceutical or diagnostic composition comprising an antibody molecule of the invention in combination with one or more of a pharmaceutically acceptable excipient, diluent or carrier. Accordingly, provided is the use of an antibody according to the invention for the manufacture of a medicament. The composition will usually be supplied as part of a sterile, pharmaceutical composition that will normally include a pharmaceutically acceptable carrier. A pharmaceutical composition of the invention may additionally comprise a pharmaceutically-acceptable adjuvant.

The invention also provides a process for preparation of a pharmaceutical or diagnostic composition comprising adding and mixing the antibody molecule of the invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example, anti-TNF, anti-IL-1β, anti-T cell, anti-IFNγ or anti-LPS antibodies, or non-antibody ingredients such as xanthines or a small molecule inhibitor.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, preferably 0.1 mg/kg to 20 mg/kg (e.g., 5 mg/kg to 10 mg/kg, such as about 8 mg/kg). Pharmaceutical compositions may be conveniently presented in unit dose forms containing a predetermined amount of an active agent of the invention per dose. Unit doses may range from 10 mg to 1,000 mg (e.g., between 80 mg and 720 mg, between 100 mg and 680 mg or between 160 mg and 640 mg), preferably 8 mg, 16 mg, 32 mg, 40 mg, 80 mg, 160 mg, 240 mg, 320 mg, 480 mg, 560 mg, and 640 mg.

In various embodiments of methods of treating psoriasis, such as plaque psoriasis, the amount of neutralizing antibody administered to the subject is an amount that achieves at least a 50% change, at least a 60% change, at least a 75% change (e.g., at least an 80% change, at least an 85% change, at least a 90% change, or at least a 95% change) in lesion severity score (LSS) compared to pre-treatment (i.e., LSS prior to administration of the neutralizing antibody) at two, four, six, or eight weeks following administration of the antibody. Alternatively or in addition, the amount of neutralizing antibody administered is an amount that achieves at least a 50% change, at least a 60% change, at least a 75% change (e.g., at least an 80% change, at least an 85% change, at least a 90% change, or at least a 95% change) in Psoriasis Area and Severity Index (PASI) compared to pre-treatment at two, four, six, or eight weeks following administration of the antibody. Alternatively or in addition the amount of neutralising antibody is an amount that achieves at least a 50% change, a 60% change, a 75% change (e.g., an 80% change, an 85% change, a 90% change, or a 95% change) in PASI compared to pre-treatment at two, four, six or eight weeks following administration of the antibody and which maintains or increases the change in PASI response for an additional two, four, six, eight, ten, twelve, fourteen, sixteen, eighteen, twenty or more weeks following administration of the antibody. Optionally, the amount of neutralizing antibody is an amount that achieves at least a 50% change, a 60% change, a 75% change (e.g., an 80% change, an 85% change, a 90% change, or a 95% change) in PASI compared to pre-treatment at two, four, six or eight weeks following administration of the antibody, and the PASI score does not change more than 5%, more than 10%, more than 20%, more than 25%, more than 30%, more than 35%, or more than 40% toward baseline (pre-treatment level) for an additional two, four, six, eight, ten, twelve, fourteen, sixteen, eighteen, twenty or more weeks following administration of the antibody.

An alternative means of evaluating treatment of psoriasis is the Physician's Global Assessment score. The PGA scoring system is based on lesion erythema, induration, and scale, with score assignments that range from clear to severe, typically using a 5 or 6-level scale See, e.g., Langley et al., J Am Acad Dermatol. 2004; 51(4):563-569. In various aspects, the method of treating psoriasis described herein results in a reduction of PGA score of at least 20%, at least 50%, or at least 70% from baseline at week 2, week 6, week 8, and/or week 12 following administration.

In various embodiments concerning treatment of psoriatic arthritis, the amount of neutralizing antibody administered to the subject is an amount that achieves (i) at least a 50% change, at least a 60% change, at least a 75% change (e.g., at least an 80% change, at least an 85% change, at least a 90% change, or at least a 95% change) in lesion severity score (LSS) compared to pre-treatment (i.e., LSS prior to administration of the neutralizing antibody) at two, four, six, or eight weeks following administration of the antibody and/or (ii) at least a 50% change, at least a 60% change, at least a 75% change (e.g., at least an 80% change, at least an 85% change, at least a 90% change, or at least a 95% change) in Psoriasis Area and Severity Index (PASI) compared to pre-treatment at two, four, six, or eight weeks following administration of the antibody and/or (iii) at least a 20% change, at least a 30%, at least a 50%, at least 60% or at least a 70% change in American College of Rheumatology ("ACR") response compared to pre-treatment at two, four, six, or eight weeks following administration of the antibody. Alternatively or in addition, the amount of neutralising antibody is an amount that achieves the aforementioned changes in LSS, PASI, and/or ACR scores at two, four, six or eight weeks following administration of the antibody and maintains or increases the change in LSS, PASI, and/or ACR response for an additional two, four, six, eight, ten, twelve, fourteen, sixteen, eighteen, twenty or more weeks following administration of the antibody. Optionally, the amount of neutralizing antibody is an amount that achieves the aforementioned change in LSS, PASI, and/or ACR score at two, four, six or eight weeks following administration of the antibody, and the LSS, PASI, and/or ACR score does not change more than 5%, more than 10%, more than 20%, more than 25%%, more than 30%, more than 35%, or more than 40% toward baseline (pre-treatment level) for an additional two, four, six, eight, ten, twelve, fourteen, sixteen, eighteen, twenty or more weeks following administration of the antibody.

CA028_0496.g3 has been tested in patients following single intravenous dose administration over the dose range of 8 mg to 640 mg. CA028_0496.g3 has also been tested as a repeat dose administration with different dosing regimens involving a loading dose followed by maintenance doses at weeks 3 and 6. A multiple dose regimen without a loading dose also is contemplated as part of the invention.

It will be appreciated that a suitable dosage regimen for any given anti-IL-17A/F antibody may be designed using PK and PD (efficacy) information determined for the antibody, as described in the Examples herein for CA028_0496.g3 (bimekizumab). Typically a dosing regimen for use in the present invention will provide a mean trough level of between around 1 and 50 micro g/ml following single or multiple dose (steady state), for example a mean trough level of greater than 10 micro g/ml.

Potential dose ranges and regimens for any of the embodiments described herein include, but are not limited to, dosages ranging from 10 mg-1000 mg unit doses (e.g., 8 mg, 16 mg, 32 mg, 40 mg, 64 mg, 80 mg, 160 mg, 240 mg, 320 mg, 480 mg, 560 mg, or 640 mg), given every 1-10 weeks (by any route of administration, such as by as either a subcutaneous or intravenous administration). Optionally, a dose of neutralizing antibody is administered every 1-20 weeks, for example every 2 weeks, every 3 weeks, every 4 weeks, every 5 weeks, every 6 weeks, every 7 weeks, or every 8-12 weeks (e.g., every 8 weeks, every 9 weeks, every 10 weeks, every 11 weeks, or every 12 weeks). The treatment period (i.e., the period of time during which one or more doses of antibody are administered to a subject) may comprise at least two weeks, at least four weeks, at least eight weeks, at least 12 weeks, at least 16 weeks, at least 20 weeks, at least 24 weeks, at least 30 weeks, at least 36 weeks, at least 40 weeks, at least 44 weeks, at least 48 weeks, at least 52 weeks, or more. Any suitable number of doses may be administered within the treatment period, such as the doses and time between administrations described above. For example, one, two, three, or four doses of antibody are administered to a subject over, e.g., a 12 week treatment period (optionally at week 0, week 4, week 8, and week 12). In one exemplary embodiment, the method comprises administering 320 mg of antibody to a subject every four weeks for at least twelve weeks. In one exemplary embodiment, the method comprises administering 160 mg of antibody to a subject every four weeks for at least twelve weeks. In one example the method comprises administering 160 mg, 240 mg or 320 mg every four weeks. In one example the method comprises a 320 mg loading dose followed by a maintenance dose of 160 mg or 240 mg every four weeks. It will be appreciated that the doses may be given at these intervals for a first treatment period, then given at a different interval for a second treatment period (e.g., administered every four or eight weeks for a first treatment period of, for example, 12 or 16 or 20 weeks, then administered every eight, 12, or 16 weeks for a second treatment period lasting an additional, e.g., 24 or 36 weeks or more).

In some examples of the invention the dosage regimen used in an initial treatment period, such as the first 12 or 16 or 24 weeks of treatment, may be considered an 'induction period', after which a different regimen, such as a maintenance regimen, may be used in which typically a lower dosage or reduced frequency of dosing may be used.

In some instances it may be possible to reduce the dosing frequency and/or dose once a certain level of efficacy has been achieved. For example, in the method of treating psoriasis of the present invention, at week 12 or week 16 or week 24 the dosing frequency and/or dose may be changed if the subject has achieved a PASI 75 or PASI 90. For example, in the method of treating psoriatic arthritis of the present invention, at week 12 or week 16 or week 24 the dosing frequency and/or dose may be changed if the patient has achieved an ACR50. For example, in the method of treating ankylosing spondylitis or nr-axSpa of the present invention, at week 12 or week 16 or week 24 the dosing frequency and/or dose may be changed if the patient has achieved an ASAS40. Similarly in each of these examples, if at week 12 or week 16 or week 20 or week 24, the subject has not achieved a desired clinical score, the dose and/or dosing frequency may be increased.

In various embodiments, including embodiments comprising treating psoriasis in a subject, an initial dose of antibody is administered then a subsequent dose of neutralizing antibody (such as CA028_0496.g3) is administered 8-20 weeks (e.g., 8 weeks, 12 weeks, 16 weeks, or 20 weeks) after an initial administration. The subsequent dose may be the same as the initial dose, an increased amount of neutralizing antibody, or a decreased amount of neutralizing antibody (i.e., a maintenance dose). Dosing with a neutralizing antibody described herein (e.g., CA028_0496.g3 (Bimekizumab)) demonstrated rapid onset and remarkable, prolonged beneficial effect in humans, such as humans suffering from psoriasis and psoriatic arthritis. For example, a single administration of doses of 160 mg or more (e.g., 160 mg, 480 mg, and 640 mg) achieved clinically relevant and statistically significant differences from placebo in lesion severity score (LSS) and psoriasis area and severity index (PASI) from week 2, with near-maximal improvements achieved by about four to six weeks post-administration, which were maintained until around 16-20 weeks post-administration. In the 480 mg and 640 mg dose groups, on average 83% of patients experienced PASI 90 from weeks 6-12 and 90% at week 12. In subjects suffering from psoriatic arthritis, clinically relevant responses in disease activity measures were observed at 20 weeks following initial administration of neutralizing antibody (followed by two maintenance doses as described in Example 1).

An exemplary method of treating psoriatic arthritis provided by the disclosure comprises administering to a subject an antibody described herein using any one of the following dosage regimens: 16 mg every four weeks, 160 mg every four weeks, 320 mg loading dose at week 0 followed by a maintenance dose of 160 mg every four weeks, and 320 mg every four weeks. In one example, the method of treating psoriatic arthritis provided by the disclosure comprises administering to a subject an antibody described herein using any one of the following dosage regimens: 160 mg every four weeks, 320 mg every four weeks, 320 mg loading dose at week 0 followed by a maintenance dose of 160 mg every four weeks or 320 mg loading dose at week 0 followed by a maintenance dose of 240 mg every four weeks. The treatment period can comprise, e.g., 12 weeks (for a total of at least three or four administrations of antibody), 16 weeks, 24 weeks, or 48 weeks, or more. It will be appreciated that the doses may be given at these intervals for a first treatment period, then given at a different interval for a second treatment period (e.g., administered every four or eight weeks for a first treatment period of, for example, 12 or 16 or 20 weeks, then administered every eight, 12, or 16 weeks for a second treatment period lasting an additional, e.g., 24 or 36 weeks or more). For example, the dosage regimen, such as the dosing frequency, may change after a period of time, such that in one example the antibody is administered using a dosage regimen of 160 mg every four weeks until week 12, week 16 or week 24 followed by 160 mg every eight weeks, starting at week 20, week 24 or week 32 respectively. In one example the antibody is administered using a dosage regimen of 320 mg every four weeks until week 12, week 16 or week 24 followed by 320 mg every eight weeks starting at week 20, week 24 or week 32 respectively. Optionally the dosage regimen, such as dosage amount, may change after a period of time, such that in one example the antibody is administered using a dosage regimen of 160 mg or 320 mg every four weeks until week 12 or week 16 or week 24 followed by a dosage regimen of 320 mg or 160 mg every four weeks respectively. Optionally both the dosage amount and dosage frequency may change, such that in one example the antibody is administered using a dosage regimen of 160 mg every four weeks until week 12 or week 16 or week 24 followed by a dosage regimen of 320 mg every eight weeks.

In the case of psoriatic arthritis, it will be appreciated that the dosage regimen may differ depending on whether the subject has coexistent psoriasis and/or a history of psoriasis or not. For example, the dosage regimen for psoriatic arthritis patients with coexistent moderate to severe plaque psoriasis or a history of psoriasis may comprise higher dosages and/or more frequent dosing than the dosage regimen for those subjects who do not have coexistent psoriasis and/or a history of psoriasis.

An exemplary method of treating psoriasis provided by the disclosure comprises administering to a subject an antibody described herein using any one of the following dosage regimens: 64 mg every four weeks, 160 mg every four weeks or every 8 weeks, 320 mg every four weeks or every eight weeks, 320 mg loading dose administered at week 0 followed by maintenance doses of 160 mg every four weeks, or 480 mg every four weeks. The doses may be given at these intervals over any suitable treatment period such as at least four weeks, at least eight weeks, at least 12 weeks, at least 16 weeks, at least 20 weeks, at least 24 weeks, at least 28 weeks, at least 30 weeks, at least 36 weeks, at least 40 weeks, at least 44 weeks, at least 48 weeks, at least 52 weeks, or more. It will be appreciated that the doses may be given at these intervals for a first treatment period, then given at a different interval for a second treatment period (e.g., administered every four or eight weeks for a first treatment period of, for example, 12 or 16 or 20 or 24 weeks, then administered every eight, 12, or 16 weeks for a second treatment period lasting an additional, e.g., 24 or 36 weeks). For example, the dosage regimen, such as the dosing frequency, may change after a period of time, such that in one example the antibody is administered using a dosage regimen of 160 mg every four weeks until week 8, 12 or 16 followed by 160 mg every eight weeks, starting at week 16, 20 or 24 respectively. In one example the antibody is administered using a dosage regimen of 320 mg every four weeks until week 8, 12 or 16 followed by 320 mg every eight weeks starting at week 16, 20 or 24 respectively. In one example the antibody is administered using a dosage regimen of 320 mg or 160 mg every four weeks until week 8, 12 or 16 followed by 320 mg or 160 mg every twelve weeks. Optionally the dosage regimen, such as dosage amount, may change after a period of time, such that in one example the antibody is administered using a dosage regimen of 320 mg every four weeks until week 8 or week 12 followed by a reduction to 160 mg every four weeks starting at week 12 or week 16 respectively.

An exemplary method of treating ankylosing spondylitis or nr-axSpa provided by the disclosure comprises administering to a subject an antibody described herein using any one of the following dosage regimens: 16 mg every four weeks, 160 mg every four weeks, 320 mg loading dose at week 0 followed by a maintenance dose of 160 mg every four weeks or 320 mg every four weeks. Preferably the dosage regimen is 160 mg or 320 mg every four weeks. The treatment period can comprise, e.g., 12 weeks (for a total of at least three or four administrations of antibody), 16 weeks, 24 weeks, or 48 weeks, or more. It will be appreciated that the doses may be given at these intervals for a first treatment period, then given at a different interval for a second treatment period (e.g., administered every four or eight weeks for a first treatment period of, for example, 12 or 16, 20 or 24 weeks, then administered every eight, 12, or 16 weeks for a second treatment period lasting an additional, e.g., 24 or 36 weeks or more). For example, the dosage regimen, such as frequency, may change after a period of time, such that in one example the antibody is administered using a dosage regimen of 160 mg every four weeks until week 12, 16 or 24 followed by 160 mg every eight weeks. In one example the antibody is administered using a dosage regimen of 320 mg every four weeks until week 12, 16 or 24 followed by 320 mg every eight weeks. Optionally the dosage regimen, such as dosage amount, may change after a period of time, such that in one example the antibody is administered using a dosage regimen of 160 mg or 320 mg every four weeks until week 12 or week 16 or week 24 followed by a dosage regimen of 320 mg or 160 mg every four weeks respectively. Optionally both the dosage amount and dosage frequency may change, such that in one example the antibody is administered using a dosage regimen of 160 mg every four weeks until week 12 or week 16 or week 24 followed by a dosage regimen of 320 mg every eight weeks.

Compositions may be administered individually to a patient or may be administered in combination (e.g., simultaneously, sequentially or separately) with other agents, drugs or hormones.

The dose at which the antibody molecule of the invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g., 2 to 10 hours) it may be necessary to give one or more doses per day. Alternatively, if the antibody molecule has a long half-life (e.g., 2 to 15 days) it may only be necessary to give a dosage once per day, once per week or even once every 1 or 2 months.

It may be necessary to administer a loading dose followed by one or more maintenance doses. The loading dose and maintenance doses may be the same dosage amount, or they may be different. In one embodiment, the maintenance doses may be one-quarter, one-third, one-half, two-thirds, three-quarters, the same as, one and one-quarter, one and one-third, one and one-half, one and two-thirds, one and three-quarters, double, or more of the loading dose.

In one embodiment, the maintenance doses may be administered at an interval after administration of the loading dose. This interval may be consistent for each dose or may vary. This interval may be 1 day, 1 week, 2 weeks, 3 weeks, 4 weeks, monthly, 6 weeks, 8 weeks, every other month, or at any other interval. In one embodiment, two maintenance doses are administered every three weeks after a loading dose for a total of three doses. In one embodiment, maintenance doses are administered every four weeks.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. A preferred embodiment of the invention involves subcutaneous or intravenous administration of the antibody.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the invention will be administered by use of gene therapy. In order to achieve this, DNA comprising nucleic acid sequences encoding the heavy and light chains of the antibody molecule under the control of appropriate DNA components are introduced into a patient such that the antibody chains are expressed from the DNA sequences and assembled in situ.

In one embodiment, the formulation is provided as a formulation for topical administrations including inhalation. Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient. These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns, for example, from 0.1 to 5 microns, in particular from 1 to 5 microns. The particle size of the active ingredient (such as the antibody or fragment) is of primary importance.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellant gases may be used on their own or in mixtures thereof. Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable. The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

EXAMPLES

Example 1—Clinical Trial of CA028_0496.g3 (UCB4940 or Bimekizumab); Loading Dose and Maintenance Doses In one embodiment, an early proof-of-concept, investigator blind, placebo-controlled study evaluating the safety, pharmacokinetics and pharmacodynamics of multiple doses of CA028_0496.g3 in subjects with psoriatic arthritis has been performed. This is identified as UCB study PA0007.

The study comprised four active dose arms and placebo administered intravenously as an infusion on three occasions given every three weeks: Cohort 1 (240 mg loading dose at week 0 followed by 160 mg at week 3 and week 6 [N=20 (active), 3 placebo]; Cohort 2 (80 mg loading dose at week 0 followed by 40 mg at week 3 and week 6)[ N=6 (active), 3 placebo]; Cohort 3 (160 mg loading dose at week 0, followed by 80 mg at week 3 and week 6), N=6 (active), 3 placebo; Cohort 4 (560 mg loading dose at week 0, followed by 320 mg at week 3 and week 6), N=6 (active), 3 placebo.

The objectives of this study included the safety, tolerability and pharmacokinetics of multiple-dose administration of CA028_0496.g3 in subjects with psoriatic arthritis. The objectives also included the evaluation of the effect of multiple-dose administration of CA028_0496.g3 on the severity of psoriatic arthritis in the joints (American College of Rheumatology ("ACR") 20/50/70 response) and, for skin, the clinical features of plaque psoriasis (Psoriasis Area and Severity Index ("PASI") 50/75/90 response). ACR score is a scale that measures improvement in joint effects associated with psoriatic arthritis and rheumatoid arthritis, and improvements in ACR score are also associated with the treatment of rheumatoid arthritis.

Patient Population: All eligible subjects were required to be at least 18 years of age and have a diagnosis of adult-onset psoriatic arthritis made at least 6 months prior to screening for the study as defined by the classification criteria for psoriatic arthritis ("CASPAR") criteria (i.e., inflammatory articular disease (joint, spine or entheseal) and ≥3 points of the 5 CASPAR categories). The CASPAR criteria used may be found in FIG. 2. Subjects were also required to have active psoriatic lesions or a history of psoriatic lesions. In terms of joint involvement, subjects were required to have active arthritis as defined by: ≥3 tender joints at screening and baseline, ≥3 swollen joints at screening and baseline, and fulfilling at least one of the following during screening (either ESR≥28 mm/hour or CRP≥3 mg/L). Subjects were all inadequate responders to at least one non-biologic disease-modifying antirheumatic drug ("DMARD") and/or 1 approved biologic DMARD. Subjects must have been taking concurrent methotrexate at the start of treatment for at least 3 months, and be on a stable dose at least 4 weeks prior to baseline. Subjects who were intolerant to methotrexate may have been eligible if they had received non-steroidal anti-inflammatory drugs (NSAIDs) and/or steroids for at least 8 weeks and were on a stable dose at least 4 weeks prior to baseline.

Study Disposition: 50 subjects completed all doses of the study, of which 38 subjects received at least one dose of the investigational medicinal product, CA028_0496.g3. Including subjects who received placebo, a total of 48 subjects formed the overall analysis data set as two subjects were excluded for being potentially un-blinded at the site.

Clinical Outcomes: Clinically significant effects were observed for both joints and skin at week 8 from start of treatment:

Skin Effects: 23 subjects had skin involvement at baseline, with body surface area (BSA)≥3% and a mean baseline PASI of 15.9 (SD=14.6). Only 22 subjects were in the analysis data set due to missed dosing by one subject. Results on skin effects are described in FIG. 3a and FIG. 3b. Onset of response was rapid for both skin and joints. Out of the eligible subjects for skin assessment, for the combined top 3 doses, a PASI75 response of 100% was observed at week 8 from start of treatment, and a PASI90 response of 87% and appear to have been maintained until the end of the study at week 20 post-start of treatment. In contrast, in the Future 1 trial for Secukinumab in psoriatic arthritis, the observed PASI75 response at week 24 was 64.8% and PASI 90 response at week 24 was 49%. (Glottieb A B et al. Arthritis Rheum. 2014, 66(Suppl 11):5233; Mease P et al. Ann Rheum Dis. 2014; 73(1):48-55.) This is further depicted in FIG. 4.

Joint Effects: Results on joint effects are described in FIGS. 5a-5d. An 80% ACR20 response, a 40% ACR50 response and a 23% ACR70 response were observed at week 8 from start of treatment was observed for the combined top 3 doses of the group. The ACR20 response appeared to be sustained at this level through to week 20 (day 140), albeit with an increased placebo response (see FIG. 5b-5d). Following week 8 (2 weeks after the last dose) background medication was un-controlled.

The time to maximum ACR50 and 70 responses took longer (post week 12), with responses of 56.7% and 36.7% by week 20, respectively. In contrast, in the Future 1 trial for Secukinumab in psoriatic arthritis, the observed ACR20 response at week 24 was 50%. Mease P et al., 2014, Arthritis Rheum., 66(Suppl 11):S423-S424; Mease P et al., 2014, Ann Rheum Dis., 73(1):48-55. This is further depicted in FIG. 6.

Bayesian Analysis: A Bayesian analysis of ACRn(tr) at week 8 from start of treatment was performed using a Gaussian-likelihood model with an informative prior on the placebo group. An assessment of the equality of the treatment effect size as well as homogeneity of variances was performed and it was deemed to be appropriate to pool the top three doses together for CA028_0496.g3. The informed prior on the placebo group for ACRn(tr) was estimated by using data from a previous Cimzia® study in psoriatic arthritis (PsA001, A phase 3, multicenter, randomized, double-blind, parallel-group, placebo-controlled study to evaluate the efficacy and safety of certolizumab pegol in subjects with adult-onset active and progressive psoriatic arthritis.).

The Bayesian analysis indicated strong statistical evidence (probability>99%) that CA028_0496.g3 achieves higher values of ACRn(tr) compared to placebo. Furthermore, the probability that the median treatment difference in ACRn(tr) compared to placebo is greater than 0.31 (difference observed in previous Cimzia® studies) was more than 99% in the pooled CA028_0496.g3 top 3 doses group.

For ACR20 response, a Bayesian analysis was performed at Week 8 post start of dosing using a logistic model with an informative prior on the placebo group. The informed prior for the placebo group on ACR20 was estimated using data from a previous Cimzia® study (PsA001).

The Bayesian analysis indicated that the probability of CA028_0496.g3 inducing greater ACR20 response rates than placebo was over 99% for the pooled CA028_0496.g3 top 3 doses groups. In addition, there was a >99% probability that the median treatment difference in ACR20 compared to placebo is greater than 25% (difference observed in PsA001) for the pooled top 3 doses of CA028_0496.g3. These results are presented in FIG. 7.

The validity of these results in terms of benchmarking against other biological therapies (anti-TNFs and IL17As and anti-IL12/23) in psoriatic arthritis was made by comparing with literature data for ACR20 response at week 8. (Adalimumab, Golimumab, Secukinumab and Ustekinumab, see FIG. 8), ensuring overall concordance in the results. In conclusion, a high posterior probability (>99%) for observed effects on ACR20 response is greater than anti-TNFs or anti-IL-17As at week 8 in this PA0007.

Pharmacokinetic-Pharmacodynamic Targeting: In order to achieve the pharmacologically active dose levels to achieve the desired clinical effects, four active dosing arms were selected. The aim was to achieve trough concentrations over the first 8 week period of 10× the Ec50 (derived from mild psoriasis response in UP0008 described in Example 2) of approximately 10 µg/mL and higher. The results of this study are included in FIG. 9. In UP0008, bimekizumab demonstrated dose-proportional PK (half-life of about 22 days).

Predicted Sub-Cutaneous Dosing: A bioavailability study (RA0124) was conducted for CA028_0496.g3 to evaluate the pharmacokinetics of CA028_0496.g3 following subcutaneous administrations of 80 mg and 160 mg doses compared to 160 mg given by i.v. The results indicate that based on the principles of super-position, it should be possible to achieve the target concentrations of CA028_0496.g3 summarized in FIG. 9 (achieved in PA0007) via monthly subcutaneous doses of 160 mg or greater, such as 320 mg, using a Q4W regimen (FIG. 10) or via a 320 mg loading dose followed by a 160 mg Q4W regimen.

Example 2—Clinical Trial of CA028_0496.g3 (UCB4940 or Bimekizumab); Single Dose

UP0008 is a single ascending dose Phase 1 study (NCT02529956) of the safety of intravenously administered CA028_0496.g3 in subjects with mild to moderate psoriasis affecting ≤5% body surface area (BSA). Inclusion criteria included, e.g., male or female (≥18 to ≤70 years), confirmed diagnosis of mild-to-moderate plaque-type psoriasis for ≥6 months involving ≤5% of body surface area (excluding the scalp), and ≥2 psoriatic lesions with ≥1 plaques in suitable biopsy sites. Exclusion criteria included, e.g., use of systemic non-biologic psoriasis therapy (methotrexate, cyclophosphamide) or psoralen plus ultraviolet A/ultraviolet A phototherapy within 4 weeks prior to screening, treatment with biologic agents ≤12 months before the study, and use or planned use of live attenuated vaccines ≤6 weeks of screening. A total of 39 patients received a single i.v. dose of bimekizumab (8-640 mg) or placebo (randomized, double-blind). Five dosages were employed: 8 mg, 40 mg, 160, mg, 480 mg, and 640 mg. Following single-dose administration, bimekizumab (8-640 mg) was well tolerated and no patient discontinued due to treatment-emergent AEs; no severe AEs were reported. Indeed, doses of up to 640 mg (approximately 8 mg/kg body weight) have been well tolerated to date in UP0008.

After administration, bimekizumab produced improvements across the evaluated clinical features of plaque psoriasis, LSS, PASI and PGA (FIG. 14). A fast onset of response was observed with a reduction of >80% from baseline LSS in the top two dose cohorts at study Week 2. For doses 160, 480, and 640 mg (N=6 each), clinically-relevant and statistically significant differences from placebo (N=13) were observed in lesion severity score (LSS) (FIG. 11) and psoriasis area and severity index (PASI) from week 2 (FIG. 12), with near-maximal improvements observed by week 4.

Specifically with respect to LSS, the magnitude of response was reflected by a maximal reduction in mean change from baseline in LSS of >90% in the 160 mg group. This was achieved by Week 8 and demonstrated durability, being maintained to Week 16. In the 480 mg cohort a maximal magnitude of response, 100%, was achieved as early as Week 4. The response also was durable, being maintained to Week 16. In the 640 mg cohort, the maximal reduction (100%) was achieved by Week 8 and was durable, being maintained between Weeks 12 and 20 (FIG. 14A). In addition to the 640 mg cohort, no overlap in CIs between the other bimekizumab cohorts (40-480 mg) at Week 2 vs placebo was observed, indicating a difference between the two cohorts. Similar results were obtained for the area under the effect curve (Weeks 0-4, [AUEC0-4w]) variable (data not shown).

With respect to PASI, a fast onset of response was observed with a reduction of >65% from baseline PASI scores in the top two cohorts at Week 2. Bayesian analysis revealed that the posterior probability of ≥60% improvement over placebo at this time point was >80%. For the bimekizumab 160 mg cohort, the magnitude of response was reflected by a maximal reduction in the mean change from baseline in PASI score of >85% achieved by Week 6. This response was durable, being maintained to study Week 12. In the 480 mg and 640 mg cohorts, a maximal magnitude of response of ≥94% was observed. This was achieved by Week 6 in the 480 mg cohort and Week 4 in the 640 mg cohort. In both cohorts the response was durable, being maintained to Week 12 (FIG. 5b). Additionally, for bimekizumab 40-640 mg cohorts at Week 2, the posterior probability of a >0% improvement in PASI score over placebo was 99%.

The significant level of improvement (as indicated by LSS percent change and PASI percent change from baseline) was maintained until the final timepoint measured—20 weeks. In the top two dose groups, 83% of patients experienced PASI 90 (a 90% improvement in PASI score), from weeks 6-12 and 90% at week 12 (FIG. 13). At the top three doses, 100% of patients achieved PASI75, and 53% achieved PASI100.

PGA (Physicians Global Assessment) also was assessed using a seven-point scale (0=clear, 6=severe). See FIG. 14. A reduction of >50% from baseline in PGA was observed at the highest doses of bimekizumab (480 mg and 640 mg) assessed. Maximal reductions in mean change from baseline in PGA scores of >75% were observed in the bimekizumab 160 mg cohort. This reduction was achieved by Week 6 and was durable, being maintained to Week 12. Maximal reductions in mean change from baseline in PGA scores were 100% and 94%, respectively for bimekizumab 480 mg and 640 mg cohorts (FIG. 5c). These reductions were achieved by Week 8 and were durable, being maintained to Week 12 in the 480 mg cohort, and achieved by Week 4 and maintained to Week 12 in the 640 mg cohort.

Example 3—Anti-IL17A/F Antibody Down Regulates Bone Formation Processes

Prototypical phenotypic subsets of spondyloarthrititis are ankylosing spondylitis (AS) for axial disease and psoriatic arthritis (PsA) for the combination of peripheral arthritis with psoriasis. Individual patients often display multi-system disease; a significant proportion of patients with AS exhibit skin psoriasis and a significant proportion of patients with PsA develop axial disease. AS and PsA share a common genetic background, familial aggregation of the different subforms, shared histopathological findings, and similar responses to therapy (e.g., efficacy of TNF blockade and IL-17A blockade in both AS and PsA and failure of B cell depleting therapy and IL-6 blockade in AS as well as PsA). The results described herein with respect to psoriatic arthritis suggest therefore that anti-IL-17A/F antibodies may also be effective in the treatment of ankylosing spondylitis.

Pathological bone formation associated with the spondyloarthropathies (SpA) is a major cause of structural tissue damage resulting in permanent patient disability. Patients with AS experience excessive bone formation on the periosteal surface near joints and intervertebral spaces, resulting in bone spurs that fuse joints and aggravate tendon and ligament insertion sites, causing pain and limited mobility associated with the disease. Previous studies using recombinant IL-17A and IL-17F revealed divergent effects in osteogenic differentiation. Osta et al., Frontiers in Immunology 5, (2014), have demonstrated that IL-17 positively influences osteogenic differentiation in human mesenchymal stem cells (hMSCs). In agreement, Huang et al, Cell Death Differ. 16, 1332-43 (2009) have reported that IL-17 stimulates proliferation and osteogenic differentiation of hMSCs. In addition, Croes et al. *Bone* 84, 262-270 (2016), demonstrated osteogenic stimulation of hMSCs with IL-17A and IL-17F over a range of concentrations. Conversely, others demonstrated that IL-17 inhibited the osteogenic differentiation of rat calvarial cells, mouse MSCs and adult human MSCs, and implicated that IL-17 was pro-osteogenic. See, e.g., Chang et al., Proc. Natl. Acad. Sci. U.S.A. 110, 9469-74 (2013); Nam et al., PLoS One 7, e40044 (2012).

This Example demonstrates that an anti-IL-17A/F monoclonal antibody (CA028_0496.g3 (Bimekizumab)) reduced biomarkers associated with periosteal stem cell osteogenic differentiation in vitro, reduced matrix mineralization, and reduced bone nodule formation in vitro, demonstrating that an anti-IL-17A/F monoclonal antibody (CA028_0496.g3 (Bimekizumab)) is likely to be effective in treating (e.g., slowing the progression of, reducing the symptoms of) AS.

Methodology: As the periosteum gives rise to reparative tissues for fracture repair, a human periosteal stem cell model (Eyckmans et al., Biomaterials 34, 4612-21 (2013)) was employed to probe the IL-17 axis in the context of pathological bone formation. Periosteum was harvested from patients undergoing lower limb orthopedic surgery, as previously described. Roberts et al., Biomaterials 32, 4393-4405 (2011); Roberts et al., Stem Cell Res. 7, 137-144 (2011). Adherent human periosteum derived stem cells (hPDSCs) were enzymatically released from the matrix and expanded in growth media (DMEM medium supplemented with 10% fetal bovine serum, 1% sodium pyruvate, 1% antibiotics and antimycotics). For in vitro osteogenic differentiation assays, passage 6 hPDSCs were seeded at 3000 cells/cm$^2$ in 24-well plates to allow quantification of gene expression and mineralization in response to TH-17 supernatant exposure. These cultures were incubated with TH-17 supernatant (1:50 dilution) containing vehicle (PBS) or anti-IL-17A, anti-IL-17F, or anti-IL-17A/F antibody (10 μg/ml) in combination with an osteogenic growth factor cocktail (GFC); 10 ng/ml TGF-β1 (Peprotech), 20 ng/ml EGF (Invitrogen), 10 ng/ml IL-6 (Peprotech), 3 mM Ca$^{2+}$ ions and 2 mM PO$_4^-$ (prepared in HEPES buffered saline) as previously described. Chai et al., Tissue Eng. Part A 17, 1083-1097 (2011). IL-6 was replaced (GFC-IL-6) with TH-17 supernatants in test conditions as an inflammatory trigger for differentiation. The mixtures were incubated in a shaking water-bath for 1 hour at 37° C. to allow for efficient neutralization of the IL-17 isoforms. Each condition was applied to the relevant hPDSC monolayer every other day until the end of culture period at day 8. Monolayers were either fixed in 10% neutral buffered formalin or stained with 1% alizarin red to measure deposited mineral, or lysed to isolate total RNA for osteogenic marker gene expression analysis. Prior to fixation, monolayers were visualised using standard microscopy techniques and the appearance of bone nodules was visually assessed.

To examine the effect of human serum from AS patients on hPDSC IL-17 mediated signalling, 10,000 cells/cm$^2$ cells were seeded in 24 well plates. The following day the media was removed and the monolayers were washed with sterile warmed PBS, following which the media was replaced with DMEM containing either 10% healthy human serum (HS) or AS patient serum (SRSC01, SRSC03, SRSC04, SRSC05, SRSC06 and SRSC07) with 1% sodium pyruvate and 1% antibiotics/antimycotics. The monolayers were incubated for 48 hours after which the media were discarded and monolayers terminated for total RNA isolation. Subsequently, expression of the downstream target gene IL-6 and osteogenic marker RUNX2 were evaluated.

Total RNA extraction, cDNA synthesis and qPCR: Monolayers were lysed using the RNeasy mini kit according to the kit instructions (Qiagen). Complementary DNA (cDNA) was synthesized by reverse transcription of 500 ng of total RNA using the high capacity cDNA reverse transcription kit (Applied Biosciences) under the following thermal cycling conditions; 25° C. for 10 mins, 37° C. for 120 mins and 85° C. for 5 minutes. To quantify the level of gene transcripts within each sample, primers (designed using Primer3 Plus, NCBI) were combined with iTaq universal SYBR green supermix (Biorad) and 10 ng cDNA, subsequently 10 μL aliquots were applied to Hard-Shell® 96-Well PCR Plates (Biorad). Thermal cycling conditions were as follows: 10 min at 95° C., with 40 cycles of 15 s at 95° C., 30 s at 60° C., and 20 s at 72° C., on a Bio-Rad CFX1000 Real-Time System. Each run consisted of melt curve analysis and template-free controls to confirm specific, single product amplification. All primer pairs produced single amplicons and reactions were of similar efficiency (95-100%), as established by standard dilution curve and analysis. Target gene quantification was achieved using the 2-ΔΔCT method described by Livak et al, relative to HPRT1.

IL-17A and IL-17F measurement by ELISA: IL-17A and IL-17F protein was measured in patient serum from AS patients using sandwich ELISA (Peprotech, London, UK). AS patient blood was isolated in BD Vacutainer SST tubes in the Rheumatology clinic at the Royal National Orthopaedic Hospital (Stanmore, UK). The NHS Research Ethics Committee approved all procedures. Following collection, the blood was centrifuged at 1000 g for 10 minutes at room temperature. The separated serum was then filtered through a 0.2-μm membrane. Aliquots of serum were stored at −80° C. prior to analysis. A 1:2 dilution of each AS patient serum was performed in diluent buffer provided in the human IL-17A and IL-17F ABTS kits (Peprotech, London, UK)

prior to analysis to reduce effects of serum matrix. Measurement of IL-17A and IL-17F was performed as per kit instructions.

Results: Utilising a biomimetic osteogenic assay (described in International Patent Publication WO2013189975), TH-17 supernatant (TH-17SN) was either treated with or without the inclusion of monoclonal antibodies directed towards IL-17A, IL-17F, or IL-17A/F. Osteogenic transcripts such as RUNX2, SP7 and BMP2 were analysed alongside markers of osteogenic matrix formation (BGLAP) and mineralisation (PHOSPHO1), in addition to assessment of the extent of mineralisation by alizarin red staining and assessment of the appearance of bone nodules. TH-17 cell supernatant potently enhanced hPDSC osteogenic differentiation and mineralisation (p<0.01). Both IL-6 expression and in vitro bone formation were blocked by neutralisation of IL-17A, IL-17F and IL-17A/F in the inflammatory milieu, with neutralisation of IL-17A/F exhibiting the largest effect. FIGS. 15A-G. Also, the appearance of bone nodules were visibly less in anti-IL-17A/F treated samples compared to treatment with anti-IL-17A or anti-IL-17F alone.

Figures 16A, 16B:
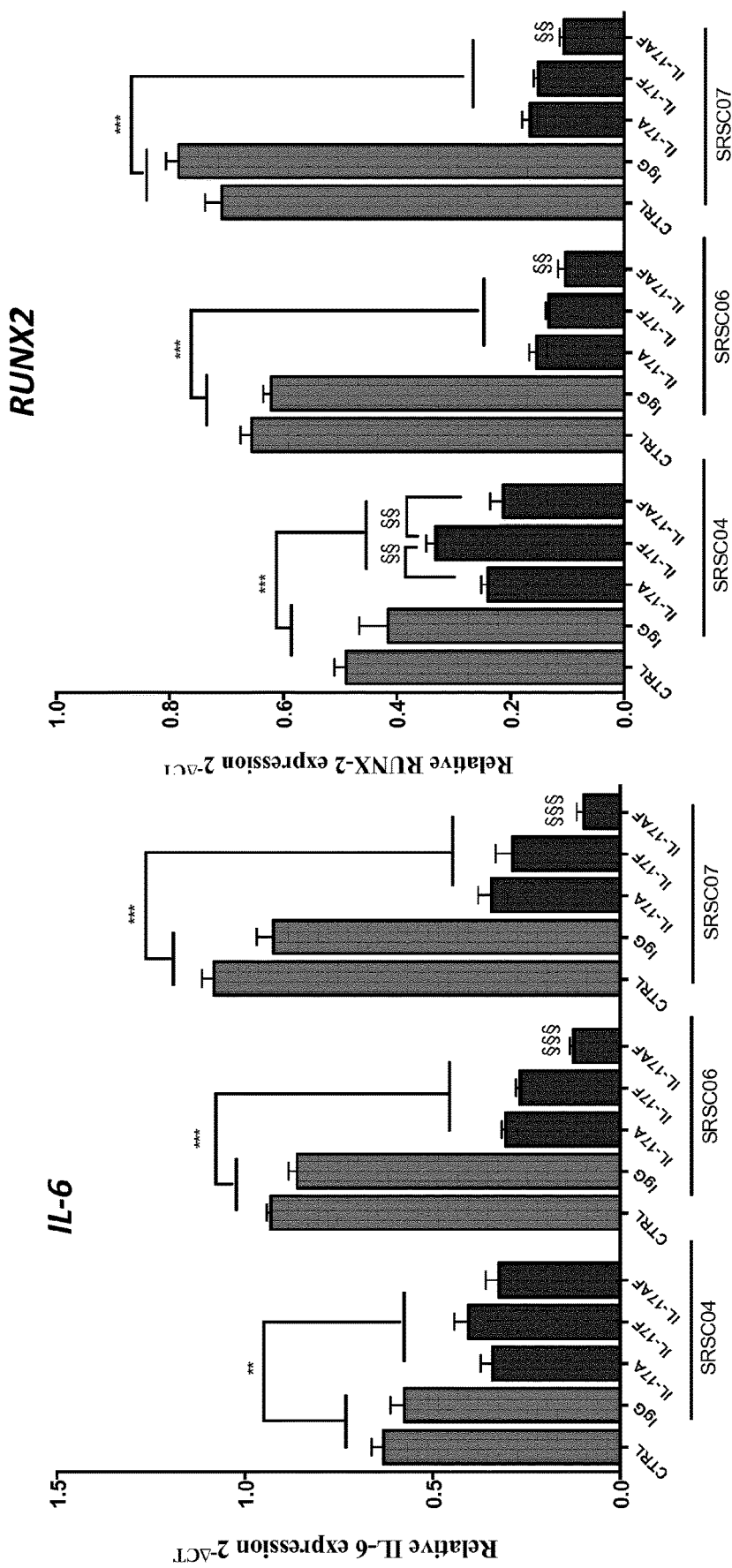
FIGS. 16A-16B: Bar graphs illustrating reduction in expression of IL-6 (FIG. 16A) and RUNX2 (FIG. 16B) in three patient samples (SRSC04, SRSCO6, and SRSCO7). hPDSCs treated with 10% AS patient serum (CTRL, first bar from left), or AS patient sera with IgG mAb control (second bar), IL-17A mAb (third bar), IL-17F mAb (fourth bar), IL-17A/F mAb (fifth bar) preincubation. Results are expressed as the mean relative expression±SEM. (*$p<0.001$; $p<0.01$; *$p<0.05$) § § § $p<0.01$ (comparisons between neutralisation groups as compared by one-way ANOVA (n=3) in all cases).

The presence of IL-17A and IL-17F in the serum of patients presenting with AS was quantified by ELISA. Both IL-17A and IL-17F proteins were measured in six patients and compared to the level in healthy human serum (HS). Varying levels of IL-17A and IL-17F were identifiable across the different patients with significantly greater levels of both IL-17A and IL-17F in three patients (P<0.01) compared to healthy human serum control group. Serum from patient samples from the remaining three patients appeared to exhibit similar IL-17A, however greater IL-17F expression in one patient compared to HAS control. To investigate the relevance of this, hPDSCs were treated with AS patient serum and incubated for 48 hours. The downstream target IL-6 and osteogenic marker RUNX2 were elevated. To define the importance of IL-17A and IL-17F in the expression of these markers, hPDSCs were treated with serum from AS patients (serum samples that exhibited significantly higher levels of both IL-17A and IL-17F and stimulated IL-6 and RUNX2 mRNA expression) following pre-incubation with either control IgG antibody or antibodies specific to IL-17A, IL-17F or IL-17A/F. The results indicated that blocking both IL-17A and IL-17F resulted in potent and significant decreases in IL-6 and RUNX2 mRNA expression. This effect was greatest with the antibody that had high affinity for IL-17A/F. FIGS. 16A & 16B.

Discussion: Inflammatory and degenerative joint diseases frequently elicit proliferative responses of the periarticular periosteal bone, leading to the formation of bony spurs (osteophytes). In inflammatory diseases such as AS, enthesophytes originate at the tendon insertion site (entheses) in peripheral joint and the vertebral bodies. It is hypothesized that the progenitor cells within the periosteum are intimately involved with this bone forming process and can lead to ankylosis with impairment of motion and joint dysfunction. The results described herein demonstrate that both IL-17A and IL-17F enhance in vitro osteogenic differentiation and bone formation from hPDSCs. Neutralization of IL-17A and IL-17F via a monoclonal antibody that binds both IL-17A/F (CA028_0496.g3 (Bimekizumab)) inhibited IL-6 gene expression and abrogated osteogenic gene (RUNX2, SP7, and BMP2) expression. CA028_0496.g3 also significantly mediated bone matrix mineralization effectors (BGLAP and PHOSPHO1), resulting in an observable reduction in matrix mineralization and bone nodule formation. Neutralization of IL-17A/F resulted in greatest inhibition of osteogenic differentiation markers and matrix mineralization compared to neutralization of IL-17A or IL-17F alone). Current therapeutics display limited efficacy in blocking enthesophyte formation; hence, the materials and methods described herein present a significant technical advantage for blocking this debilitating tissue morbidity.

The invention claimed is:

1. A method of treating psoriasis in a human in need thereof comprising administering an antibody which binds human IL-17A and human IL-17F to the human for:
 a first treatment period comprising administering the antibody at a dose of 320 mg once every four weeks for sixteen weeks; and
 a second treatment period comprising administering the antibody at a dose of 320 mg once every four or eight weeks;
 wherein the antibody comprises a light chain variable region comprising the amino acid sequence set forth in SEQ ID NO: 10, and a heavy chain variable region comprising the amino acid sequence set forth in SEQ ID NO: 11.

2. The method of claim 1, wherein the psoriasis is plaque psoriasis.

3. The method of claim 1, wherein the psoriasis is moderate-to-severe plaque psoriasis.

4. The method of claim 1, wherein the second treatment period comprises administering the antibody at a dose of 320 mg once every four weeks.

5. The method of claim 1, wherein the second treatment period comprises administering the antibody at a dose of 320 mg once every eight weeks.

6. The method of claim 1, wherein a reduction of plaque psoriasis after the first treatment is measured by PASI criteria.

7. A method of treating psoriasis in a human in need thereof comprising administering bimekizumab to the human for a first treatment period and a second treatment period, wherein the first treatment period comprises administering bimekizumab at a dose of 320 mg once every four weeks for sixteen weeks, and wherein the second treatment period comprises administering bimekizumab at a dose of 320 mg once every four or eight weeks.

8. The method of claim 7, wherein the psoriasis is plaque psoriasis.

9. The method of claim 7, wherein the psoriasis is moderate-to-severe plaque psoriasis.

10. The method of claim 7, wherein the second treatment period comprises administering bimekizumab at a dose of 320 mg once every four weeks.

11. The method of claim 7, wherein the second treatment period comprises administering bimekizumab at a dose of 320 mg once every eight weeks.

12. The method of claim 7, wherein a reduction of plaque psoriasis after the first treatment is measured by PASI criteria.

* * * * *

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRH1

<400> SEQUENCE: 1

Gly Phe Thr Phe Ser Asp Tyr Asn Met Ala
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRH2

<400> SEQUENCE: 2

Thr Ile Thr Tyr Glu Gly Arg Asn Thr Tyr Tyr Arg Asp Ser Val Lys
```

Gly

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRH3

<400> SEQUENCE: 3

Pro Pro Gln Tyr Tyr Glu Gly Ser Ile Tyr Arg Leu Trp Phe Ala His
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRL1

<400> SEQUENCE: 4

Arg Ala Asp Glu Ser Val Thr Thr Leu Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRL2

<400> SEQUENCE: 5

Leu Val Ser Asn Arg Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRL3

<400> SEQUENCE: 6

Gln Gln Thr Trp Ser Asp Pro Trp Thr
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRL1 for CA028_496.g3

```
<400> SEQUENCE: 7

Arg Ala Asp Glu Ser Val Arg Thr Leu His Met
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: CDRL2 for CA028_496.g3

<400> SEQUENCE: 8

Leu Val Ser Asn Ser Glu Ile
1               5

<210> SEQ ID NO 9
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain variable region - CA028_496 (gL7)

<400> SEQUENCE: 9

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg
            100                 105

<210> SEQ ID NO 10
<211> LENGTH: 107
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light Chain variable region - CA028_496.g3
      (gL57)

<400> SEQUENCE: 10

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
```

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys
            100                 105

<210> SEQ ID NO 11
<211> LENGTH: 125
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Heavy chain variable region - CA028_496 and
      CA028_496.g3 (gH9)

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser
        115                 120                 125

<210> SEQ ID NO 12
<211> LENGTH: 214
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain - CA028_496 (w/o signal)

<400> SEQUENCE: 12

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 214
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain - CA028_496.g3 (w/o signal)

<400> SEQUENCE: 13

```
Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 14
<211> LENGTH: 234
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain - CA028_496.g3 (w/ signal)

<400> SEQUENCE: 14

Met Ser Val Pro Thr Gln Val Leu Gly Leu Leu Leu Trp Leu Thr
1               5                   10                  15

Asp Ala Arg Cys Ala Ile Gln Leu Thr Gln Ser Pro Ser Ser Leu Ser
            20                  25                  30

Ala Ser Val Gly Asp Arg Val Thr Ile Thr Cys Arg Ala Asp Glu Ser
            35                  40                  45

Val Arg Thr Leu Met His Trp Tyr Gln Gln Lys Pro Gly Lys Ala Pro
        50                  55                  60

Lys Leu Leu Ile Tyr Leu Val Ser Asn Ser Glu Ile Gly Val Pro Asp
65                  70                  75                  80

Arg Phe Ser Gly Ser Gly Ser Gly Thr Asp Phe Arg Leu Thr Ile Ser
                85                  90                  95

Ser Leu Gln Pro Glu Asp Phe Ala Thr Tyr Tyr Cys Gln Gln Thr Trp
            100                 105                 110

Ser Asp Pro Trp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 15
<211> LENGTH: 452
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Heavy chain - CA028_496

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
```

```
            35                  40                  45
Ala Thr Ile Thr Tyr Glu Gly Arg Asn Thr Tyr Tyr Arg Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Ser Pro Pro Gln Tyr Tyr Glu Gly Ser Ile Tyr Arg Leu Trp Phe
                100                 105                 110
Ala His Trp Gly Gln Gly Thr Leu Val Thr Val Ser Ser Ala Ser Thr
            115                 120                 125
Lys Gly Pro Ser Val Phe Pro Leu Ala Pro Cys Ser Arg Ser Thr Ser
130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly Lys
        450
```

<210> SEQ ID NO 16
<211> LENGTH: 455
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Heavy chain CA028_496.g3 (w/o signal)

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350
```

```
Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455

<210> SEQ ID NO 17
<211> LENGTH: 474
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Heavy chain - CA8_496.g3 (w/ signal)

<400> SEQUENCE: 17

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Asn Met Ala Trp Val Arg Gln Ala Pro Gly Lys Gly Leu
    50                  55                  60

Glu Trp Val Ala Thr Ile Thr Tyr Glu Gly Arg Asn Thr Tyr Tyr Arg
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Pro Pro Gln Tyr Tyr Glu Gly Ser Ile Tyr Arg
        115                 120                 125

Leu Trp Phe Ala His Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240
```

-continued

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 18
<211> LENGTH: 321
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain variable region - CA028_496.g3

<400> SEQUENCE: 18

Gly Cys Cys Ala Thr Cys Cys Ala Gly Cys Thr Gly Ala Cys Cys Cys
1               5                   10                  15

Ala Gly Ala Gly Cys Cys Cys Thr Thr Cys Cys Thr Cys Thr Cys Thr
            20                  25                  30

Cys Ala Gly Cys Gly Cys Cys Ala Gly Thr Gly Thr Cys Gly Gly Ala
        35                  40                  45

Gly Ala Cys Ala Gly Ala Gly Thr Gly Ala Cys Thr Ala Thr Thr Ala
50                  55                  60

Cys Cys Thr Gly Cys Ala Gly Gly Gly Cys Thr Gly Ala Cys Gly Ala
65                  70                  75                  80

Ala Ala Gly Cys Gly Thr Gly Ala Gly Ala Ala Cys Ala Thr Thr Gly
                85                  90                  95

Ala Thr Gly Gly Ala Cys Thr Gly Gly Thr Ala Cys Cys Ala Ala Cys
            100                 105                 110

Ala Gly Ala Ala Gly Cys Cys Thr Gly Gly Cys Ala Ala Gly Cys
         115                 120                 125

Cys Cys Cys Cys Ala Ala Gly Cys Thr Cys Cys Thr Gly Ala Thr Cys
130                 135                 140

Thr Ala Thr Cys Thr Gly Gly Thr Thr Thr Cys Cys Ala Ala Thr Thr
145                 150                 155                 160

Cys Gly Gly Ala Gly Ala Thr Thr Gly Ala Gly Thr Cys Cys
        165                 170                 175

Cys Gly Ala Cys Ala Gly Gly Thr Thr Cys Ala Gly Cys Gly Gly Cys
        180                 185                 190

Ala Gly Thr Gly Gly Gly Thr Cys Thr Gly Gly Ala Ala Cys Thr Gly
        195                 200                 205

Ala Cys Thr Thr Thr Cys Gly Cys Cys Thr Gly Ala Cys Ala Ala Thr
        210                 215                 220

Cys Thr Cys Cys Thr Cys Ala Cys Thr Cys Cys Ala Gly Cys Cys Cys
225                 230                 235                 240

Gly Ala Ala Gly Ala Thr Thr Thr Cys Gly Cys Ala Cys Cys Thr
        245                 250                 255

Ala Cys Thr Ala Thr Thr Gly Cys Cys Ala Gly Cys Ala Gly Ala Cys
260 265 270

Thr Thr Gly Gly Ala Gly Cys Gly Ala Cys Cys Cys Thr Thr Gly Gly
275 280 285

Ala Cys Ala Thr Thr Thr Gly Gly Ala Cys Ala Gly Gly Gly Cys Ala
290 295 300

Cys Ala Ala Ala Ala Gly Thr Gly Gly Ala Gly Ala Thr Cys Ala Ala
305 310 315 320

Gly

<210> SEQ ID NO 19
<211> LENGTH: 375
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Heavy chain variable region - CA028_496.g3

<400> SEQUENCE: 19

Gly Ala Gly Gly Thr Thr Cys Ala Gly Cys Thr Cys Gly Thr Thr Gly
1 5 10 15

Ala Ala Thr Cys Cys Gly Gly Ala Gly Gly Cys Gly Gly Ala Cys Thr
20 25 30

Cys Gly Thr Gly Cys Ala Gly Cys Cys Thr Gly Gly Gly Gly Gly Cys
35 40 45

Thr Cys Cys Thr Thr Gly Cys Gly Gly Cys Thr Gly Ala Gly Cys Thr
50 55 60

Gly Cys Gly Cys Thr Gly Cys Cys Ala Gly Thr Gly Gly Cys Thr Thr
65 70 75 80

Cys Ala Cys Thr Thr Thr Cys Ala Gly Cys Gly Ala Thr Thr Ala Cys
85 90 95

Ala Ala Thr Ala Thr Gly Gly Cys Cys Thr Gly Gly Gly Thr Gly Cys
100 105 110

Gly Cys Cys Ala Gly Gly Cys Cys Cys Cys Ala Gly Gly Cys Ala Ala
115 120 125

Gly Gly Gly Thr Cys Thr Gly Gly Ala Gly Thr Gly Gly Thr Gly
              130                 135                 140

Gly Cys Cys Ala Cys Ala Ala Thr Thr Ala Cys Cys Thr Ala Thr Gly
145                 150                 155                 160

Ala Gly Gly Cys Ala Gly Ala Ala Ala Cys Ala Cys Thr Thr Ala
                165                 170                 175

Thr Thr Ala Cys Cys Gly Gly Ala Thr Thr Cys Ala Gly Thr Gly
              180                 185                 190

Ala Ala Ala Gly Gly Gly Cys Gly Ala Thr Thr Ala Cys Cys Ala
              195                 200                 205

Thr Cys Ala Gly Cys Ala Gly Gly Ala Thr Ala Ala Thr Gly Cys
210                 215                 220

Ala Ala Ala Gly Ala Ala Cys Ala Gly Thr Cys Thr Gly Thr Ala Cys
225                 230                 235                 240

Cys Thr Gly Cys Ala Gly Ala Thr Gly Ala Ala Cys Thr Thr Cys
                245                 250                 255

Thr Gly Ala Gly Ala Gly Cys Thr Gly Ala Gly Gly Ala Cys Ala Cys
              260                 265                 270

Cys Gly Cys Thr Gly Thr Cys Thr Ala Cys Thr Ala Thr Thr Gly Thr
              275                 280                 285

Gly Cys Ala Ala Gly Cys Cys Ala Cys Cys Cys Cys Ala Gly Gly Thr
290                 295                 300

Ala Cys Thr Ala Thr Gly Gly Ala Gly Gly Cys Thr Cys Ala Ala Thr
305                 310                 315                 320

Cys Thr Ala Cys Ala Gly Ala Thr Thr Gly Thr Gly Gly Thr Thr Thr
              325                 330                 335

Gly Cys Cys Cys Ala Thr Thr Gly Gly Gly Cys Cys Ala Gly Gly
              340                 345                 350

Gly Ala Ala Cys Ala Cys Thr Gly Gly Thr Gly Ala Cys Cys Gly Thr
          355                 360                 365

Cys Thr Cys Gly Ala Gly Cys
          370             375

<210> SEQ ID NO 20
<211> LENGTH: 705
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain - CA028_496 (w/ signal)

<400> SEQUENCE: 20

Ala Thr Gly Thr Cys Ala Gly Thr Cys Cys Cys Ala Cys Ala Cys Cys
1               5                   10                  15

Ala Gly Gly Thr Gly Cys Thr Gly Gly Cys Cys Thr Gly Cys Thr
              20                  25                  30

Thr Cys Thr Gly Thr Thr Gly Thr Gly Gly Cys Thr Ala Cys Cys
            35                  40                  45

Gly Ala Thr Gly Cys Thr Ala Gly Gly Thr Gly Thr Gly Cys Cys Ala
          50                  55                  60

Thr Cys Cys Ala Gly Cys Thr Gly Ala Cys Cys Cys Ala Gly Ala Gly
65                  70                  75                  80

Cys Cys Cys Thr Thr Cys Cys Thr Cys Thr Cys Ala Gly Cys
                85                  90                  95

-continued

```
Gly Cys Cys Ala Gly Thr Gly Thr Cys Gly Ala Gly Ala Cys Ala
            100                 105                 110
Gly Ala Gly Thr Gly Ala Cys Thr Ala Thr Ala Cys Cys Thr Gly
            115                 120                 125
Cys Ala Gly Gly Gly Cys Thr Gly Ala Cys Gly Ala Ala Gly Cys
            130                 135                 140
Gly Thr Gly Ala Cys Cys Ala Cys Ala Thr Thr Gly Ala Thr Gly Cys
145                     150                 155                 160
Ala Cys Thr Gly Gly Thr Ala Cys Cys Ala Ala

```
                515                 520                 525
Gly Gly Thr Ala Ala Cys Thr Cys Cys Cys Ala Gly Ala Gly Ala
        530                 535                 540
Gly Thr Gly Thr Cys Ala Cys Ala Gly Ala Gly Cys Ala Gly Ala
545                 550                 555                 560
Cys Ala Gly Cys Ala Gly Gly Ala Cys Ala Gly Cys Ala Cys Cys
                565                 570                 575
Thr Ala Cys Ala Gly Cys Cys Thr Cys Ala Gly Cys Ala Gly Cys Ala
        580                 585                 590
Cys Cys Cys Thr Gly Ala Cys Gly Cys Thr Gly Ala Gly Cys Ala Ala
        595                 600                 605
Ala Gly Cys Ala Gly Ala Cys Thr Ala Cys Gly Ala Gly Ala Ala Ala
        610                 615                 620
Cys Ala Cys Ala Ala Ala Gly Thr Cys Thr Ala Cys Gly Cys Cys Thr
625                 630                 635                 640
Gly Cys Gly Ala Ala Gly Thr Cys Ala Cys Cys Ala Thr Cys Ala
                645                 650                 655
Gly Gly Gly Cys Cys Thr Gly Ala Gly Cys Thr Cys Gly Cys Cys Cys
        660                 665                 670
Gly Thr Cys Ala Cys Ala Ala Ala Gly Ala Gly Cys Thr Thr Cys Ala
        675                 680                 685
Ala Cys Ala Gly Gly Gly Gly Ala Gly Ala Gly Thr Gly Thr Thr Ala
        690                 695                 700
Gly
705

<210> SEQ ID NO 21
<211> LENGTH: 645
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain - CA028_496.g3 (w/o signal)

<400> SEQUENCE: 21

Gly Cys Cys Ala Thr Cys Cys Ala Gly Cys Thr Gly Ala Cys Cys Cys
1               5                   10                  15
Ala Gly Ala Gly Cys Cys Cys Thr Thr Cys Cys Thr Cys Cys Cys Thr
                20                  25                  30
Cys Ala Gly Cys Gly Cys Cys Ala Gly Thr Gly Thr Cys Gly Gly Ala
        35                  40                  45
Gly Ala Cys Ala Gly Ala Gly Thr Gly Ala Cys Thr Ala Thr Cys Ala
        50                  55                  60
Cys Cys Thr Gly Cys Ala Gly Gly Gly Cys Thr Gly Ala Cys Gly Ala
65                  70                  75                  80
Ala Ala Gly Cys Gly Thr Gly Ala Gly Ala Ala Cys Ala Thr Thr Gly
                85                  90                  95
Ala Thr Gly Cys Ala Cys Thr Gly Gly Thr Ala Cys Cys Ala Ala Cys
                100                 105                 110
Ala Gly Ala Ala Gly Cys Cys Thr Gly Gly Cys Ala Ala Ala Gly Cys
        115                 120                 125
Cys Cys Cys Cys Ala Ala Gly Cys Thr Cys Thr Gly Ala Thr Cys Thr
        130                 135                 140
Thr Ala Thr Cys Thr Gly Gly Thr Thr Thr Cys Cys Ala Ala Thr Thr
```

-continued

```
145                 150                 155                 160

Cys Gly Gly Ala Gly Ala Thr Thr Gly Gly Ala Gly Thr Cys Cys Cys
                165                 170                 175

Cys Gly Ala Cys Ala Gly Gly Thr Thr Cys Ala Gly Cys Gly Gly Cys
            180                 185                 190

Ala Gly Thr Gly Gly Gly Thr Cys Thr Gly Gly Ala Ala Cys Thr Gly
        195                 200                 205

Ala Cys Thr Thr Thr Cys Gly Cys Cys Thr Gly Ala Cys Ala Ala Thr
    210                 215                 220

Cys Thr Cys Cys Thr Cys Ala Cys Thr Cys Cys Ala Gly Cys Cys Cys
225                 230                 235                 240

Gly Ala Ala Gly Ala Thr Thr Thr Cys Gly Cys Cys Ala Cys Cys Thr
                245                 250                 255

Ala Cys Thr Ala Thr Thr Gly Cys Cys Ala Gly Cys Ala Gly Ala Cys
            260                 265                 270

Thr Thr Gly Gly Ala Gly Cys Gly Ala Cys Cys Cys Thr Thr Gly Gly
        275                 280                 285

Ala Cys Ala Thr Thr Thr Gly Gly Ala Cys Ala Gly Gly Gly Cys Ala
    290                 295                 300

Cys Ala Ala Ala Ala Gly Thr Gly Gly Ala Gly Ala Thr Cys Ala Ala
305                 310                 315                 320

Gly Cys Gly Thr Ala Cys Gly Gly Thr Ala Gly Cys Gly Gly Cys Cys
                325                 330                 335

Cys Cys Ala Thr Cys Thr Gly Thr Cys Thr Thr Cys Ala Thr Cys Thr
            340                 345                 350

Thr Cys Cys Cys Gly Cys Cys Ala Thr Cys Thr Gly Ala Thr Gly Ala
        355                 360                 365

Gly Cys Ala Gly Thr Thr Gly Ala Ala Ala Thr Cys Thr Gly Gly Ala
    370                 375                 380

Ala Cys Thr Gly Cys Cys Thr Cys Thr Gly Thr Thr Gly Thr Gly Thr
385                 390                 395                 400

Gly Cys Cys Thr Gly Cys Thr Gly Ala Ala Thr Ala Ala Cys Thr Thr
                405                 410                 415

Cys Thr Ala Thr Cys Cys Cys Ala Gly Ala Gly Ala Gly Gly Cys Cys
            420                 425                 430

Ala Ala Ala Gly Thr Ala Cys Ala Gly Thr Gly Gly Ala Ala Gly Gly
        435                 440                 445

Thr Gly Gly Ala Thr Ala Ala Cys Gly Cys Cys Cys Thr Cys Cys Ala
    450                 455                 460

Ala Thr Cys Gly Gly Gly Thr Ala Ala Cys Thr Cys Cys Cys Ala Gly
465                 470                 475                 480

Gly Ala Gly Ala Gly Thr Gly Thr Cys Ala Cys Ala Gly Ala Gly Cys
                485                 490                 495

Ala Gly Gly Ala Cys Ala Gly Cys Ala Ala Gly Gly Ala Cys Ala Gly
            500                 505                 510

Cys Ala Cys Cys Thr Ala Cys Ala Gly Cys Cys Thr Cys Ala Gly Cys
        515                 520                 525

Ala Gly Cys Ala Cys Cys Cys Thr Gly Ala Cys Gly Cys Thr Gly Ala
    530                 535                 540

Gly Cys Ala Ala Ala Gly Cys Ala Gly Ala Cys Thr Ala Cys Gly Ala
545                 550                 555                 560

Gly Ala Ala Ala Cys Ala Cys Ala Ala Ala Gly Thr Cys Thr Ala Cys
                565                 570                 575
```

```
Gly Cys Cys Thr Gly Cys Gly Ala Ala Gly Thr Cys Ala Cys Cys
            580                 585                 590

Ala Thr Cys Ala Gly Gly Cys Thr Gly Ala Gly Cys Thr Cys
            595                 600                 605

Gly Cys Cys Cys Gly Thr Cys Ala Cys Ala Ala Gly Ala Gly Cys
    610                 615                 620

Thr Thr Cys Ala Ala Cys Ala Gly Gly Gly Ala Gly Ala Gly Thr
625                 630                 635                 640

Gly Thr Thr Ala Gly
                645

<210> SEQ ID NO 22
<211> LENGTH: 705
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Light chain - CA028_496.g3 (w/ signal)

<400> SEQUENCE: 22

Ala Thr Gly Thr Cys Ala Gly Thr Thr Cys Cys Ala Cys Ala Cys
1               5                   10                  15

Ala Gly Gly Thr Gly Cys Thr Gly Gly Cys Cys Thr Gly Cys Thr
            20                  25                  30

Thr Cys Thr Gly Thr Thr Gly Thr Gly Cys Thr Ala Cys Cys
        35                  40                  45

Gly Ala Thr Gly Cys Thr Ala Gly Gly Thr Thr Gly Cys Cys Ala
    50                  55                  60

Thr Cys Cys Ala Gly Cys Thr Gly Ala Cys Cys Cys Ala Gly Ala
65                  70                  75                  80

Cys Cys Cys Thr Thr Cys Cys Thr Cys Thr Cys Ala Gly Cys
            85                  90                  95

Gly Cys Cys Ala Gly Thr Gly Thr Cys Gly Gly Ala Gly Ala Cys Ala
    100                 105                 110

Gly Ala Gly Thr Gly Ala Cys Thr Ala Thr Ala Cys Cys Thr Gly
        115                 120                 125

Cys Ala Gly Gly Gly Cys Thr Gly Ala Cys Gly Ala Ala Gly Cys
    130                 135                 140

Gly Thr Gly Ala Gly Ala Ala Cys Ala Thr Thr Gly Ala Thr Gly Cys
145                 150                 155                 160

Ala Cys Thr Gly Gly Thr Ala Cys Cys Ala Ala Cys Ala Gly Ala Ala
            165                 170                 175

Gly Cys Cys Thr Gly Gly Cys Ala Ala Gly Cys Cys Cys Cys
            180                 185                 190

Ala Ala Gly Cys Thr Cys Cys Thr Gly Ala Thr Cys Thr Ala Thr Cys
        195                 200                 205

Thr Gly Gly Thr Thr Cys Cys Ala Ala Thr Thr Cys Gly Gly Ala
        210                 215                 220

Gly Ala Thr Thr Gly Gly Ala Gly Thr Cys Cys Cys Gly Ala Cys
225                 230                 235                 240

Ala Gly Gly Thr Thr Cys Ala Gly Cys Gly Gly Cys Ala Gly Thr Gly
            245                 250                 255

Gly Gly Thr Cys Thr Gly Gly Ala Ala Cys Thr Gly Ala Cys Thr Thr
        260                 265                 270
```

Thr Cys Gly Cys Cys Thr Gly Ala Cys Ala Ala Thr Cys Thr Cys Cys
275 280 285

Thr Cys Ala Cys Thr Cys Cys Ala Gly Cys Cys Cys Gly Ala Ala Gly
290 295 300

Ala Thr Thr Thr Cys Gly Cys Cys Ala Cys Cys Thr Ala Cys Thr Ala
305 310 315 320

Thr Thr Gly Cys Cys Ala Gly Cys Ala Gly Ala Cys Thr Thr Gly Gly
325 330 335

Ala Gly Cys Gly Ala Cys Cys Cys Thr Thr Gly Gly Ala Cys Ala Thr
340 345 350

Thr Thr Gly Gly Ala Cys Ala Gly Gly Gly Cys Ala Cys Ala Ala Ala
355 360 365

Ala Gly Thr Gly Gly Ala Gly Ala Thr Cys Ala Ala Gly Cys Gly Thr
370 375 380

Ala Cys Gly Gly Thr Ala Gly Cys Gly Gly Cys Cys Cys Cys Ala Thr
385 390 395 400

Cys Thr Gly Thr Cys Thr Thr Cys Ala Thr Cys Thr Thr Cys Cys Cys
405 410 415

Gly Cys Cys Ala Thr Cys Thr Gly Ala Thr Gly Ala Gly Cys Ala Gly
420 425 430

Thr Thr Gly Ala Ala Ala Thr Cys Thr Gly Gly Ala Ala Cys Thr Gly
435 440 445

Cys Cys Thr Cys Thr Gly Thr Thr Gly Thr Gly Thr Gly Cys Cys Thr
450 455 460

Gly Cys Thr Gly Ala Ala Thr Ala Ala Cys Thr Thr Cys Thr Ala Thr
465 470 475 480

Cys Cys Cys Ala Gly Ala Gly Ala Gly Gly Cys Cys Ala Ala Ala Gly
485 490 495

Thr Ala Cys Ala Gly Thr Gly Gly Ala Ala Gly Gly Thr Gly Gly Ala
500 505 510

Thr Ala Ala Cys Gly Cys Cys Cys Thr Cys Cys Ala Ala Thr Cys Gly
515 520 525

Gly Gly Thr Ala Ala Cys Thr Cys Cys Cys Ala Gly Gly Ala Gly Ala
530 535 540

Gly Thr Gly Thr Cys Ala Cys Ala Gly Ala Gly Cys Ala Gly Gly Ala
545 550 555 560

Cys Ala Gly Cys Ala Ala Gly Gly Ala Cys Ala Gly Cys Ala Cys Cys
565 570 575

Thr Ala Cys Ala Gly Cys Cys Thr Cys Ala Gly Cys Ala Gly Cys Ala
580 585 590

Cys Cys Cys Thr Gly Ala Cys Gly Cys Thr Gly Ala Gly Cys Ala Ala
595 600 605

Ala Gly Cys Ala Gly Ala Cys Thr Ala Cys Gly Ala Gly Ala Ala Ala
610 615 620

Cys Ala Cys Ala Ala Ala Gly Thr Cys Thr Ala Cys Gly Cys Cys Thr
625 630 635 640

Gly Cys Gly Ala Ala Gly Thr Cys Ala Cys Cys Cys Ala Thr Cys Ala
645 650 655

Gly Gly Gly Cys Cys Thr Gly Ala Gly Cys Thr Cys Gly Cys Cys Cys
660 665 670

Gly Thr Cys Ala Cys Ala Ala Ala Gly Ala Gly Cys Thr Thr Cys Ala
675 680 685

Ala Cys Ala Gly Gly Gly Gly Ala Gly Ala Gly Thr Gly Thr Thr Ala
    690                 695                 700

Gly
705

<210> SEQ ID NO 23
<211> LENGTH: 2020
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Heavy chain CA028_496 (w/ signal)

<400> SEQUENCE: 23

| | | | | | | |
|---|---|---|---|---|---|---|
| atggaatggt | cctgggtctt | cctgttttc | ctttctgtca | caaccggggt | gcacagcgag | 60 |
| gttcagctcg | ttgaatccgg | aggcggactc | gtgcagcctg | ggggctcctt | gcggctgagc | 120 |
| tgcgctgcca | gtggcttcac | tttcagcgat | tacaatatgg | cctgggtgcg | ccaggcccca | 180 |
| ggcaagggtc | tggagtgggt | ggccacaatt | acctatgagg | cagaaacac | ttattaccgg | 240 |
| gattcagtga | aagggcgatt | taccatcagc | agggataatg | caaagaacag | tctgtacctg | 300 |
| cagatgaact | ctctgagagc | tgaggacacc | gctgtctact | attgtgcaag | cccacccag | 360 |
| tactatgagg | gctcaatcta | cagattgtgg | tttgcccatt | ggggccaggg | aacactggtg | 420 |
| accgtctcga | gcgcttctac | aaagggccca | tccgtcttcc | cctggcgcc | ctgctccagg | 480 |
| agcacctccg | agagcacagc | cgccctgggc | tgcctggtca | aggactactt | ccccgaaccg | 540 |
| gtgacggtgt | cgtggaactc | aggcgccctg | accagcggcg | tgcacacctt | cccggctgtc | 600 |
| ctacagtcct | caggactcta | ctccctcagc | agcgtggtga | ccgtgccctc | cagcagcttg | 660 |
| ggcacgaaga | cctacacctg | caacgtagat | cacaagccca | gcaacaccaa | ggtggacaag | 720 |
| agagttggtg | agaggccagc | acagggaggg | agggtgtctg | ctggaagcca | ggctcagccc | 780 |
| tcctgcctgg | acgcacccg | gctgtgcagc | cccagcccag | ggcagcaagg | catgccccat | 840 |
| ctgtctcctc | acccggaggc | ctctgaccac | ccactcatg | cccagggaga | gggtcttctg | 900 |
| gattttccca | ccaggctccg | ggcagccaca | ggctggatgc | cctaccccca | ggccctgcgc | 960 |
| atacaggggc | aggtgctgcg | ctcagacctg | ccaagagcca | tatccgggag | accctgccc | 1020 |
| ctgacctaag | cccaccccaa | aggccaaact | ctccactccc | tcagctcaga | caccttctct | 1080 |
| cctcccagat | ctgagtaact | cccaatcttc | tctctgcaga | gtccaaatat | ggtccccat | 1140 |
| gcccaccatg | cccaggtaag | ccaacccagg | cctcgccctc | cagctcaagg | cgggacaggt | 1200 |
| gccctagagt | agcctgcatc | cagggacagg | cccccagccgg | gtgctgacgc | atccacctcc | 1260 |
| atctcttcct | cagcacctga | gttcctgggg | ggaccatcag | tcttcctgtt | cccccaaaa | 1320 |
| cccaaggaca | ctctcatgat | ctcccggacc | cctgaggtca | cgtgcgtggt | ggtggacgtg | 1380 |
| agccaggaag | accccgaggt | ccagttcaac | tggtacgtgg | atggcgtgga | ggtgcataat | 1440 |
| gccaagacaa | agccgcggga | ggagcagttc | aacagcacgt | accgtgtggt | cagcgtcctc | 1500 |
| accgtcctgc | accaggactg | gctgaacggc | aaggagtaca | agtgcaaggt | ctccaacaaa | 1560 |
| ggcctcccgt | cctccatcga | gaaaaccatc | tccaaagcca | aggtgggac | ccacggggtg | 1620 |
| cgagggccac | atggacagag | gtcagctcgg | cccaccctct | gccctgggag | tgaccgctgt | 1680 |
| gccaacctct | gtccctacag | ggcagccccg | agagccacag | gtgtacaccc | tgcccccatc | 1740 |
| ccaggaggag | atgaccaaga | accaggtcag | cctgacctgc | ctggtcaaag | gcttctaccc | 1800 |

| | |
|---|---|
| cagcgacatc gccgtggagt gggagagcaa tgggcagccg agaacaact acaagaccac | 1860 |
| gcctcccgtg ctggactccg acggctcctt cttcctctac agcaggctaa ccgtggacaa | 1920 |
| gagcaggtgg caggagggga atgtcttctc atgctccgtg atgcatgagg ctctgcacaa | 1980 |
| ccactacaca cagaagagcc tctccctgtc tctgggtaaa | 2020 |

<210> SEQ ID NO 24
<211> LENGTH: 1365
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Heavy chain - CA028_496.g3 (w/ exons, w/o signal)

<400> SEQUENCE: 24

| | |
|---|---|
| gaggttcagc tcgttgaatc cggaggcgga ctcgtgcagc ctggggggctc cttgcggctg | 60 |
| agctgcgctg ccagtggctt cactttcagc gattacaata tggcctgggt cgcgcaggcc | 120 |
| ccaggcaagg gtctggagtg ggtggccaca attacctatg agggcagaaa cacttattac | 180 |
| cgggattcag tgaaagggcg atttaccatc agcagggata atgcaaagaa cagtctgtac | 240 |
| ctgcagatga actctctgag agctgaggac accgctgtct actattgtgc aagcccaccc | 300 |
| cagtactatg agggctcaat ctacagattg tggtttgccc attggggcca gggaacactg | 360 |
| gtgaccgtct cgagcgcttc tacaaagggc ccatcggtct tccccctggc accctcctcc | 420 |
| aagagcacct ctgggggcac agcggccctg ggctgcctgg tcaaggacta cttccccgaa | 480 |
| ccggtgacgg tgtcgtggaa ctcaggcgcc ctgaccagcg gcgtgcacac cttcccggct | 540 |
| gtcctacagt cctcaggact ctactccctc agcagcgtgg tgaccgtgcc ctccagcagc | 600 |
| ttgggcaccc agacctacat ctgcaacgtg aatcacaagc ccagcaacac caaggtcgac | 660 |
| aagaaagttg agcccaaatc ttgtgacaaa actcacacat gcccaccgtg cccagcacct | 720 |
| gaactcctgg ggggaccgtc agtcttcctc ttccccccaa acccaaggga caccctcatg | 780 |
| atctcccgga cccctgaggt cacatgcgtg gtggtggacg tgagccacga agaccctgag | 840 |
| gtcaagttca actggtacgt ggacggcgtg gaggtgcata atgccaagac aaagccgcgg | 900 |
| gaggagcagt acaacagcac gtaccgtgtg gtcagcgtcc tcaccgtcct gcaccaggac | 960 |
| tggctgaatg gcaaggagta caagtgcaag gtctccaaca aagccctccc agcccccatc | 1020 |
| gagaaaacca tctccaaagc caaagcgcag ccccgagaac cacaggtgta caccctgccc | 1080 |
| ccatcccggg atgagctgac caagaaccag gtcagcctga cctgcctggt caaaggcttc | 1140 |
| tatcccagcg acatcgccgt ggagtgggag agcaatgggc agccggagaa caactacaag | 1200 |
| accacgcctc ccgtgctgga ctccgacggc tccttcttcc tctacagcaa gctcaccgtg | 1260 |
| gacaagagca ggtggcagca ggggaacgtc ttctcatgct ccgtgatgca tgaggctctg | 1320 |
| cacaaccact acacgcagaa gagcctctcc ctgtctccgg gtaaa | 1365 |

<210> SEQ ID NO 25
<211> LENGTH: 1422
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Heavy chain - CA028_496.g3 (w/ signal and exons)

<400> SEQUENCE: 25

```
atggaatggt cctgggtctt cctgttttc ctttctgtca caaccggggt gcacagcgag      60
gttcagctcg ttgaatccgg aggcggactc gtgcagcctg ggggctcctt gcggctgagc     120
tgcgctgcca gtggcttcac tttcagcgat tacaatatgg cctgggtgcg ccaggcccca     180
ggcaagggtc tggagtgggt ggccacaatt acctatgagg cagaaacac ttattaccgg      240
gattcagtga agggcgatt taccatcagc agggataatg caaagaacag tctgtacctg      300
cagatgaact ctctgagagc tgaggacacc gctgtctact attgtgcaag cccaccccag     360
tactatgagg gctcaatcta cagattgtgg tttgcccatt ggggccaggg aacactggtg     420
accgtctcga gcgcttctac aaagggccca tcggtcttcc ccctggcacc ctcctccaag     480
agcacctctg ggggcacagc ggccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc agcagcttg      660
ggcacccaga cctacatctg caacgtgaat cacaagccca gcaacaccaa ggtcgacaag     720
aaagttgagc ccaaatcttg tgacaaaact cacacatgcc caccgtgccc agcacctgaa     780
ctcctggggg gaccgtcagt cttcctcttc cccccaaaac ccaaggacac cctcatgatc     840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agcgcagccc cgagaaccac aggtgtacac cctgcccca     1140
tcccgggatg agctgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cgcagaagag cctctccctg tctccgggta aa                       1422
```

<210> SEQ ID NO 26
<211> LENGTH: 1422
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Heavy chain - CA028_496.g3 (w/ signal)

<400> SEQUENCE: 26

```
atggaatggt cctgggtctt cctgttttc ctttctgtca caaccggggt gcacagcgag      60
gttcagctcg ttgaatccgg aggcggactc gtgcagcctg ggggctcctt gcggctgagc     120
tgcgctgcca gtggcttcac tttcagcgat tacaatatgg cctgggtgcg ccaggcccca     180
ggcaagggtc tggagtgggt ggccacaatt acctatgagg cagaaacac ttattaccgg      240
gattcagtga agggcgatt taccatcagc agggataatg caaagaacag tctgtacctg      300
cagatgaact ctctgagagc tgaggacacc gctgtctact attgtgcaag cccaccccag     360
tactatgagg gctcaatcta cagattgtgg tttgcccatt ggggccaggg aacactggtg     420
accgtctcga gcgcttctac aaagggccca tcggtcttcc ccctggcacc ctcctccaag     480
```

```
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg     660 ggcacccaga cctacatctg caacgtgaat cacaagccca gcaacaccaa ggtcgacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agcgcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aa                      1422
```

<210> SEQ ID NO 27
<211> LENGTH: 132
<212> TYPE: PRT
<213> ORGANISM: Homo sapiens

<400> SEQUENCE: 27

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
        50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala
    130

<210> SEQ ID NO 28
<211> LENGTH: 133
<212> TYPE: PRT
<213> ORGANISM: Homo sapiens

<400> SEQUENCE: 28

Arg Lys Ile Pro Lys Val Gly His Thr Phe Phe Gln Lys Pro Glu Ser
1               5                   10                  15

```
                    -continued

Cys Pro Pro Val Pro Gly Gly Ser Met Lys Leu Asp Ile Gly Ile Ile
            20              25              30

Asn Glu Asn Gln Arg Val Ser Met Ser Arg Asn Ile Glu Ser Arg Ser
        35              40              45

Thr Ser Pro Trp Asn Tyr Thr Val Thr Trp Asp Pro Asn Arg Tyr Pro
    50              55              60

Ser Glu Val Val Gln Ala Gln Cys Arg Asn Leu Gly Cys Ile Asn Ala
65              70              75              80

Gln Gly Lys Glu Asp Ile Ser Met Asn Ser Val Pro Ile Gln Gln Glu
            85              90              95

Thr Leu Val Val Arg Arg Lys His Gln Gly Cys Ser Val Ser Phe Gln
            100             105             110

Leu Glu Lys Val Leu Val Thr Val Gly Cys Thr Cys Val Thr Pro Val
        115             120             125

Ile His His Val Gln
        130
```